US012806066B2

(12) United States Patent
Eisenfrats et al.

(10) Patent No.: US 12,806,066 B2
(45) Date of Patent: Nov. 24, 2026

(54) AEROGEL IMPLANTS FOR CONTRACEPTION

(71) Applicant: Contraline, Inc., Charlottesville, VA (US)

(72) Inventors: Kevin S. Eisenfrats, Charlottesville, VA (US); Nicholas Matsumoto, Charlottesville, VA (US); Yelena Tropsha, Plymouth, MN (US)

(73) Assignee: Contraline, Inc., Charlottesville, VA (US)

( * ) Notice: Subject to any disclaimer, the term of this patent is extended or adjusted under 35 U.S.C. 154(b) by 0 days.

(21) Appl. No.: 18/935,296

(22) Filed: Nov. 1, 2024

(65) Prior Publication Data

US 2025/0134702 A1 May 1, 2025

Related U.S. Application Data

(60) Provisional application No. 63/668,151, filed on Jul. 5, 2024, provisional application No. 63/595,314, filed on Nov. 1, 2023.

(51) Int. Cl.
*A61F 6/22* (2006.01)
*A61L 27/52* (2006.01)

(52) U.S. Cl.
CPC .............. *A61F 6/225* (2013.01); *A61L 27/52* (2013.01)

(58) Field of Classification Search
CPC .. A61F 6/225; A61F 6/206; A61F 6/22; A61F 6/20; A61L 27/52; A61L 2430/36; A61B 17/12022; A61B 17/12099; F26B 5/06
See application file for complete search history.

(56) References Cited

U.S. PATENT DOCUMENTS

| | | | |
|---|---|---|---|
| 3,223,083 A | 12/1965 | Cobey | |
| 3,716,056 A | 2/1973 | Brodsky et al. | |
| 4,036,933 A * | 7/1977 | Laufer | C09C 1/3027 423/338 |
| 4,044,757 A | 8/1977 | McWhorter et al. | |

(Continued)

FOREIGN PATENT DOCUMENTS

| | | |
|---|---|---|
| AU | 2016353345 A1 | 6/2018 |
| AU | 2018205258 A1 | 7/2019 |

(Continued)

OTHER PUBLICATIONS

Koul, V. et al., “Reversibility With Sodium Bicarbonate of Styrene Maleic Anhydride, an Intravasal Injectable Contraceptive, in Male Rats”, Contraception 58(4):227-31 (1998).

(Continued)

*Primary Examiner* — Ophelia A Hawthorne
(74) *Attorney, Agent, or Firm* — New River Valley IP Law, P.C.; Ashley M. Gates; Michele L. Mayberry

(57) ABSTRACT

Embodiments of the invention include aerogel implants and methods for making aerogel implants, and methods of implantation of aerogel implants. Such implants are configured to swell in vivo following insertion into a body cavity or lumen, such as a vas deferens or fallopian tube, to provide an occlusion. In embodiments, in vivo swelling results in an aerogel implant (e.g., a rehydrated hydrogel implant) that is dynamically responsive to vessel contraction.

20 Claims, 11 Drawing Sheets

(56) References Cited

U.S. PATENT DOCUMENTS 4,269,174 A 5/1981 Adair
4,273,109 A 6/1981 Enderby
4,804,691 A 2/1989 English et al.
4,887,605 A 12/1989 Angelsen et al.
4,920,982 A 5/1990 Goldstein
4,967,949 A 11/1990 Sandhaus
4,978,336 A 12/1990 Capozzi et al.
4,979,942 A 12/1990 Wolf et al.
5,065,751 A 11/1991 Wolf
5,240,997 A 8/1993 Yanai et al.
5,248,311 A 9/1993 Black et al.
5,258,042 A 11/1993 Mehta
5,380,317 A 1/1995 Everett et al.
5,383,896 A 1/1995 Gershony et al.
5,437,660 A 8/1995 Johnson et al.
5,488,075 A 1/1996 Guha
5,575,815 A 11/1996 Slepian et al.
5,607,419 A 3/1997 Amplatz et al.
5,612,052 A 3/1997 Shalaby
5,667,767 A 9/1997 Greff et al.
5,695,740 A 12/1997 Porter
5,702,717 A 12/1997 Cha et al.
5,714,159 A 2/1998 Shalaby
5,749,968 A 5/1998 Melanson et al.
5,797,397 A 8/1998 Rosenberg
5,833,682 A 11/1998 Amplatz et al.
5,866,554 A 2/1999 Shalaby et al.
5,947,893 A 9/1999 Agrawal et al.
5,968,018 A 10/1999 Freeman et al.
5,989,580 A 11/1999 Wallace et al.
6,037,331 A 3/2000 Shalaby et al.
6,066,325 A 5/2000 Wallace et al.
6,096,052 A 8/2000 Callister et al.
6,103,254 A 8/2000 Wallace et al.
6,112,747 A 9/2000 Jones et al.
6,197,940 B1 3/2001 Klinefelter
6,224,893 B1 5/2001 Langer et al.
6,263,880 B1 7/2001 Parker et al.
6,297,337 B1 10/2001 Marchant et al.
6,328,229 B1 12/2001 Duronio et al.
6,378,524 B1 4/2002 Jones
6,379,373 B1 4/2002 Sawhney et al.
6,394,314 B1 5/2002 Sawhney et al.
6,413,539 B1 7/2002 Shalaby
6,432,116 B1 8/2002 Callister et al.
6,454,762 B1 9/2002 Rösler et al.
6,461,325 B1 10/2002 Delmotte et al.
6,461,569 B1 10/2002 Boudreaux
6,464,663 B1 10/2002 Zinger
6,485,426 B2 11/2002 Sandhu
6,514,534 B1 2/2003 Sawhney
6,514,535 B2 2/2003 Marchant
6,517,531 B2 2/2003 Liu et al.
6,531,111 B1 3/2003 Whalen et al.
6,610,033 B1 8/2003 Melanson et al.
6,660,247 B1 12/2003 Gutowska et al.
6,703,047 B2 3/2004 Sawhney et al.
6,719,778 B1 4/2004 Tassel et al.
6,723,090 B2 4/2004 Altshuler et al.
6,723,781 B1 4/2004 Frate et al.
6,756,031 B2 6/2004 Evans et al.
6,802,838 B2 10/2004 Loeb et al.
6,852,099 B2 2/2005 Redl et al.
6,858,219 B2 2/2005 Evans et al.
6,957,747 B2 10/2005 Peeler et al.
6,970,587 B1 11/2005 Rogers
7,022,073 B2 4/2006 Fan et al.
7,073,504 B2 7/2006 Callister et al.
7,135,027 B2 11/2006 Delmotte
7,160,931 B2 1/2007 Cheng et al.
7,252,677 B2 8/2007 Burwell et al.
7,291,673 B2 11/2007 Hubbell et al.
7,347,850 B2 3/2008 Sawhney
7,396,354 B2 7/2008 Rychnovsky et al.
7,398,780 B2 7/2008 Callister et al.
7,641,075 B2 1/2010 Crews
7,694,683 B2 4/2010 Callister et al.
7,754,212 B2 7/2010 Klinefelter
7,789,891 B2 9/2010 Wallace
7,871,637 B2 1/2011 Qian et al.
7,914,514 B2 3/2011 Calderon
7,914,541 B2 3/2011 Sawhney et al.
7,918,863 B2 4/2011 Nguyen et al.
7,975,697 B2 7/2011 Callister et al.
8,048,086 B2 11/2011 Lee-Sepsick et al.
8,048,101 B2 11/2011 Lee-Sepsick et al.
8,052,669 B2 11/2011 Lee-Sepsick et al.
8,105,622 B2 1/2012 Sawhney
8,113,205 B2 2/2012 Callister et al.
8,123,693 B2 2/2012 Connor et al.
8,137,304 B2 3/2012 Chavez et al.
8,226,680 B2 7/2012 Wallace
8,235,047 B2 8/2012 Swann et al.
8,257,723 B2 9/2012 Noyes
8,303,981 B2 11/2012 Wallace et al.
8,316,853 B2 11/2012 Lee-Sepsick et al.
8,316,854 B2 11/2012 Lee-Sepsick et al.
8,322,341 B2 12/2012 Koeller
8,324,193 B2 12/2012 Lee-Sepsick et al.
8,336,552 B2 12/2012 Lee-Sepsick et al.
8,343,183 B2 1/2013 D'Alessio et al.
8,343,710 B1 1/2013 Anseth et al.
8,353,892 B2 1/2013 Thompson et al.
8,357,378 B2 1/2013 Wallace et al.
8,360,064 B2 1/2013 Swann et al.
8,434,489 B2 5/2013 Gopal et al.
8,440,487 B2 5/2013 Furumura
8,475,532 B2 7/2013 Vresilovic et al.
8,512,729 B2 8/2013 Wallace et al.
8,523,848 B2 9/2013 Fried et al.
8,550,085 B2 10/2013 Callister et al.
8,551,001 B2 10/2013 Connor et al.
8,603,025 B2 12/2013 Pongratz et al.
8,603,080 B1 12/2013 Fried et al.
8,603,511 B2 12/2013 Wallace et al.
8,613,282 B2 12/2013 Nikolchev et al.
8,689,792 B2 4/2014 Jimenez et al.
8,695,606 B2 4/2014 Lee-Sepsick et al.
8,726,906 B2 5/2014 Lee-Sepsick et al.
8,766,853 B2 7/2014 Furumura et al.
8,801,764 B2 8/2014 Suarez et al.
8,933,784 B2 1/2015 Furumura et al.
8,960,501 B2 2/2015 Pappalardo
8,986,730 B2 3/2015 Sawhney et al.
9,034,053 B2 5/2015 Lee-Sepsick et al.
9,155,543 B2 10/2015 Walsh et al.
9,180,196 B2 11/2015 Anseth et al.
9,193,816 B2 11/2015 Jiang et al.
9,220,880 B2 12/2015 Lee-Sepsick et al.
9,308,283 B2 4/2016 Campbell et al.
9,445,795 B2 9/2016 Ohri et al.
9,463,004 B2 10/2016 Campbell et al.
9,492,383 B2 11/2016 Gravett et al.
9,566,365 B2 2/2017 Kaplan et al.
9,586,005 B2 3/2017 Steffen
9,707,319 B2 7/2017 Geppert et al.
9,750,695 B2 9/2017 Richard
9,861,515 B2 1/2018 DePinto et al.
9,872,936 B2 1/2018 Grinstaff et al.
10,046,115 B2 8/2018 Bokelman et al.
10,155,063 B2 12/2018 Herr et al.
10,507,264 B1 12/2019 Lowman et al.
10,576,206 B2 3/2020 Edwards et al.
10,751,124 B2 8/2020 Eisenfrats et al.
11,253,391 B2 2/2022 Grover et al.
11,278,641 B2 3/2022 Herr et al.
11,318,040 B2 5/2022 Grover et al.
11,510,807 B2 11/2022 Grover et al.
11,850,306 B2 * 12/2023 Auvinen .................. F26B 5/06
11,904,068 B2 2/2024 Herr et al.
11,951,032 B2 4/2024 Grover et al.
11,957,616 B2 4/2024 Grover et al.
12,383,421 B2 8/2025 Eisenfrats et al.
12,589,182 B2 3/2026 Herr et al.

(56) References Cited

U.S. PATENT DOCUMENTS

2002/0032463 A1 3/2002 Cruise et al.
2002/0051750 A1 5/2002 Schutt et al.
2002/0106328 A1 8/2002 Johnson et al.
2002/0106411 A1 8/2002 Wironen et al.
2002/0161358 A1 10/2002 Liu et al.
2002/0173586 A1 11/2002 Jeong et al.
2003/0185758 A1 10/2003 Evans et al.
2003/0199865 A1 10/2003 Knudson et al.
2003/0206864 A1 11/2003 Mangin
2004/0013292 A1 1/2004 Raunig
2004/0062808 A1 4/2004 Langrana et al.
2004/0087930 A1 5/2004 Whalen et al.
2004/0158270 A1 8/2004 Wyzgala et al.
2004/0228509 A1 11/2004 Holupka et al.
2004/0240715 A1 12/2004 Wicker et al.
2004/0267308 A1 12/2004 Bagaoisan et al.
2005/0045183 A1 3/2005 Callister et al.
2005/0142162 A1 6/2005 Hunter et al.
2005/0147599 A1 7/2005 Hunter et al.
2005/0149117 A1 7/2005 Khosravi et al.
2005/0192616 A1 9/2005 Callister et al.
2005/0266086 A1 12/2005 Sawhney
2005/0283098 A1 12/2005 Conston et al.
2005/0288481 A1 12/2005 DesNoyer et al.
2006/0121087 A1 6/2006 Williams et al.
2006/0222596 A1 10/2006 Askari et al.
2006/0241452 A1 10/2006 Cerofolini
2006/0253112 A1 11/2006 Suarez et al.
2007/0016128 A1 1/2007 Keller
2007/0060906 A1 3/2007 Wu
2007/0163601 A1 7/2007 Pollock et al.
2007/0197954 A1 8/2007 Keenan
2007/0231366 A1 10/2007 Sawhney et al.
2008/0039890 A1 2/2008 Matson et al.
2008/0045865 A1 2/2008 Kislev
2008/0071269 A1 3/2008 Hilario et al.
2008/0103564 A1 5/2008 Burkinshaw et al.
2008/0131509 A1 6/2008 Hossainy et al.
2008/0154345 A1 6/2008 Taylor
2008/0215034 A1 9/2008 Clayton et al.
2008/0262613 A1 10/2008 Gogolewski
2008/0274980 A1 11/2008 Messersmith et al.
2008/0308110 A1 12/2008 Callister et al.
2009/0024155 A1 1/2009 Lee-Sepsick et al.
2009/0048588 A1 2/2009 Peng et al.
2009/0053276 A1 2/2009 Richard
2009/0076459 A1 3/2009 Goldberg
2009/0127288 A1 5/2009 Keller
2009/0196930 A1 8/2009 Surber et al.
2009/0274678 A1 11/2009 Calabro et al.
2009/0277457 A1 11/2009 Hoey et al.
2010/0003297 A1 1/2010 Tobias et al.
2010/0006339 A1 1/2010 Desai
2010/0063392 A1 3/2010 Nishina et al.
2010/0068153 A1 3/2010 Bangera et al.
2010/0089406 A1 4/2010 Kachiguina
2010/0130859 A1 5/2010 Jarvi
2010/0158813 A1 6/2010 Paradossi et al.
2010/0272672 A1 10/2010 Kita et al.
2010/0280312 A1 11/2010 D'Alessio et al.
2010/0318035 A1 12/2010 Edwards et al.
2011/0021970 A1 1/2011 Vo-Dinh et al.
2011/0065809 A1 3/2011 Benz et al.
2011/0094519 A1 4/2011 Gopal et al.
2011/0125185 A1 5/2011 Stopek et al.
2011/0137150 A1 6/2011 Connor et al.
2011/0165114 A1 7/2011 McCoy et al.
2011/0245866 A1 10/2011 Cassingham et al.
2012/0014978 A1 1/2012 Hafner et al.
2012/0149781 A1 6/2012 Lee et al.
2012/0165804 A1 6/2012 Newell et al.
2012/0192872 A1 8/2012 Rudakov et al.
2012/0226226 A1 9/2012 Edwards et al.
2012/0295214 A1 11/2012 Wang et al.
2013/0018314 A1 1/2013 Teague et al.
2013/0131632 A1 5/2013 Mudd et al.
2013/0220335 A1 8/2013 Lee-Sepsick et al.
2013/0230496 A1 9/2013 Mohapatra et al.
2013/0244975 A1 9/2013 Baldwin et al.
2013/0245604 A1 9/2013 Kouyoumjian et al.
2013/0287742 A1 10/2013 Kaplan et al.
2013/0331770 A1 12/2013 Kirk et al.
2013/0331771 A1 12/2013 Kirk et al.
2014/0046182 A1 2/2014 Connor et al.
2014/0114261 A1 4/2014 Geppert et al.
2014/0121699 A1 5/2014 Anderson et al.
2014/0128497 A1 5/2014 Ladet et al.
2014/0256831 A1 9/2014 Ito et al.
2014/0261446 A1 9/2014 Sjoquist et al.
2014/0276384 A1 9/2014 Schwab et al.
2014/0376793 A1 12/2014 Lee et al.
2015/0005409 A1 1/2015 Horiguchi et al.
2015/0045729 A1 2/2015 Denzer et al.
2015/0068531 A1 3/2015 Lee-Sepsick et al.
2015/0136144 A1 5/2015 DePinto et al.
2015/0196684 A1 7/2015 Guillen et al.
2015/0231246 A1 8/2015 Tae et al.
2016/0024326 A1 1/2016 Khan et al.
2016/0114046 A1 4/2016 Brudno et al.
2016/0151124 A1 6/2016 Domb et al.
2016/0151535 A1 6/2016 Hoare et al.
2016/0153999 A1 6/2016 Tibbitt et al.
2016/0193392 A1 7/2016 Askari et al.
2016/0263278 A1 9/2016 Grinstaff et al.
2016/0296640 A1 10/2016 Trifiro et al.
2016/0317621 A1 11/2016 Bright
2017/0014153 A1 1/2017 To et al.
2017/0014569 A1 1/2017 Flanagan et al.
2017/0061607 A1 3/2017 Eskandari et al.
2017/0130194 A1 5/2017 Lee et al.
2017/0136143 A1* 5/2017 Herr ........................ A61L 27/52
2017/0136144 A1 5/2017 Herr et al.
2017/0189581 A1 7/2017 Desai et al.
2017/0296749 A1 10/2017 Porcher
2018/0028715 A1 2/2018 Eisenfrats
2018/0092661 A1 4/2018 Prabhu
2018/0092769 A1 4/2018 DePinto et al.
2018/0104059 A1 4/2018 Roche et al.
2018/0185096 A1 7/2018 Eisenfrats et al.
2018/0369481 A1 12/2018 Pedersen et al.
2018/0369482 A1 12/2018 Pedersen et al.
2018/0369483 A1 12/2018 Olesen et al.
2019/0009029 A1 1/2019 Fabricius et al.
2019/0038454 A1 2/2019 Eisenfrats et al.
2019/0053790 A1 2/2019 Grover et al.
2019/0060513 A1 2/2019 Herr et al.
2019/0142453 A1 5/2019 Efremkin
2019/0224419 A1 7/2019 Pedersen et al.
2019/0321519 A1 10/2019 Weaver et al.
2020/0146876 A1 5/2020 Grover et al.
2020/0147301 A1 5/2020 Grover et al.
2020/0237388 A1 7/2020 Eisenfrats et al.
2020/0352649 A1 11/2020 Eisenfrats et al.
2020/0384207 A1 12/2020 Egesborg et al.
2022/0015742 A1 1/2022 Grover et al.
2022/0142812 A1 5/2022 Grover et al.
2022/0168461 A1 6/2022 Herr et al.
2022/0175672 A1 6/2022 Grover et al.
2022/0313475 A1 10/2022 Grover et al.
2023/0116862 A1 4/2023 Grover et al.
2024/0325593 A1 10/2024 Herr et al.
2025/0002660 A1* 1/2025 Huang ..................... C08J 9/286
2026/0151545 A1 6/2026 Tropsha et al.

FOREIGN PATENT DOCUMENTS

AU 2019380413 A1 5/2021
AU 2021277608 A1 12/2021
CA 3004745 A1 5/2017
CA 2769162 C 12/2017
CA 3053451 A1 7/2018
CA 3078365 A1 4/2019
CA 3117577 A1 5/2020
CN 1812746 B 7/2011

(56) References Cited

FOREIGN PATENT DOCUMENTS

| | | | | | |
|---|---|---|---|---|---|
| CN | 101812194 | B | | 4/2012 | |
| CN | 203493942 | U | | 3/2014 | |
| CN | 103724638 | B | | 12/2015 | |
| CN | 102883752 | B | | 3/2016 | |
| CN | 105390712 | A | | 3/2016 | |
| CN | 110381854 | A | | 10/2019 | |
| CN | 111629684 | A | | 9/2020 | |
| CN | 114272205 | A | * | 4/2022 | |
| EP | 0547530 | A1 | | 6/1993 | |
| EP | 2233160 | A2 | | 9/2010 | |
| EP | 3275469 | A1 | | 1/2018 | |
| EP | 3373870 | A1 | | 9/2018 | |
| EP | 3565484 | A1 | | 11/2019 | |
| EP | 3880273 | A1 | | 9/2021 | |
| EP | 4400166 | A2 | | 7/2024 | |
| ES | 2686927 | T3 | | 10/2018 | |
| JP | 2006520220 | A | | 9/2006 | |
| JP | 5330533 | B2 | | 10/2013 | |
| JP | 2016155994 | A | | 9/2016 | |
| JP | 2018033954 | A | | 3/2018 | |
| JP | 2022506078 | A | | 1/2022 | |
| WO | 03093338 | A2 | | 11/2003 | |
| WO | 2005000161 | A2 | | 1/2005 | |
| WO | 2009137446 | A2 | | 11/2009 | |
| WO | 2009148405 | A1 | | 12/2009 | |
| WO | 2009137446 | A3 | | 2/2010 | |
| WO | 2010057043 | A1 | | 5/2010 | |
| WO | 2008115694 | A3 | | 6/2010 | |
| WO | 2012031144 | A2 | | 3/2012 | |
| WO | 2012112417 | A2 | | 8/2012 | |
| WO | 2013036847 | A1 | | 3/2013 | |
| WO | 2014169708 | A1 | | 10/2014 | |
| WO | 2015168090 | A1 | | 11/2015 | |
| WO | 2016094535 | A1 | | 6/2016 | |
| WO | 2016145299 | A1 | | 9/2016 | |
| WO | 2016154288 | A1 | | 9/2016 | |
| WO | 2016164828 | A1 | | 10/2016 | |
| WO | 2017044983 | A1 | | 3/2017 | |
| WO | 2017083753 | A1 | | 5/2017 | |
| WO | 2017114908 | A1 | | 7/2017 | |
| WO | 2017152036 | A1 | | 9/2017 | |
| WO | 2017174071 | A1 | | 10/2017 | |
| WO | 2017180174 | A1 | | 10/2017 | |
| WO | WO-2017197262 | A1 | * | 11/2017 | ......... A61L 24/0094 |
| WO | 2018104537 | A1 | | 6/2018 | |
| WO | 2018129369 | A1 | | 7/2018 | |
| WO | 2018144481 | A1 | | 8/2018 | |
| WO | 2019070632 | A1 | | 4/2019 | |
| WO | 2020102234 | A1 | | 5/2020 | |
| WO | 2021035217 | A1 | | 2/2021 | |
| WO | 2021231717 | A1 | | 11/2021 | |
| WO | 2021243046 | A1 | | 12/2021 | |
| WO | 2024086828 | A2 | | 4/2024 | |
| WO | 2025097044 | A1 | | 5/2025 | |

OTHER PUBLICATIONS

Lahiri, D., Dua, R., Zhang, C., de Socarraz-Novoa, I., Bhat, A., Ramaswamy, S., & Agarwal, A. (2012). Graphene nanoplatelet-induced strengthening of ultrahigh molecular weight polyethylene and biocompatibility in vitro. ACS applied materials & interfaces, 4(4), 2234-2241.

Lee, W. C., Lim, C. H. Y., Shi, H., Tang, L.A., Wang, Y., Lim, C. T., & Loh, K. P. (2011). Origin of enhanced stem cell growth and differentiation on graphene and graphene oxide. ACS nano, 5(9), 7334-7341.

Li, C. et al., “Functionalization of Multiwalled Carbon Nanotubes and Their pH-Responsive Hydrogels with Amyloid Fibrils”, Langmuir, 2012, 28, 10142-10146, 5 pages.

Li, J. and Mooney, D. J., “Designing hydrogels for controlled drug delivery.” Nat. Rev. Mater. 1, 1-17, 2016, 38 pages.

Liu, X. et al., “The Relationship Between the Vas Volume and the Anatomic Size of the Vas Deferens”, Contraception, 56(6): 391-394 (1997).

Lohiya, N.K. et al., “Preclinical evaluation for noninvasive reversal following long-term vas occlusion with styrene maleic anhydride in langur monkeys”, Contraception, 71(3):214-226 (2005).

Lohiya, N.K., et al., “RISUG: An intravasal injectable male contraceptive”, Indian J Med Res 140 (Supplement): 63-72 (2014).

Lu An, He Hu, Jing Du, Jie Wei, Li Wang, Hong Yang, Dongmei Wu, Haili Shi, Fenghua Li, Shiping Yang, Paramagnetic hollow silica nanospheres for in vivo targeted ultrasound and magnetic resonance imaging, Biomaterials, vol. 35, Issue 20, 2014, pp. 5381-5392.

Mayans, D.; Cartwright, MS.; Walker, F.O. Neuromuscular ultrasonography: Quantifying muscle and nerve measurements. Phys. Med. Rehabil. Clin. N. Am. 2011, 23, 133-148.

Mckay, Craig S., et al., “Click Chemistry in Complex Mixtures: Bioorthogonal Bioconjugation”, Chem Biol. Sep. 18, 2014; 21(9): 1075-1101. doi:10.1016/Lchembiol.2014.09.002., (2014), 51 pgs.

Mehrali, M., Moghaddam, E., Shirazi, S. F. S., Baradaran, S., Mehrali, M., Latibari, S. T. & Osman, N. A. A. (2014). Mechanical and in vitro biological performance of graphene nanoplatelets reinforced calcium silicate composite. PloS one, 9(9), e106802.

Middleton, W.D., et al., “High-Resolution Sonography of the Normal Extrapelvic Vas Deferens”, J Ultrasound Med., 28(7):839-46 (2009).

Naahidi, S. et al. “Biocompatibility of hydrogel-based scaffolds for tissue engineering applications”, Biotechnology Advances, vol. 35, (2017) pp. 530-544.

Naughton, C. K., et al., “The Use of URYX for Reversible Vasectomy in a Rabbit Model”, Journal of Andrology, 25:545-553 (2004).

Noble JA, Boukerroui D. Ultrasound image segmentation: a survey. IEEE Trans Med Imaging. Aug. 2006; 25(8):987-1010.

Norouzi, M., et al. “Injectable hydrogel-based drug delivery systems for local cancer therapy”, Drug Discov. Today, vol. 21, Issue 11, 1835-1849, 2016, 22 pages.

Paefgen V, Doleschel D, Kiessling F. Evolution of contrast agents for ultrasound imaging and ultrasound-mediated drug delivery. Frontiers in Pharmacology. 2015;6:197. doi: 10.3389/fphar.2015.00197.

Qi, Y. et al. “A Review of Structure Construction of Silk Fibroin Biomaterials from Single Structures to Multi-Level Structures”, International Journal of Molecular Sciences, 2017, 18, 237, 21 pages.

Reddy, N. M., et al., “Vasectomy-Related Changes on Sonographic Examination of the Scrotum”, J. Clin. Ultrasound, 32: 394-398 (2004).

Robinette, W.B. “Ultrasound Contrast Agents”, JDMS 13:29S-34S, (1997).

Roy, S. et al., “Polyelectrolyte polymer properties in relation to male contraceptive RISUG® action”, Colloids and Surfaces B: Biointerfaces 69: 77-84 (2009).

Sadtler, K. et al. “Design, clinical translation and immunological response of biomaterials in regenerative medicine,” Nature Reviews Materials, vol. 1, Jul. 2016, 1-17.

Savina, I. et al. “Porous structure and water state in cross-linked polymer and protein cryo-hydrogels”, Soft Matter, 2011, 7, 4276-4283, 8 pages.

Shah, K. et al. “Development and characterization of polyethylene glycol-carbon nanotube hydrogel composite”, J. Mater. Chem. B, 2015, 3, 7950-7962, 13 pages.

Shoskes, J. J. et al. “Pharmacology of testosterone replacement therapy preparations.” Transl Androl Urol. 2016;5(6):834-843, 10 pages.

Singh, Sunilk et al., “Amine-Modified Graphene: Thrombo-Protective Safer Alternative to Graphene Oxide for Biomedical Applications,” Jan. 1, 2012, vol. 6, No. 3, ACS NANO, pp. 3721-2740, XP055417936.

Smith, S. et al. “Carbon-based nanomaterials for removal of chemical and biological contaminants from water: A review of mechanisms and applications”, Carbon 91 (2015), 122-143, 22 pages.

Soebadi, D. M., “Intravasal injection of formed-in-place medical grade silicone for vas occlusion”, International Journal of Andrology, 18: 45-52 (1995).

(56) References Cited

OTHER PUBLICATIONS

Staruch, R. M. T. et al., "Injectable Pore-Forming Hydrogel Scaffolds for Complex Wound Tissue Engineering: Designing and Controlling Their Porosity and Mechanical Properties," Tissue Eng. Part B Rev. 23, 183-198, 2017, 16 pages.
Stockton DM et al. "No-scalpel vasectomy: a technique for family physicians." Am Fam Physician. 1992; 46:1153-67.
Szabo, T.L. et al., "Ultrasound Transducer Selection in Clinical Imaging Practice", Journal of Ultrasound in Medicine, 2013, 32(4):573-582.
Tan, H. and Marra, K. G. "Injectable, Biodegradable Hydrogels for Tissue Engineering Applications", Materials 3, 1746-1767, 2010, 22 pages.
The Encyclopedia of Laser Physics and Technology. Accessed 2017. https://www.rp-photonics.com/encyclopedia.html.
Thyagarajan, K., Ghatak, Ajoy, Lasers: Fundamentals and Applications, Springer US, 2011, ISBN-13:9781441964410.
VenaSeal Closure System, Product Code: VS-402 PT-11348-01 Rev D, Feb. 2015, 24 pages.
Waller et al., "Azoospermia in rabbits following an intravas injection of Vasalgel", Basic and Clinical Andrology, 26:6 (2016).
Waller, D. et al. "Reversibility of Vasalgel male contraceptive in a rabbit model." Basic Clin. Androl. 27, 2017, 9 pages.
Yu, J. et al. In situ covalently cross-linked PEG hydrogel for ocular drug delivery applications, International Journal of Pharmaceutics, 470, 2014, 151-157.
Zambon, J.V., "Efficacy of percutaneous vas occlusion compared with conventional vasectomy", BJU International, 86, 699-706 (2000).
Zhang et al. High strength graphene oxide/polyvinyl alcohol composite hydrogels. J. Mater. Chem., 2011, 21, 10399.
Zhao, S.C., "Intravasal injection of formed-in-place silcone rubber as a method of vas occlusion", International Journal of Andrology, 15:460-464 (1992).
Zhao, S.C., Contraception, "Vas Deferens Occlusion By Percutaneous Injection of Polyurethane Elastomer Plugs: Clinical Experience and Reversibility", 41(5):453-459 (1990).
Co-pending U.S. Appl. No. 17/677,295, Final Office Action dated May 15, 2024, 16 pages.
Co-pending U.S. Appl. No. 17/677,295, Non-Final Office Action dated Jun. 18, 2025, 24 pages.
Co-pending U.S. Appl. No. 17/677,295, Non-Final Office Action, Jan. 8, 2024, 14 pages.
Co-pending U.S. Appl. No. 17/677,295, Non-Final Office Action, Sep. 28, 2022, 20 pages.
Co-pending U.S. Appl. No. 17/677,295, Response to Feb. 16, 2023, Final Office Action dated Aug. 16, 2023, 12 pages.
Co-pending U.S. Appl. No. 17/677,295, Response to Jan. 8, 2024 Non-Final Office Action, dated Apr. 8, 2024, 10 pages.
Co-pending U.S. Appl. No. 17/677,295, Response to Jun. 16, 2022 Restriction Requirement, dated Aug. 16, 2022, 3 pages.
Co-pending U.S. Appl. No. 17/677,295, Response to Jun. 18, 2025 Non-Final Office Action dated Oct. 20, 2025, 9 pages.
Co-pending U.S. Appl. No. 17/677,295, Response to May 15, 2024 Final Office Action, dated Nov. 15, 2024, 11 pages.
Co-pending U.S. Appl. No. 17/677,295, Response to Sep. 28, 2022 Non-Final Office Action, dated Jan. 30, 2023, 9 pages.
Co-pending U.S. Appl. No. 17/677,295, Restriction Requirement dated Jun. 16, 2022, 7 pages.
Co-pending U.S. Appl. No. 17/729,605, filed Apr. 26, 2022, Preliminary Amendment dated Jun. 22, 2022, 7 pages.
Co-pending U.S. Appl. No. 17/729,605, Non-Final Office Action dated Oct. 2, 2023, 11 pages.
Co-pending U.S. Appl. No. 17/729,605, Notice of Allowance dated Jan. 31, 2024, 8 pages.
Co-pending U.S. Appl. No. 17/729,605, Response to May 22, 2023 Restriction Requirement, filed Jun. 23, 2023, 8 pages.
Co-pending U.S. Appl. No. 17/729,605, Response to Oct. 2, 2023 Non-Final Office Action, dated Dec. 21, 2023, 10 pages.
Co-pending U.S. Appl. No. 17/729,605, Restriction Requirement dated May 22, 2023, 7 pages.
Cosgrove D, "Ultrasound contrast agents: An overview", Radiology 2006 vol. 60, Issue 3, pp. 324-330.
Daniels, K. and Abma, J., "Unmarried Men's Contraceptive Use at Recent Sexual Intercourse: United States, 2011-2015", NCHS Data Brief, No. 284, Aug. 2017, U.S. Department of Health and Human Services, 8 pages.
David A. Fulton, "Synthesis: Click chemistry gets reversible" Nature Chemistry 8, 899-900 (2016.).
Dorman, E. et al., "Modeling the impact of novel male contraceptive methods on reductions in unintended pregnancies in Nigeria, South Africa, and the United States", Contraception, Jan. 2018; 97(1): 62-69, 20 pages.
Dressaire, E. et al. "Interfacial Polygonal Nanopatterning of Stable Microbubbles". Science May 30, 2008: vol. 320, Issue 5880, pp. 1198-1201.
El-Sherif, D. M., & Wheatley, M. A. "Development of a novel method for synthesis of a polymeric ultrasound contrast agent", Journal of Biomedical Materials Research Part A, (2003) 66A(2), 347-355.
Fan, H., Wang, L., Zhao, K., Li, N., Shi, Z., Ge, Z., & Jin, Z. (2010). Fabrication, mechanical properties, and biocompatibility of graphene-reinforced chitosan composites. Biomacromolecules, 11(9), 2345-2351.
Flickinger CJ, et al. The influence of vasovasostomy on testicular alterations after vasectomy in lewis rats. Anat Rec, 1987. 217(2): 137-145.
Flickinger CJ. Alterations in the fine structure of the rat epididymis after vasectomy. Anat Rec, 1972. 173(3): 377-300.
Flickinger CJ. Ultrastructure of the rat testis after vasectomy. Anat Rec, 1972. 174(4): 477-493.
Garmiak, R., & Shah, P. M. (1968). Echocardiography of the aortic root. Invest Radiology, 3, 356-366.
Grover, Gregory N. et al. Biocompatible Hydrogels by Oxime Click Chemistry. Biomacromolecules, vol. 13, No. 10, Sep. 12, 2012, pp. 3013-3017. DOI: 10.1021/bm301346e.
Guha, S. K. "Biophysical mechanism-mediated time-dependent effect on sperm of human and monkey vas implanted polyelectrolyte contraceptive." Asian J. Androl. 9, 221-227 (2007), 7 pages.
Guha, S. K. et al., "Phase I clinical trial of an injectable contraceptive for the male", Contraception 1993:48, October, 367-375, 9 pages.
Guha, S.K. et al., "Phase II Clinical Trial of a Vas Deferens Injectable Contraceptive for the Male Contraception", 56:4, 245-250 (1997).
Guimaraes, C. F. et al., "The stiffness of living tissues and its implications for tissue engineering", Nature Reviews Materials, Feb. 21, 2020, 20 pages.
Hafez, Es, et al. "Atlas of Human Reproduction: By Scanning Electron Microscopy", 1982, MTP Press, Hingham, MA. Part 1-1 (separated into 4 parts for Filing), 85 pgs.
Hafez, Es, et al. "Atlas of Human Reproduction: By Scanning Electron Microscopy", 1982, MTP Press, Hingham, MA. Part 1-2 (separated into 4 parts for Filing), 85 pgs.
Hafez, Es, et al. "Atlas of Human Reproduction: By Scanning Electron Microscopy", 1982, MTP Press, Hingham, MA. Part 2-1 (separated into 4 parts for Filing), 66 pgs.
Hafez, Es, et al. "Atlas of Human Reproduction: By Scanning Electron Microscopy", 1982, MTP Press, Hingham, MA. Part 2-2 (separated into 4 parts for Filing), 101 pgs.
Hashemi, E., Akhavan, O., Shamsara, M., Rahighi, R., Esfandiar, A., & Tayefeh, A.R. (2014). Cyto and genotoxicities of graphene oxide and reduced graphene oxide sheets on spermatozoa. RSC Advances, 4(52), 27213-27223.
Hogan, Nora C., Andrew J Taberner, Lynette A Jones & Ian W Hunter (2015) Needle-free delivery of macromolecules through the skin using controllable jet injectors, Expert Opinion on Drug Delivery, 12:10, 1637-1648.
International Application PCT/US19/60985, filed Nov. 12, 2019, International Search Report and Written Opinion dated Apr. 2, 2020, 7 pages.

(56) References Cited

OTHER PUBLICATIONS

International Application PCT/US19/60985, filed Nov. 12, 2019, Invitation to Pay Additional Fees, dated Jan. 30, 2020, 4 pages.
International Application PCT/US2016/061671 filed Nov. 11, 2016, International Search Report and Written Opinion dated Mar. 17, 2017, 29 pages.
International Application PCT/US2016/061671 filed Nov. 11, 2016, Invitation to Pay Additional Fees and Partial Search Report dated Jan. 10, 2017, 2 pages.
ISO 10993-5, "Biological evaluation of medical devices—Part 5: Tests for in vitro cytotoxicity", Third Edition, Jun. 1, 2009, 42 pages.
J. Zhou et al. "Optical Fiber Tips and Their Applications". Polymicro Technologies. Nov. 2007. https://www.molex.com/mx_upload/superfamily/polymicro/pdfs/Optical_Fiber_Tips_and_Their_Applications_Nov_2007.pdf.
Jha, R.K., et al., "Smart Risug: A potential new contraceptive and its magnetic field-mediated sperm interaction", International Journal of Nanomedicine, 4:55-64 (2009).
Kanakis, G. and Goulis, D. "Male contraception: a clinically-oriented review", Hormones 2015, 14(4), 598-614.
Khilwani, B. et al. "RISUG® as a male contraceptive: journey from bench to bedside." Basic Clin. Androl. 30, (2020), 12 pages.
Kihara, K. et al., "A New Method to Generate Canine Seminal Emission and Its Application to Men: Direct Electrical Stimulation of the Vas Deferens", Journal of Andrology, vol. 15, No. 5, Sep./Oct. 1994, 479-483, 5 pages.
Kloxin, A. et al., "Photodegradable hydrogels for dynamic tuning of physical and chemical properties", Science. Apr. 3, 2009; 324(5923): 59-63.
Abbe, C. and Roxby, A., "Assessing Safety in Hormonal Male Contraception: A critical appraisal of adverse events reported in a male contraceptive trial", BMJ Sex Reprod Health Apr. 2020 46(2): 139-146, 15 pages.
Abdala, N. et al., "Use of Ethylene Vinyl Alcohol Copolymer for Tubal Sterilization by Selective Catheterization in Rabbits", Journal of Vascular and Interventional Radiology, 12(8): 979-984 (2001).
Ahmed, Enas M. Hydrogel: Preparation, characterization, and applications: A review, Journal of Advanced Research, vol. 6, Issue 2, 2015, pp. 105-121).
Akbari, A. et al. Large-area graphene-based nanofiltration membranes by shear alignment of discotic nematic liquid crystals of graphene oxide. Nature Communications 7, 10891, 2016, 12 pages.
Akram F, Kim JH, Lee C-G, Choi KN. Segmentation of Regions of Interest Using Active Contours with SPF Function. Comput Math Methods Med. 2015; 2015:e710326.
Amory, J. K. "Development of Novel Male Contraceptives." Clin. Transl. Sci. (2020) 13, 228-237, 10 pages.
Amory, J. K. "Male contraception", Fertility and Sterility, vol. 106, No. 6, Nov. 2016, pp. 1303-1309.
Appel, E. et al. Self-assembled hydrogels utilizing polymer-nanoparticle interactions, Nature Communications, vol. 6, No. 6295, Feb. 19, 2015, 9 pages.
Attaran, R. R, "Protocol for Optimal Detection and Exclusion of a Patent Foramen Ovale Using Transthoracic Echocardiography with Agitated Saline Microbubbles" (2006), Echocardiography (Mount Kisco, N.Y.), 23(7), 616-22.
Avery, R. K. et al. "An injectable shear-thinning biomaterial for endovascular embolization", Sci. Transl. Med., vol. 8, Iss. 365, p. 365ra156, 2016, 13 pages.
Bakaic, E. et al., "Injectable hydrogels based on poly(ethylene glycol) and derivatives as functional biomaterials", RSC Adv 5, 35469-35486, 2015, 50 pages.
Bank et al., "Contribution of Collagen, Elastin, and Smooth Muscle to in Vivo Human Brachial Artery Wall Stress and Elastic Modulus", Circulation. 1996;94:3263-3270.
Bearak, J. et al. "Global, regional, and subregional trends in unintended pregnancy and its outcomes from 1990 to 2014: estimates from a Bayesian hierarchical model", Lancet Glob Health 2018; 6: e380-389, 10 pages.
Behre, H. et al. "Efficacy and Safety of an Injectable Combination Hormonal Contraceptive for Men," J. Clin. Endocrinol. Metab. vol. 101, No. Dec. 12, 2016, pp. 4779-4788.
Bright, Corinne, "Methods and Devices for the Treatmen [sic] of Lung Diseases", U.S. Appl. No. 62/179,027, filed Apr. 27, 2015, 96 pages.
Bustamante-Forest, R. and Giarratano, G., "Changing men's involvement in reproductive health and family planning", Nurs Clin N Am 39 (2004) 301-318, 18 pages.
Calliada F, et al., "Ultrasound contrast agents: basic principles", Eur J Radiol. 1998 27 Suppl 2:S157-60.
Chaki, S.P. et al., "A short-term evaluation of semen and accessory sex gland function in phase III trial subjects receiving intravasal contraceptive RISUG", Contraception, 67(1):73-78 (2003).
Chao, J. H. and Page, S. T., "The current state of Male hormonal contraception", Pharmacology and Therapeutics (2016), 42 pages.
Clenney TL, "Vasectomy Techniques," Am Fam Physician. 1999; 60(1):137-146.
Colagross-Schouten, A., et al., "The contraceptive efficacy of intravas injection of Vasalgel for adult male rhesus monkeys." Basic Clin. Androl. 27, 4, 2017, 7 pages.
Co-pending U.S. Appl. No. 15/349,824, Amendment After Allowance dated Sep. 27, 2018 and Acceptance of Same, 5 pages.
Co-pending U.S. Appl. No. 15/349,824, Final Office Action dated Aug. 2, 2017, 17 pages.
Co-pending U.S. Appl. No. 15/349,824, Interview Summary, dated Dec. 13, 2017, 3 pages.
Co-pending U.S. Appl. No. 15/349,824, Non-Final Office Action dated Jan. 26, 2017, 12 pages.
Co-pending U.S. Appl. No. 15/349,824, Non-Final Office Action dated Feb. 7, 2018, 13 pages.
Co-pending U.S. Appl. No. 15/349,824, Notice of Allowance dated Aug. 15, 2018, 10 pages.
Co-pending U.S. Appl. No. 15/349,824, RCE filed in response to Aug. 2, 2017 Final Office Action, dated Oct. 6, 2017, 18 pages.
Co-pending U.S. Appl. No. 15/349,824, Response to Jan. 26, 2017 Non-Final Office Action dated Apr. 26, 2017, 17 pages.
Co-pending U.S. Appl. No. 15/349,824, Response to Feb. 7, 2018 Non-Final Office Action dated May 7, 2018, 14 pages.
Co-pending U.S. Appl. No. 15/349,824, Supplemental Amendment, dated Dec. 27, 2017, 10 pages.
Co-pending U.S. Appl. No. 16/681,572, Corrected Notice of Allowance, dated Jan. 12, 2022, 5 pages.
Co-pending U.S. Appl. No. 16/681,572, Non-Final Office Action dated Oct. 4, 2021, 12 pages.
Co-pending U.S. Appl. No. 16/681,572, Notice of Allowance, dated Jan. 3, 2022, 8 pages.
Co-pending U.S. Appl. No. 16/681,572, Preliminary Amendment dated Nov. 12, 2019, 9 pages.
Co-pending U.S. Appl. No. 16/681,572, Response to Oct. 4, 2021 Non-Final Office Action, dated Nov. 11, 2021, 9 pages.
Co-pending U.S. Appl. No. 17/358,501, Final Office Action dated Dec. 4, 2023, 24 pages.
Co-pending U.S. Appl. No. 17/358,501, Non-Final Office Action dated Jun. 7, 2023, 21 pages.
Co-pending U.S. Appl. No. 17/358,501, Non-Final Office Action dated May 14, 2024, 29 pages.
Co-pending U.S. Appl. No. 17/358,501, Response to Dec. 4, 2023 Final Office Action, dated May 6, 2024, 7 pages.
Co-pending U.S. Appl. No. 17/358,501, Response to Jun. 7, 2023 Non-Final Office Action, dated Sep. 7, 2023, 7 pages.
Co-pending U.S. Appl. No. 17/358,501, Response to Nov. 4, 2022 Restriction Requirement, dated May 4, 2023, 2 pages.
Co-pending U.S. Appl. No. 17/358,501, Restriction Requirement dated Nov. 4, 2022, 7 pages.
Co-pending U.S. Appl. No. 17/584,046, Non-Final Office Action dated Mar. 31, 2022, 8 pages.
Co-pending U.S. Appl. No. 17/584,046, Notice of Allowance dated Jul. 29, 2022, 8 pages.
Co-pending U.S. Appl. No. 17/584,046, Response to Mar. 31, 2022 Non-Final Office Action dated Jun. 27, 2022, 8 pages.
Co-pending U.S. Appl. No. 17/974,264, Non-Final Office Action dated Aug. 17, 2023, 8 pages.

(56) References Cited

OTHER PUBLICATIONS

Co-pending U.S. Appl. No. 17/974,264, Non-Final Office Action dated Aug. 29, 2023, 7 pages.
Co-pending U.S. Appl. No. 17/974,264, Notice of Allowance dated Dec. 26, 2023, 8 pages.
Co-pending U.S. Appl. No. 17/974,264, Preliminary Amendment dated Feb. 9, 2023, 6 pages.
Co-pending U.S. Appl. No. 15/863,759 Notice of allowance dated Jun. 30, 2020, 7 pages.
Co-pending U.S. Appl. No. 15/863,759 Notice of allowance dated Sep. 16, 2019.
Co-pending U.S. Appl. No. 15/863,759 Response to Jun. 2, 2020 Non-Final Office Action, filed Jun. 15, 2020, 6 pages.
Co-pending U.S. Appl. No. 15/863,759, Final Office Action dated Nov. 2, 2018, 14 pages.
Co-pending U.S. Appl. No. 15/863,759, Final Office Action dated Nov. 2, 2018, 45 pages.
Co-pending U.S. Appl. No. 15/863,759, Non-Final Office Action dated Apr. 18, 2019, 20 pages.
Co-pending U.S. Appl. No. 15/863,759, Non-Final Office Action dated Apr. 3, 2018, 12 pages.
Co-pending U.S. Appl. No. 15/863,759, Non-Final Office Action, dated Jun. 2, 2020, 11 pages.
Co-pending U.S. Appl. No. 15/863,759, RCE and Response to Final Office Action filed Feb. 22, 2019, 12 pages.
Co-pending U.S. Appl. No. 15/863,759, Response to Apr. 18, 2019 Non-Final Office Action dated Jul. 17, 2019, 8 pages.
Co-pending U.S. Appl. No. 15/863,759, Response to Apr. 3, 2018 Non-Final Office Action dated Jul. 3, 2018, 14 pages.
Co-pending U.S. Appl. No. 16/104,701, Non-Final Office Action dated Mar. 26, 2021, 38 pages.
Co-pending U.S. Appl. No. 16/104,701, Non-Final Office Action dated Oct. 30, 2020, 25 pages.
Co-pending U.S. Appl. No. 16/104,701, Response to Oct. 30, 2020 Non-Final Office Action dated Mar. 1, 2021, 14 pages.
Co-pending U.S. Appl. No. 16/104,701, Response to Sep. 8, 2020 Restriction Requirement dated Oct. 14, 2020, 11 pages.
Co-pending U.S. Appl. No. 16/104,701, Restriction Requirement dated Sep. 8, 2020, 7 pages.
Co-pending U.S. Appl. No. 16/156,947, Advisory Action dated Oct. 27, 2022, 3 pages.
Co-pending U.S. Appl. No. 16/156,947, Amendment after Notice of Allowance, dated May 12, 2025, 5 pages.
Co-pending U.S. Appl. No. 16/156,947, Examiner Interview Summary dated Mar. 12, 2025, 2 pages.
Co-pending U.S. Appl. No. 16/156,947, Final Office Action dated Jul. 5, 2024, 14 pages.
Co-pending U.S. Appl. No. 16/156,947, Final Office Action dated Jun. 26, 2023, 13 pages.
Co-pending U.S. Appl. No. 16/156,947, Final Office Action dated May 19, 2022, 12 pages.
Co-pending U.S. Appl. No. 16/156,947, Interview Summary dated Jun. 11, 2024, 2 pages.
Co-pending U.S. Appl. No. 16/156,947, Non-Final Office Action dated Aug. 5, 2021, 11 pages.
Co-pending U.S. Appl. No. 16/156,947, Non-Final Office Action dated Dec. 21, 2023, 8 pages.
Co-pending U.S. Appl. No. 16/156,947, Non-Final Office Action dated Dec. 9, 2022, 11 pages.
Co-pending U.S. Appl. No. 16/156,947, Non-Final Office Action dated Oct. 24, 2024, 15 pages.
Co-pending U.S. Appl. No. 16/156,947, Notice of Allowance dated Oct. 24, 2024, 15 pages.
Co-pending U.S. Appl. No. 16/156,947, Preliminary Amendment filed Sep. 27, 2019, 10 pages.
Co-pending U.S. Appl. No. 16/156,947, Response to Amendment Under Rule 312, dated May 19, 2025, 8 pages.
Co-pending U.S. Appl. No. 16/156,947, Response to Apr. 5, 2021 Restriction Requirement dated Apr. 28, 2021, 10 pages.
Co-pending U.S. Appl. No. 16/156,947, Response to Aug. 5, 2021 Non-Final Office Action, filed Jan. 31, 2022, 11 pages.
Co-pending U.S. Appl. No. 16/156,947, Response to Dec. 21, 2023 Non-Final Office Action, dated Mar. 21, 2024, 6 pages.
Co-pending U.S. Appl. No. 16/156,947, Response to Dec. 9, 2022 Non-Final Office Action, dated Mar. 9, 2023, 7 pages.
Co-pending U.S. Appl. No. 16/156,947, Response to Jul. 5, 2024 Final Office Action, dated Oct. 7, 2024, 7 pages.
Co-pending U.S. Appl. No. 16/156,947, Response to Jun. 26, 2023 Final Office Action, dated Nov. 22, 2023, 7 pages.
Co-pending U.S. Appl. No. 16/156,947, Response to May 19, 2022 Final Office Action, Sep. 12, 2022, 3 pages.
Co-pending U.S. Appl. No. 16/156,947, Response to Oct. 24, 2024 Non-Final Office Action and Rule 132 affidavit, dated Jan. 24, 2025, 10 pages.
Co-pending U.S. Appl. No. 16/156,947, Response to Oct. 27, 2022 Advisory Action, dated Nov. 15, 2022, 5 pages.
Co-pending U.S. Appl. No. 16/156,947, Restriction Requirement dated Apr. 5, 2021, 8 pages.
Co-pending U.S. Appl. No. 16/681,577, Interview Summary dated Jan. 14, 2022, 2 pages.
Co-pending U.S. Appl. No. 16/681,577, Interview Summary for Feb. 18, 2022 interview, 2 pages.
Co-pending U.S. Appl. No. 16/681,577, Non-Final Office Action dated Nov. 9, 2021, 13 pages.
Co-pending U.S. Appl. No. 16/681,577, Notice of Allowance dated Mar. 10, 2022, 11 pages.
Co-pending U.S. Appl. No. 16/681,577, Preliminary Amendment, filed Nov. 12, 2019, 9 pages.
Co-pending U.S. Appl. No. 16/681,577, Response to Jun. 23, 2021 Restriction Requirement, filed Jul. 30, 2021, 9 pages.
Co-pending U.S. Appl. No. 16/681,577, Response to Nov. 9, 2021 Non-Final Office Action, filed Feb. 8, 2022, 13 pages.
Co-pending U.S. Appl. No. 16/681,577, Restriction Requirement dated Jun. 23, 2021, 6 pages.
Co-pending U.S. Appl. No. 17/677,295, Final Office Action dated Dec. 2, 2025, 22 pages.
Co-pending U.S. Appl. No. 17/677,295, Final Office Action dated Feb. 16, 2023, 9 pages.
"Plug, socket & voltage by country". World Standards. At least as early as Oct. 2, 2017. http://www.worldstandards.eu/electricity/plug-voltage-by-country/.
"Silica Fibers". RP Photonics Encyclopedia. At least as early as Oct. 2, 2017. https://www.rp-photonics.com/silica_fibers.html.
"Syringe Needle Gauge Chart". Sigma Aldrich. At least as early as Oct. 2, 2017. http://www.sigmaaldrich.com/chemistry/stockroom-reagents/learning-center/technicallibrary/needle-gauge-chart.html.
(Eisenfrats, Kevin et al.) Co-pending Australian Patent Application, published as AU2016353345 on Jun. 14, 2018 (see WO2017083753), Specification, Claims, Figures.
(Eisenfrats, Kevin et al.) Co-pending European Patent Application No. 17183620.8, filed Jul. 27, 2017, published as EP3275469 on Jan. 31, 2018, Specification, Claims, Figures.
(Eisenfrats, Kevin et al.) Co-pending International Application No. PCT/US18/53853, filed Oct. 2, 2018, Specification, Claims, Figures (see WO 2019/070632).
(Eisenfrats, Kevin et al.) Co-Pending International Application No. PCT/US2021/032235, filed May 13, 2021, Specification, Claims, Figures, 85 pages.
(Eisenfrats, Kevin et al.) Co-pending International Application No. PCT/US24/54249, filed Nov. 1, 2024, Specification, Claims, Figures.
(Eisenfrats, Kevin et al.) Co-pending U.S. Appl. No. 16/753,302 filed Apr. 2, 2020, specification, claims, figures.
(Eisenfrats, Kevin et al.) Co-pending U.S. Appl. No. 16/927,614, filed Jul. 13, 2020, Specification, Claims, Figures.
(Eisenfrats, Kevin et al.) Co-pending U.S. Appl. No. 15/653,618, filed Jul. 19, 2017, published as US 20180028715 on Feb. 1, 2018, specification, claims, figures.
(Eisenfrats, Kevin et al.) Co-pending U.S. Appl. No. 15/863,759, filed Jan. 5, 2018, published as US 20180185096 on Jul. 5, 2018, Specification, Claims, Figures.

(56) References Cited

OTHER PUBLICATIONS (Eisenfrats, Kevin et al.) Co-pending U.S. Appl. No. 16/156,947, filed Oct. 10, 2018, Specification, Claims, Figures.
(Eisenfrats, Kevin et al.) Co-pending U.S. Appl. No. 19/296,839, filed Aug. 11, 2025, Specification, Claims, Figures.
(Grover, Greg et al.) Co-pending Australian Patent Application No. 2018205258, Official Filing Date Jan. 5, 2018, Specification, Claims, Figures (see PCT/US2018/012654).
(Grover, Greg et al.) Co-pending Australian Patent Application No. 2019380413, filed Apr. 17, 2021, Specification, Claims, Figures (See WO2020/102234A1).
(Grover, Greg et al.) Co-pending Australian Patent Application No. 2023270305, Filed Nov. 23, 2023, Specification, Claims, Figures, 73 pages.
(Grover, Greg et al.) Co-pending Canadian Patent Application No. 3,078,365, Official Filing Date Apr. 2, 2020 (see PCT/US18/53853), Specification, Claims, Figures.
(Grover, Greg et al.) Co-pending Canadian Patent Application No. 3053451, Official Filing Date Jan. 5, 2018 (see PCT/US2018/012654), Specification, Claims, Figures.
(Grover, Greg et al.) Co-pending China Patent Application No. 201880015144.0, Official Filing Date Jan. 5, 2018, Specification, Claims, Figures (see PCT/US2018/012654), and which published as CN110381854A on Oct. 25, 2019.
(Grover, Greg et al.) Co-pending China Patent Application No. CN 201880078000.X, Official Filing Date Apr. 2, 2020 (see PCT/US18/53853 for English Version), Specification, Claims, Figures.
(Grover, Greg et al.) Co-pending European Patent Application No. 18736340.3, Official filing date Jan. 5, 2018, and which published as EP3565484 on Nov. 13, 2019, Specification, Claims, Figures (see PCT/US2018/012654).
(Grover, Greg et al.) Co-pending European Patent Application No. 24166850.8, Filed Mar. 27, 2024, and which published as EP4400166 on Jul. 17, 2024, Specification, Claims, and Figures.
(Grover, Greg et al.) Co-pending International Application No. PCT/US18/12654, filed Jan. 5, 2018, Specification, Claims, Figures.
(Grover, Gregory et al.) Co-pending U.S. Appl. No. 16/681,572, filed Nov. 12, 2019, Specification, Claims, and Figures.
(Grover, Gregory et al.) Co-pending U.S. Appl. No. 17/584,046, filed Jan. 25, 2022, Specification, Claims, Figures.
(Grover, Gregory et al.) Co-pending U.S. Appl. No. 17/974,264, filed Oct. 26, 2022, Specification, Claims, Figures.
(Grover, Gregory et al.) Co-Pending Canadian Application No. 3117577, filed Nov. 12, 2019, Specification, Claims, Figures (See WO2020102234A1).
(Grover, Gregory et al.) Co-Pending European Application No. 19883448.3, filed Apr. 22, 2021, Specification, Claims, Figures (See WO2020102234A1).
(Grover, Gregory et al.) Co-pending International Application No. PCT/US20/47642, filed Aug. 24, 2020, Specification, Claims, Figures.
(Grover, Gregory et al.) Co-Pending International Application No. PCT/US2021/034562, filed May 27, 2021, Specification, Claims, Figures, 60 pages.
(Grover, Gregory et al.) Co-Pending Japan Application No. JP2021523237, filed Nov. 12, 2019, Specification, Claims, Figures (See WO2020102234A1).
(Grover, Gregory et al.) Co-pending U.S. Appl. No. 16/104,701, filed Aug. 17, 2018, Specification, Claims, Figures.
(Grover, Gregory et al.) Co-pending U.S. Appl. No. 16/681,577, filed Nov. 12, 2019, Specification, Claims, Figures.
(Grover, Gregory et al.) Co-pending U.S. Appl. No. 17/358,501, filed Jun. 25, 2021, Specification, Claims, Figures.
(Grover, Gregory et al.) Co-pending U.S. Appl. No. 17/677,295, filed Feb. 22, 2022, Specification, Claims, Figures.
(Grover, Gregory et al.) Co-pending U.S. Appl. No. 17/729,605, filed Apr. 26, 2022, Specification, Claims, Figures.
(Herr, John C. et al.) Co-pending Australian Patent Application No. 2021277608, filed Nov. 29, 2021, Specification, Claims, Figures, 124 pages.
(Herr, John C. et al.) Co-pending Australian Patent Application No. 2024200036, filed Jan. 3, 2024, Specification, Claims, Figures, 148 pages.
(Herr, John et al.) Co-pending U.S. Appl. No. 15/349,824, filed Nov. 11, 2016, published as US 20170136143 on May 18, 2017, Specification, Claims, Figures.
(Herr, John et al.) Co-pending Canada Patent Application, filed May 8, 2018, published as CA3004745 on May 18, 2017 (see WO2017083753), Specification, Claims, Figures.
(Herr, John et al.) Co-pending European Patent Application No. 16865154.5, filed May 23, 2018, published as EP3383870 on Sep. 19, 2018, amended claims, (for Specification and Figures see WO2017083753).
(Herr, John et al.) Co-pending International Application PCT/US2016/061671 filed Nov. 11, 2016, published as WO/2017/083753 on May 18, 2017, Specification, Claims, Figures.
(Herr, John et al.) Co-pending U.S. Appl. No. 15/349,806, filed Nov. 11, 2016, published as US 20170136144 on May 18, 2017, Specification, Claims, Figures.
(Herr, John et al.) Co-pending U.S. Appl. No. 16/173,539, filed Oct. 29, 2018, published as US 2019-0060513 A1 on Feb. 28, 2019, Specification, Claims, Figures.
(Herr, John et al.) Co-pending U.S. Appl. No. 17/651,509, filed Feb. 17, 2022, Specification, Claims, Figures.
(Herr, John et al.) Co-pending U.S. Appl. No. 18/400,466, filed Dec. 29, 2023, Specification, Claims, Figures.
(Tropsha, Yelena et al.) Co-pending U.S. Appl. No. 19/122,856, filed Apr. 21, 2025, Specification, Claims, and Figures.
(Tropsha, Yelena et al.) Co-pending International Application No. PCT/US23/77473, filed Oct. 20, 2023, Specification, Claims, and Figures, 43 pages.
414093 Sigma-Aldrich Product Safety Data Sheet ("poly(vinyl alcohol coethylene) with ethylene 32 mol %"). Version 4.2. Revision Date: Jun. 25, 2014. Print Date: Mar. 27, 2017.
Co-Pending European Application No. 19883448.3, Extended European Search Report dated Jul. 2, 2022, 12 pages.
Co-Pending European Application No. 19883448.3, Response to European Search Report filed Feb. 7, 2023, 193 pages.
Co-Pending European Application No. 19883448.3, Response to Mar. 24, 2025 Communication pursuant to Article 94(3) EPC, dated Jul. 23, 2025, 13 pages.
Co-pending European Patent Application No. 16865154.5, Communication Pursuant to Article 94 (3) EPC, dated Mar. 26, 2024, 11 pages.
Co-pending European Patent Application No. 16865154.5, Communication Pursuant to Rule 94(3), dated Aug. 3, 2021, 11 pages.
Co-pending European Patent Application No. 16865154.5, Communication Pursuant to Rule 94(3), dated Feb. 26, 2020, 11 pages.
Co-pending European Patent Application No. 16865154.5, Communication Under Rules 70(2) and 70a(2), Jun. 26, 2019, 1 page.
Co-pending European Patent Application No. 16865154.5, Corrected Response to Feb. 26, 2020 Communication Pursuant to Rule 94(3), filed Jun. 26, 2020, 12 pages.
Co-pending European Patent Application No. 16865154.5, Response to Aug. 3, 2021 Communication Pursuant to Rule 94(3), dated Feb. 1, 2022, 159 pages.
Co-pending European Patent Application No. 16865154.5, Response to Feb. 26, 2020 Communication Pursuant to Rule 94(3), filed Jun. 23, 2020, 17 pages.
Co-pending European Patent Application No. 16865154.5, Response to Jun. 26, 2019 Communication Under Rules 70(2) and 70a(2), filed Dec. 20, 2019, 18 pages.
Co-pending European Patent Application No. 16865154.5, Response to Mar. 26, 2024 Communication Pursuant to Article 94(3) EPC, dated Sep. 25, 2024, 96 pages.
Co-pending European Patent Application No. 16865154.5, Search Report and Written Opinion, Jun. 6, 2019, 9 pages.
Co-pending European Patent Application No. 16865154.5, Voluntary Amendment, filed Dec. 20, 2018, 10 pages.
Co-pending European Patent Application No. 17183620.8, Response to Jul. 23, 2020 94(3) EPC Communication dated Dec. 1, 2020, 49 pages.

(56) References Cited

OTHER PUBLICATIONS

Co-pending European Patent Application No. 17183620.8, Communication Pursuant to Article 94(3) EPC, dated Apr. 14, 2025, 4 pages.
Co-pending European Patent Application No. 17183620.8, Communication Pursuant to Article 94(3) EPC, dated Dec. 14, 2022, 4 pages.
Co-pending European Patent Application No. 17183620.8, Communication Pursuant to Article 94(3) EPC, dated Jul. 23, 2020, 4 pages.
Co-pending European Patent Application No. 17183620.8, Extended European Search Report dated Nov. 6, 2017, 6 pages.
Co-pending European Patent Application No. 17183620.8, Response to Dec. 14, 2022 Communication Pursuant to Article 94(3) EPC, filed Jun. 26, 2023, 124 pages.
Co-pending European Patent Application No. 17183620.8, Response to Extended European Search Report dated Jul. 31, 2018, 16 pages.
Co-pending European Patent Application No. 17183620.8, Extended European Search Report dated Nov. 6, 2017, 8 pages.
Co-pending European Patent Application No. 18736340.3, Communication Pursuant to Article 94(3) EPC dated Mar. 11, 2021, 7 pages.
Co-pending European Patent Application No. 18736340.3, Communication Pursuant to Rules 161(2) and 162 EPC, dated Aug. 21, 2019, 3 pages.
Co-pending European Patent Application No. 18736340.3, Communication Pursuant to Rules 70(2) and 70a(2) EPC, dated May 12, 2020, 1 page.
Co-pending European Patent Application No. 18736340.3, Extended European Search Report and Opinion, dated Apr. 23, 2020, 15 pages.
Co-pending European Patent Application No. 18736340.3, Intention to Grant dated Aug. 25, 2023, 93 pages.
Co-pending European Patent Application No. 18736340.3, Response to May 12, 2020 Rules 70(2) and 70a(2) EPC, dated Nov. 23, 2020, 17 pages.
Co-pending European Patent Application No. 18736340.3, Response to Aug. 21, 2019 Communication Pursuant to Rules 161(2) and 162 EPC, filed Feb. 28, 2020.
Co-pending European Patent Application No. 18736340.3, Response to Mar. 11, 2021 Communication Pursuant to Article 94(3) EPC dated Jul. 21, 2021, 90 pages.
Co-pending European Patent Application No. 18736340.3, Response to Mar. 14, 2023 Communication under Rule 71(3) EPC, dated Jul. 26, 2023, 12 pages.
Co-pending European Patent Application No. 24166850.8, Extended European Search Report and Written Opinion dated Dec. 23, 2024, 10 pages.
Co-pending International Application No. PCT/US18/53853, Search Report and Written Opinion, dated Dec. 13, 2018, 16 pages.
Co-pending International Application No. PCT/US19/60985 (WO2020/102234), International Search Report, dated Apr. 2, 2020, 5 pages.
Co-pending International Application No. PCT/US20/47642, ISR dated Jan. 5, 2021, 4 pages.
Co-pending International Application No. PCT/US20/47642, Written Opinion, dated Jan. 5, 2021, 6 pages.
Co-Pending International Application No. PCT/US2021/032235, International Search Report and Written Opinion dated Sep. 28, 2021, 14 pages.
Co-Pending International Application No. PCT/US2021/032235, Invitation to Pay Additional Fees dated Jul. 6, 2021, 3 pages.
Co-Pending International Application No. PCT/US2021/034562, International Search Report and Written Opinion dated Oct. 6, 2021, 15 pages.
Co-pending International Application No. PCT/US23/77473, International Search Report and Written Opinion dated Apr. 2, 2024, 20 pages.
Co-pending International Application No. PCT/US23/77473, Invitation to Pay Additional Fees dated Jan. 17, 2024, 2 pages.
Co-pending International Application No. PCT/US24/54249, International Search Report and Written Opinion dated Mar. 14, 2025, 13 pages.
Co-pending International Application PCT/US2016/061671 International Preliminary Report on Patentability, May 24, 2018, 26 pages.
Co-pending International Application PCT/US2016/061671 International Search Report dated Mar. 17, 2017, 5 pages.
Co-pending International Application PCT/US2016/061671 Invitation to Pay Additional Fees dated Jan. 10, 2017, 2 pages.
Co-pending International Application PCT/US2018/012654 (WO/2017/083753), International Search Report and Written Opinion, Mar. 26, 2018, 22 pages.
Co-Pending Japan Application No. JP2021523237, Reasons for Refusal dated Mar. 25, 2024, 3 pages, and English Translation, 3 pages.
Co-Pending Japan Application No. JP2021523237, Reasons for Refusal dated Sep. 21, 2023, 4 pages, and English Translation, 4 pages.
Co-Pending Japan Application No. JP2021523237, Response to Mar. 25, 2024 Reasons for Refusal, filed Jun. 27, 2024, 5 pages, and English Translation, 6 pages.
Co-Pending Japan Application No. JP2021523237, Response to Sep. 21, 2023 Reasons for Refusal, filed Dec. 25, 2023, 8 pages, and English Translation, 7 pages.
Co-pending U.S. Appl. No. 17/974,264, Response to Aug. 29, 2023 Non-Final Office Action, dated Nov. 13, 2023, 2 pages.
Co-pending U.S. Appl. No. 19/122,856, Preliminary amendment dated Apr. 21, 2025, 6 pages.
Co-pending Australian Patent Application No. 2018205258, Amendment dated May 10, 2022, 20 pages.
Co-pending Australian Patent Application No. 2018205258, Examination Report No. 1, dated Aug. 31, 2022, 2 pages.
Co-pending Australian Patent Application No. 2018205258, Notice of Acceptance with claims and description as accepted, dated Aug. 10, 2023, 56 pages.
Co-pending Australian Patent Application No. 2018205258, Response to Examination Report No. 1, dated Jul. 31, 2023, 2 pages.
Co-pending Australian Patent Application No. 2019380413, Claims as Accepted, dated Oct. 10, 2023, 6 pages.
Co-pending Australian Patent Application No. 2019380413, Examination Report No. 1, dated Aug. 30, 2024, 3 pages.
Co-pending Australian Patent Application No. 2021277608, Examination Report No. 1, dated Oct. 19, 2022, 4 pages.
Co-pending Australian Patent Application No. 2021277608, Notice of Acceptance dated Sep. 25, 2023, 7 pages.
Co-pending Australian Patent Application No. 2021277608, Response to Examination Report No. 1, dated Sep. 12, 2023, 29 pages.
Co-pending Australian Patent Application No. 2023270305, Exam Report dated Apr. 14, 2025, 8 pages.
Co-pending Australian Patent Application No. 2024200036, First Examination Report dated Dec. 9, 2024, 3 pages.
Co-pending Australian Patent Application No. 2024200036, Notice of Acceptance dated Dec. 4, 2025, 3 pages.
Co-pending Australian Patent Application No. 2024200036, Response to First Examination Report dated Mar. 7, 2025, 39 pages.
Co-pending Australian Patent Application No. 2024200036, Response to Second Examination Report, dated Oct. 30, 2025, 15 pages.
Co-pending Australian Patent Application No. 2024200036, Response to Third Examination Report dated Nov. 24, 2025, 11 pages.
Co-pending Australian Patent Application No. 2024200036, Second Examination Report dated Mar. 25, 2025, 4 pages.
Co-pending Australian Patent Application No. 2024200036, Third Examination Report dated Nov. 11, 2025, 5 pages.
Co-pending Australian Patent Application No. AU2016353345, Claims as Accepted, dated Nov. 25, 2021, 4 pages.
Co-pending Australian Patent Application No. AU2016353345, First Examination Report dated Jan. 15, 2021, 7 pages.
Co-pending Australian Patent Application No. AU2016353345, Notice of Acceptance, dated Dec. 8, 2021, 3 pages.
Co-pending Australian Patent Application No. AU2016353345, Response to First Examination Report, filed Aug. 31, 2021, 113 pages.

(56) References Cited

OTHER PUBLICATIONS

Co-pending Australian Patent Application No. AU2016353345, Response to Second Examination Report, dated Nov. 25, 2021, 13 pages.
Co-pending Australian Patent Application No. AU2016353345, Second Examination Report dated Sep. 9, 2021, 5 pages.
Co-pending Canada Patent Application No. 3004745, Examiner Requisition dated Dec. 18, 2025, 5 pages.
Co-pending Canada Patent Application No. 3004745, Examiner Requisition dated Jan. 13, 2023, 7 pages.
Co-pending Canada Patent Application No. 3004745, Examiner Requisition dated Mar. 1, 2024, 9 pages.
Co-pending Canada Patent Application No. 3004745, Response to Jan. 13, 2023 Examiner Requisition, filed May 15, 2023, 131 pages.
Co-pending Canada Patent Application No. 3004745, Response to Mar. 1, 2024 Examiner Requisition, dated Jul. 2, 2024, 20 pages.
Co-Pending Canadian Application No. 3117577, Examiner Requisition dated Apr. 17, 2025, 5 pages.
Co-Pending Canadian Application No. 3117577, Response to Apr. 17, 2025 Examiner Requisition, dated Aug. 15, 2025, 17 pages.
Co-Pending Canadian Application No. 3117577, Voluntary Amendment dated Oct. 18, 2023, 25 pages.
Co-pending Canadian Patent Application No. 3053451, Examiner Requisition dated Jul. 10, 2025, 9 pages.
Co-pending Canadian Patent Application No. 3053451, Examiner Requisition dated May 2, 2024, 3 pages.
Co-pending Canadian Patent Application No. 3053451, Request for Examination with Voluntary Amendment dated Jan. 5, 2023, 4 pages.
Co-pending Canadian Patent Application No. 3053451, Response to May 2, 2024 Examiner Requisition, dated Aug. 30, 2024, 2 pages.
Co-pending Chinese Application No. CN 201880078000.X, First Office Action dated Sep. 27, 2024, 6 pages (with English translation, 14 pages).
Co-pending Chinese Application No. CN 201880078000.X, Initiative Amendment filed Jan. 29, 2021, 19 pages (with English version of the claims, 9 pages).
Co-pending Chinese Patent Application No. 201880015144.0, Amendment as filed Jan. 3, 2020 (with english version of the claims).
Co-pending Chinese Patent Application No. 201880015144.0, First Office Action dated Mar. 3, 2022 (6 pages) and English Translation (5 pages).
Co-pending Chinese Patent Application No. 201880015144.0, Fourth Office Action dated Sep. 25, 2023 (8 pages) and English Translation (13 pages).
Co-pending Chinese Patent Application No. 201880015144.0, Response to Dec. 21, 2022 Office Action, dated May 4, 2023 (14 pages) and English Translation of the amended claims (5 pages).
Co-pending Chinese Patent Application No. 201880015144.0, Response to Mar. 3, 2022 First Office Action, dated Sep. 16, 2022 (11 pages) and English Translation of Amended Claims (6 pages).
Co-pending Chinese Patent Application No. 201880015144.0, Response to Third Office Action, dated Aug. 17, 2023 (11 pages) and English Translation of the Amended Claims (5 pages).
Co-pending Chinese Patent Application No. 201880015144.0, Search Report dated Jun. 12, 2023, 3 pages.
Co-pending Chinese Patent Application No. 201880015144.0, Second Office Action dated Dec. 21, 2022 (4 pages) and English Translation (5 pages).
Co-pending Chinese Patent Application No. 201880015144.0, Third Office Action dated Jun. 13, 2023 (7 pages) and English Translation (12 pages).
Co-Pending European Application No. 19883448.3, Amended Claims filed Dec. 15, 2021, 25 pages.
Co-Pending European Application No. 19883448.3, Communication pursuant to Article 94(3) EPC dated Mar. 24, 2025, 9 pages.
Co-Pending Japan Application No. JP2021523237, Search Report dated Sep. 29, 2023, 26 pages, and English Translation, 32 pages.
Co-pending U.S. Appl. No. 15/349,806, Non-Final Office Action dated Aug. 22, 2017, 14 pages.
Co-pending U.S. Appl. No. 15/349,806, Non-Final Office Action dated Feb. 24, 2017, 9 pages.
Co-pending U.S. Appl. No. 15/349,806, Response to Feb. 24, 2017 Non-Final Office Action dated May 23, 2017,14 pages.
Co-pending U.S. Appl. No. 16/173,539, Non-Final Office Action dated Apr. 27, 2021, 11 pages.
Co-pending U.S. Appl. No. 16/173,539, Notice of Allowance dated Nov. 10, 2021, 8 pages.
Co-pending U.S. Appl. No. 16/173,539, Response to Apr. 27, 2021 Non-Final Office Action filed Jul. 27, 2021, 110 pages.
Co-pending U.S. Appl. No. 16/173,539, USPTO Communication dated Feb. 14, 2022, 2 pages.
Co-pending U.S. Appl. No. 16/753,302 Preliminary Amendment, filed Apr. 2, 2020, 8 pages.
Co-pending U.S. Appl. No. 16/753,302, Final Office Action dated Nov. 14, 2022, 16 pages.
Co-pending U.S. Appl. No. 16/753,302, Non-Final Office Action dated Apr. 25, 2022, 14 pages.
Co-pending U.S. Appl. No. 16/753,302, Response to Apr. 25, 2022 Non-Final Office Action, dated Oct. 25, 2022, 12 pages.
Co-pending U.S. Appl. No. 16/927,614, Final Office Action dated Jun. 21, 2024, 12 pages.
Co-pending U.S. Appl. No. 16/927,614, Non-Final Office Action dated Sep. 14, 2023, 16 pages.
Co-pending U.S. Appl. No. 16/927,614, Notice to file Corrected Application Papers dated Jul. 23, 2020, 2 pages.
Co-pending U.S. Appl. No. 16/927,614, Response to Jul. 23, 2020 NTFCAP, filed Aug. 3, 2020, 14 pages.
Co-pending U.S. Appl. No. 16/927,614, Response to May 25, 2023 Restriction Requirement, dated Aug. 3, 2023, 11 pages.
Co-pending U.S. Appl. No. 16/927,614, Response to Sep. 14, 2023 Non-Final Office Action, dated Mar. 14, 2024, 12 pages.
Co-pending U.S. Appl. No. 16/927,614, Restriction Requirement dated May 25, 2023, 8 pages.
Co-pending U.S. Appl. No. 17/651,509, Non-Final Office Action dated Jun. 8, 2023, 9 pages.
Co-pending U.S. Appl. No. 17/651,509, Notice of Allowance dated Sep. 28, 2023, 8 pages.
Co-pending U.S. Appl. No. 17/651,509, Preliminary amendment dated Jan. 31, 2023, 6 pages.
Co-pending U.S. Appl. No. 17/651,509, Response to Jun. 8, 2023 Non-Final Office Action, dated Sep. 8, 2023, 5 pages.
Co-pending U.S. Appl. No. 18/400,466 Ex Parte Quayle Action dated Aug. 13, 2025, 6 pages.
Co-pending U.S. Appl. No. 18/400,466 Non-Final Office Action dated Dec. 19, 2024, 9 pages.
Co-pending U.S. Appl. No. 18/400,466 Notice of Allowance dated Nov. 19, 2025, 8 pages.
Co-pending U.S. Appl. No. 18/400,466 Preliminary Amendment dated Aug. 1, 2024, 7 pages.
Co-pending U.S. Appl. No. 18/400,466 Response Aug. 13, 2025 Ex Parte Quayle Action dated Oct. 14, 2025, 11 pages.
Co-pending U.S. Appl. No. 18/400,466 Response to Dec. 19, 2024 Non-Final Office Action, filed Apr. 21, 2025, 9 pages.
Co-pending U.S. Appl. No. 18/400,466, Response to Aug. 29, 2024 Restriction Requirement, dated Oct. 29, 2024, 8 pages.
Co-pending U.S. Appl. No. 18/400,466, Restriction Requirement dated Aug. 29, 2024, 8 pages.
Co-pending U.S. Appl. No. 15/653,618, Final Office Action dated Feb. 12, 2020, 12 pages.
Co-pending U.S. Appl. No. 15/653,618, Final Office Action dated May 17, 2023, 8 pages.
Co-pending U.S. Appl. No. 15/653,618, Final Office Action dated Nov. 10, 2021, 13 pages.
Co-pending U.S. Appl. No. 15/653,618, Final Office Action dated Nov. 19, 2018, 7 pages.
Co-pending U.S. Appl. No. 15/653,618, Non-Final Office Action dated Jul. 27, 2022, 10 pages.
Co-pending U.S. Appl. No. 15/653,618, Non-Final Office Action dated Jun. 14, 2019, 9 pages.
Co-pending U.S. Appl. No. 15/653,618, Non-Final Office Action dated Mar. 31, 2021, 6 pages.

(56) References Cited

OTHER PUBLICATIONS

Co-pending U.S. Appl. No. 15/653,618, Non-Final Office Action dated May 31, 2018, 7 pages.
Co-pending U.S. Appl. No. 15/653,618, Non-Final Office Action dated Sep. 14, 2023, 10 pages.
Co-pending U.S. Appl. No. 15/653,618, Response to Feb. 12, 2020 Final Office Action dated Nov. 23, 2020 and Sep. 29, 2020, 17 pages.
Co-pending U.S. Appl. No. 15/653,618, Response to Jul. 27, 2022 Non-Final Office Action, dated Jan. 26, 2023, 10 pages.
Co-pending U.S. Appl. No. 15/653,618, Response to Jun. 14, 2019 Non-Final Office Action dated Nov. 13, 2019, 11 pages.
Co-pending U.S. Appl. No. 15/653,618, Response to Mar. 31, 2021 Non-Final Office Action, dated Jul. 29, 2021, 12 pages.
Co-pending U.S. Appl. No. 15/653,618, Response to May 17, 2023 Final Office Action, dated Aug. 17, 2023, 10 pages.
Co-pending U.S. Appl. No. 15/653,618, Response to May 31, 2018 Non-Final Office Action dated Aug. 31, 2018, 9 pages.
Co-pending U.S. Appl. No. 15/653,618, Response to Nov. 10, 2021 Final Office Action dated May 10, 2022, 13 pages.
Co-pending U.S. Appl. No. 15/653,618, Response to Nov. 19, 2019 Final Office Action dated Feb. 19, 2018, 10 pages.
Co-pending U.S. Appl. No. 15/653,618, Response to Restriction Requirement dated Jan. 8, 2018, filed Mar. 8, 2018, 8 pages.
Co-pending U.S. Appl. No. 15/653,618, Restriction Requirement dated Jan. 8, 2018, 9 pages.
(Herr, John et al.) Co-pending U.S. Appl. No. 19/545,891, filed Feb. 20, 2026, Specification, Claims, Figures.
Co-pending Australian Patent Application No. 2023270305, Notice of Acceptance dated Mar. 31, 2026, 8 pages.
Co-pending Australian Patent Application No. 2023270305, Response to Apr. 14, 2025 Exam Report, dated Mar. 5, 2026, 22 pages.
Co-pending Canada Patent Application No. 3004745, Response to Dec. 18, 2025 Examiner Requisition, dated Apr. 19, 2026, 102 pages.
Co-Pending Canadian Application No. 3117577, Examiner Requisition dated Mar. 23, 2026, 3 pages.
Co-pending U.S. Appl. No. 17/677,295, Response to Dec. 2, 2025 Final Office Action dated May 4, 2026, 13 pages.

* cited by examiner

AEROGEL IMPLANTS FOR CONTRACEPTION

BACKGROUND OF THE INVENTION

Field of the Invention

The present invention relates to the fields of contraception and/or prevention of sexually transmitted infections or diseases. Provided are compositions, devices and methods of using aerogels for contraception as well as delivery of drugs.

Contraceptive usage has increased globally, yet 40-45% of pregnancies are unintended. In the United States alone, mistimed, unplanned or unwanted pregnancies result in a total public expenditure of ~$21 billion per year. These pregnancies are considered high-risk with evidence that both the women and the children experience worse health outcomes than intended pregnancies. Popular contraceptive methods include male/female condoms, female hormone treatments (pills, patches, implants, etc.), and intrauterine devices. Over the past three decades, even though many effective female contraceptive options have been introduced to market, unintended pregnancy rates have remained relatively constant.

A promising strategy to reduce the number of unintended pregnancies and the subsequent societal and family costs is to increase contraceptive options, specifically options available to men. While men make up approximately 50% of the population, they currently only have three contraceptive options available to them: condoms, withdrawal, and vasectomy. When used correctly, condoms can be an effective contraceptive and prophylactic. However, condoms are frequently used incorrectly and are only approximately 85% effective overall and have a low satisfaction rate. Vasectomy is considered permanent and very effective; however, it is difficult to reverse. The withdrawal method is the least effective form of birth control, but from 2002-2015 withdrawal use has doubled while vasectomy (permanent) and condoms (single use at time of need) usage did not significantly increase. No new male contraceptives have been introduced since the vasectomy in the mid-19th century. International and national studies have shown that over half of men would be willing to use new forms of male contraception, yet no new forms of male contraception exist on the market.

DESCRIPTION OF RELATED ART

Currently, several methods of male contraception are under investigation. These methods can be broken down into two main categories: hormonal and vas-occlusive. (Amory, J. K. Development of Novel Male Contraceptives. Clin. Transl. Sci. 13, 228-237, 2020). Hormonal options such as hormone pills and creams often cause side-effects similar to those observed in female hormonal contraceptives. Some side effects of hormonal male contraceptives include mood swings, depression, and increased risk of suicide. Vas-occlusion has a similar mechanism of action to a vasectomy in that the sperm are prevented from entering into the ejaculatory duct, with the key difference that vas-occlusion does not sever the vessel.

With the advent of novel male contraceptives including hormonal and non-hormonal methods, it is unclear how these male contraceptives will affect the rate of sexually transmitted infections (STIs). One area of interest in public health are multipurpose prevention technologies (MPT), which are combination products that simultaneously provide the user contraception while preventing the contraction of certain STIs. Currently, research on MPTs focus on female patients: for example, intravaginal rings that may deliver antiretroviral drugs for the prevention of HIV. The field lacks a male MPT that provides effective and reversible contraception for men while preventing the contraction of one or more STIs, which may otherwise be referred to as sexually transmitted disease or STDs.

The most publicized vas-occlusive technologies to date are reversible inhibition of sperm under guidance (RISUG) and VASALGEL (pre hydrolyzed RISUG). (Khilwani, B., Badar, A., Ansari, A. S. & Lohiya, N. K. RISUG® as a male contraceptive: journey from bench to bedside. Basic Clin. Androl. 30, (2020); Colagross-Schouten, A., Lemoy, M.-J., Keesler, R. I., Lissner, E. & Vande Voort, C. A. The contraceptive efficacy of intravas injection of VASALGEL for adult male rhesus monkeys. Basic Clin. Androl. 27, 4, 2017.) Both RISUG and VASALGEL are formulations of styrene maleic anhydride (SMA) dissolved in dimethyl sulfoxide (DMSO). Upon injection into the vas deferens (vas), SMA precipitates to coat the inner wall of the vas. The mechanism of action has been reported as both occlusive and spermicidal (depending on the formulation) with the spermicidal action believed to be due to the negative charge present after hydrolysis of the anhydride moieties (Guha, S. K. Biophysical mechanism-mediated time-dependent effect on sperm of human and monkey vas implanted polyelectrolyte contraceptive. Asian J. Androl. 9, 221-227 (2007); Waller, D., Bolick, D., Lissner, E., Premanandan, C. & Gamerman, G. Azoospermia in rabbits following an intravas injection of VASALGEL. Basic Clin. Androl. 26, 6, 2016.) Removal of the SMA from the vas is facilitated by flushing the vas with bicarbonate solution; however, in animal models the sperm lacked acrosomes post-reversal. (Waller, D., Bolick, D., Lissner, E., Premanandan, C. & Gamerman, G. Reversibility of VASALGEL male contraceptive in a rabbit model. Basic Clin. Androl. 27, 2017.)

Another area of interest are compositions and devices for hormonal replacement, such as estrogen, progesterone and/or testosterone replacement therapy (TRT). Currently, TRT involves the implantation of a pellet, which has an extrusion rate of 10% (see Shoskes J J, Wilson M K, Spinner M L. Pharmacology of testosterone replacement therapy preparations. Transl Androl Urol. 2016; 5(6):834-843, doi: 10.21037/tau.2016.07.10). Other adverse events of TRT include site infections, bleeding, and fibrosis.

Over the past several decades, hydrogels, which are water-swollen polymer networks, have been applied to a wide variety of biomedical applications including drug delivery. (Li, J. & Mooney, D. J. Designing hydrogels for controlled drug delivery. Nat. Rev. Mater. 1, 1-17, 2016.) Injectable hydrogels have been shown to be biocompatible with the ability to tune the mechanism of gelation, gelation rates, degradation mechanism, degradation rates, pore/mesh size, swelling ratio, and mechanical properties (Bakaic, E., Smeets, N. M. B. & Hoare, T. Injectable hydrogels based on poly(ethylene glycol) and derivatives as functional biomaterials, RSC Adv 5, 35469-35486, 2015; Avery, R. K. et al. An injectable shear-thinning biomaterial for endovascular embolization, Sci. Transl. Med. 8, 365ra156, 2016; Norouzi, M., Nazari, B. & Miller, D. W. Injectable hydrogel-based drug delivery systems for local cancer therapy, Drug Discov. Today 21, 1835-1849, 2016; Staruch, R. M. T., Glass, G. E., Rickard, R., Hettiaratchy, S. P. & Butler, P. E. M. Injectable Pore-Forming Hydrogel Scaffolds for Complex Wound Tissue Engineering: Designing and Controlling Their Porosity and Mechanical Properties, Tissue Eng. Part B Rev. 23, 183-198, 2017; Tan, H. & Marra, K. G. Injectable, Biodegradable Hydrogels for Tissue Engineering Applications, Materials 3, 1746-1767, 2010), thus making them an ideal candidate for the development of a vas-occlusive contraceptive.

Additional efforts in this area include those described in Chinese Patent CN1812746B and Japanese Patent JP5330533B2, and U.S. Pat. No. 6,725,866, which are each hereby incorporated by reference herein in their entireties, but as with any art improvements are needed.

Injectable hydrogels remain ideal candidates for the development of vas-occlusive contraception; however, even small injection volumes (less than 0.25 mL) into the narrow vas deferens lumen can result in long implant lengths. Long implant lengths may in some cases complicate reversal procedures. A need remains for vas-occlusive contraceptive options that provide the benefits of injectable hydrogels, are implantable at consistent, predictable lengths, and are easily removed.

SUMMARY OF THE INVENTION

Disclosed are compositions and methods of using one or more aerogel implant, which can be used for example for contraception. The aerogel implants are easily inserted, are highly durable, and are able to last greater than 3 months in vivo, such as up to 3 months or more, including from up to 6 months, up to 1 year, up to 5 years, up to 10 years, up to 20 years, or any time in between. In embodiments, the aerogel implants are configured to be removable to provide reversible contraception.

Aspect 1 includes a method of occluding an animal or human body cavity, such as a lumen, comprising: puncturing the body cavity or lumen; implanting an aerogel into the body cavity or lumen; and wherein, upon implantation into the body cavity or lumen, the aerogel is configured to rehydrate.

Aspect 2 is the method of Aspect 1, wherein the aerogel is configured to occlude the body cavity or lumen.

Aspect 3 is the method of Aspect 1 or 2, wherein the aerogel comprises no pores larger than about 3 μm.

Aspect 4 is the method of any of Aspects 1-3, wherein, upon rehydration, the aerogel has a mass percent swelling of at least 100%, such as a mass percent swelling of about 100-2000%.

Aspect 5 is the method of any of Aspects 1-4, wherein, before the implanting, the aerogel comprises less than about 20% water, such as less than about 18%, 15%, 12%, 10%, 8%, 5%, 4%, 3%, 2%, or 1% water.

Aspect 6 is method of any of Aspects 1-5, wherein, upon rehydration, the aerogel forms an implanted hydrogel capable of swelling to at least about 90% of its maximum swelled volume within about 12 hours of implantation into the body cavity or lumen, such as within about 1, 2, 3, 4, 5, 6, 7, 8, 9, 10, or 11 hours of implantation.

Aspect 7 is the method of any of Aspects 1-6, wherein the aerogel further comprises one or more contrast agents, imaging agents, dyes, compounds or excipients that enhance swelling, therapeutic drugs, antimicrobials, anti-inflammatoirepermicidal agents, vasodilators, steroids, hormones, ionic solutions, proteins, nucleic acids, antibodies, or fragments thereof.

Aspect 8 is the method of any of Aspects 1-7, wherein the aerogel has a permanent lifespan in vivo.

Aspect 9 is the method of any of Aspects 1-8, wherein the aerogel further comprises one or more therapeutic agent(s), such as hormones, anti-HIV drugs, antibiotics, and/or anti-virals.

Aspect 10 is the method of any of Aspects 1-9, wherein the aerogel is configured to release the one or more therapeutic agents over a period of at least 5 days, at least a week, or at least a month.

Aspect 11 is the method of any of Aspects 1-10, wherein the body cavity or lumen is an artery, duct, vein, capillary, vessel, or cavity.

Aspect 12 is the method of any of Aspects 1-11, wherein the body lumen is a vas deferens or fallopian tube.

Aspect 13 is the method of any of Aspects 1-12, wherein the aerogel comprises poly(ethylene glycol).

Aspect 14 is the method of any of Aspects 1-13, wherein the aerogel comprises multi-arm poly(ethylene glycol).

Aspect 15 is the method of any of Aspects 1-14, wherein the aerogel comprises one or more of: natural or synthetic monomers, polymers, copolymers or block copolymers, biocompatible monomers, polymers, copolymers or block copolymers, polystyrene, neoprene, polyetherether ketone (PEEK), carbon reinforced PEEK, polyphenylene, polyetherketoneketone (PEKK), polyaryletherketone (PAEK), polyphenylsulphone, polysulphone, polyurethane, polyethylene, low-density polyethylene (LDPE), linear low-density polyethylene (LLDPE), high density polyethylene (HDPE), polypropylene, polyetherketoneetherketoneketone (PEKEKK), nylon, fluoropolymers, polytetrafluoroethylene (PTFE), TFE (tetrafluoroethylene), polyethylene terephthalate (PET or PETE), FEP (fluorinated ethylene propylene), PFA (perfluoroalkoxy alkanes), and/or polymethylpentene (PMP) styrene maleic anhydride, styrene maleic acid (SMA), polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N isopropylacrylamine) (PNIPAM), poly (vinylmethylether), poly (ethylene oxide), poly (ethyl (hydroxyethyl) cellulose), polyoxazoline and any of its derivatives (POx), polylactide (PLA), polyglycolide (PGA), poly(lactide-co-glycolide) PLGA, poly(e-caprolactone), polydiaoxanone, polyanhydride, trimethylene carbonate, poly(β hydroxybutyrate), poly(g-ethyl glutamate), poly (DTH-iminocarbonate), poly(bisphenol A iminocarbonate), poly(orthoester) (POE), polycyanoacrylate (PCA), polyphosphazene, polyethyleneoxide (PEO), polyethyleneglycol (PEG) or any of its derivatives, linear or multi armed PEG and any of its derivatives, polyacrylacid (PAA), polyacrylonitrile (PAN), polyvinylacrylate (PVA), polyvinylpyrrolidone (PVP), polyglycolic lactic acid (PGLA), poly(2 hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPA), poly(vinyl alcohol) poly(acrylic acid) (PVOH-PAA), collagen, silk, silk fibroin, sericin, fibrin, gelatin, hyaluron, cellulose, chitin, dextran, casein, albumin, ovalbumin, heparin sulfate, starch, agar, heparin, alginate, fibronectin, keratin, pectin, elastin, ethylene vinyl acetate, ethylene vinyl alcohol (EVOH), polyethylene oxide, PLA or PLLA (poly(L-lactide) or pol(L-lactic acid)), poly(D,L lactic acid), poly(D,L-lactide), polydimethylsiloxane or dimethicone (PDMS), poly(isopropyl acrylate) (PIPA), polyethylene vinyl acetate (PEVA), PEG styrene, perfluoropolyether (PFPE) and polytetrafluroroethylene (PTFE), fluorinated polyethylene (FLPE), methyl palmitate, temperature responsive polymers, poly(N-isopropylacryl amide) (NIPA), polycarbonate, polyethersulfone, polycaprolactone, polymethyl methacrylate, polyisobutylene, nitrocellulose, medical grade silicone, cellulose acetate, cellulose acetate butyrate, polyacrylonitrile, poly(lactide-co-caprolactone) (PLCL), and/or chitosan; poly (methyl methacrylate), poly (vinyl alcohol), poly (urethanes) poly (ethylene) poly (siloxanes) or silicones, poly (vinyl pyrrolidone), poly (ethylene-co-vinyl acetate), poly (methyl methacrylate), poly (vinyl alcohol), poly (N-vinyl pyrrolidone), poly (acrylic acid), poly (2-hydroxy ethyl methacrylate), polyacrylamide, poly (methacrylic glycol), poly (ethylene glycol), polyorthoesters, poly (lactide co-glycolides) (PLGA), polyactide (PLA), polyanhydride, polyglycolides (PGA); polymers formed from radical polymerization such as polystyrene, poly(acrylic acid), poly(methacrylic acid), poly (ethyl methacrylate), poly(methyl methacrylate), poly (vinyl acetate), poly(ethyleneterepthalate), polyethylene, polypropylene, polybutadiene, polyacrylonitrile, poly(vinyl chloride), poly(vinylidene chloride), poly(vinyl alcohol), polychloroprene, polyisoprene, vinyl fluoride, vinylidene fluoride, trifluoroethylene, poly(methyl-α-chloracrylate), poly (ethylvinyl ketone), polymethacroleine, polyaurylmethacryate, poly(2-hydroxyethylmethamilate), poly (fumaronitrile), polychlorotrifluoroethylene, poly (acrylonitrile), polyacroleine, polyacenaphthylene, and branched polyethylene; natural polymers including silk, rubber, cellulose, alginate, wool, amber, keratin, collagen, starch, DNA, and shellac.

Aspect 16 is the method of any of Aspects 1-15, wherein after the implanting, the length of the aerogel increases by at least 50%.

Aspect 17 is the method of any of Aspects 1-16, wherein after the implanting, the length of the aerogel is in the range of 0.5-15 cm.

Aspect 18 is the method of any of Aspects 1-17, wherein after the implanting, the width (or diameter for cylindrical aerogels) of the aerogel increases by at least 50%.

Aspect 19 is the method of any of Aspects 1-18, wherein: the aerogel is prepared in vitro; in embodiments the aerogel is prepared by dehydrating the hydrogel in vitro then rehydrating the aerogel in vivo to prepare an occlusive hydrogel; the aerogel is configured to provide, upon implantation into the body cavity or lumen, a radial force against a wall of the body cavity or lumen that is about 1.5 times, or 2 times, or 2.5 times, or 3 times, or 3.5 times, or 4 times, or 4.5 times, or 5 times, or 7 times, or 10 times, or 12 times, or 15 times, or 18 times, or up to 20 times the axial force that the hydrogel upon formation in vivo in the body cavity or lumen would be capable of providing.

Aspect 20 is the method of any of Aspects 1-19, wherein the hydrogel, following implantation, exerts a force of at least 3 N on the body cavity or lumen, such as at least 4 N, 5 N, 6 N, 7 N, 8 N, 9 N, 10 N, 11 N, 12 N, or more.

Aspect 21 is the method of any of Aspects 1-20, wherein the hydrogel exerts a force on the body cavity or lumen of less than about 1 N immediately after implantation and greater than about 4 N, such as in the range of 4-12 N, about 12 hours after implantation.

Aspect 22 is an aerogel implant comprising: one or more crosslinked polymer; a moisture content of less than 5%; pores, wherein the pores are no larger than about 3 μm; and wherein the aerogel implant is configured to swell upon implantation into a body cavity or lumen.

Aspect 23 is the aerogel implant of Aspect 22, wherein the swelling is of sufficient magnitude to be capable of exerting a force of at least 3 N on the body cavity or lumen.

Aspect 24 is the aerogel implant of Aspect 22 or 23, wherein the aerogel implant is configured to be capable of exerting a force on the body cavity or lumen of less than about 1 N immediately after implantation and greater than about 4 N, such as about 12 hours after implantation.

Aspect 25 is the aerogel implant of any of Aspects 22-24, wherein upon implantation into a body cavity or lumen the aerogel implant is configured to swell to occlude the body lumen.

Aspect 26 is the aerogel implant of any of Aspects 22-25, wherein upon implantation into a body cavity or lumen the aerogel implant is configured to have a mass percent swelling of at least 100%, such as a mass percent swelling of about 100-2000%.

Aspect 27 is the aerogel implant of any of Aspects 22-26, wherein, the aerogel implant comprises less than about 4% water, such as less than about 3%, 2%, or 1% water.

Aspect 28 is the aerogel implant of any of Aspects 22-27, wherein the aerogel implant is configured to swell, following implantation into a body cavity or lumen, to at least about 90% of its maximum swelled volume within about 12 hours of implantation into the body cavity or lumen, such as within about 1, 2, 3, 4, 5, 6, 7, 8, 9, 10, or 11 hours of implantation.

Aspect 29 is the aerogel implant of any of Aspects 22-28, wherein the aerogel implant further comprises one or more contrast agents, imaging agents, dyes, compounds or excipients that enhance swelling, therapeutic drugs, antimicrobials, anti-inflammatories, spermicidal agents, vasodilators, steroids, hormones, ionic solutions, proteins, nucleic acids, polypeptides, polysaccharides, antibodies, or fragments thereof.

Aspect 30 is the aerogel implant of any of Aspects 22-29, wherein the aerogel implant has a permanent lifespan in vivo.

Aspect 31 is the aerogel implant of any of Aspects 22-30, wherein the aerogel implant further comprises one or more therapeutic agent(s), such as hormones, anti-HIV drugs, antibiotics, and/or anti-virals.

Aspect 32 is the aerogel implant of any of Aspects 22-31, wherein the aerogel implant is configured to release the one or more therapeutic agents over a period of at least 5 days, at least a week, or at least a month.

Aspect 33 is the aerogel implant of any of Aspects 22-32, wherein the body cavity or lumen is an artery, duct, vein, capillary, vessel, or cavity.

Aspect 34 is the aerogel implant of any of Aspects 22-33, wherein the body lumen is a vas deferens or fallopian tube.

Aspect 35 is the aerogel implant of any of Aspects 22-34, wherein the aerogel implant comprises poly(ethylene glycol).

Aspect 36 is the aerogel implant of any of Aspects 22-35, wherein the aerogel implant comprises multi-arm poly (ethylene glycol).

Aspect 37 is the aerogel implant of any of Aspects 22-36, wherein the aerogel implant comprises one or more of:

natural or synthetic monomers, polymers, copolymers or block copolymers, biocompatible monomers, polymers, copolymers or block copolymers, polystyrene, neoprene, polyetherether ketone (PEEK), carbon reinforced PEEK, polyphenylene, polyetherketoneketone (PEKK), polyaryletherketone (PAEK), polyphenylsulphone, polysulphone, polyurethane, polyethylene, low-density polyethylene (LDPE), linear low-density polyethylene (LLDPE), high density polyethylene (HDPE), polypropylene, polyetherketoneetherketoneketone (PEKEKK), nylon, fluoropolymers, polytetrafluoroethylene (PTFE), TFE (tetrafluoroethylene), polyethylene terephthalate (PET or PETE), FEP (fluorinated ethylene propylene), PFA (perfluoroalkoxy alkanes), and/or polymethylpentene (PMP) styrene maleic anhydride, styrene maleic acid (SMA), polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamide) (PNIPAM), poly (vinylmethylether), poly (ethylene oxide), poly (ethyl (hydroxyethyl) cellulose), polyoxazoline and any of its derivatives (POx), polylactide (PLA), polyglycolide (PGA), poly (lactide-co-glycolide) PLGA, poly(ε-caprolactone), polydiaoxanone, polyanhydride, trimethylene carbonate, poly(β hydroxybutyrate), poly(γ-ethyl glutamate), poly (DTH-iminocarbonate), poly(bisphenol A iminocarbonate), poly(orthoester) (POE), polycyanoacrylate (PCA), polyphosphazene, polyethyleneoxide (PEO), polyethyleneglycol (PEG) or any of its derivatives, linear or multi armed PEG and any of its derivatives, polyacrylacid (PAA), polyacrylonitrile (PAN), polyvinylacrylate (PVA), polyvinylpyrrolidone (PVP), polyglycolic lactic acid (PGLA), poly(2 hydroxypropyl methacrylamide) (pHPMAm), poly (vinyl alcohol) (PVOH), PEG diacrylate (PEGDA), poly(hydroxyethyl methacrylate) (pHEMA), N-isopropylacrylamide (NIPAM), poly(vinyl alcohol) poly(acrylic acid) (PVOH-PAA), collagen, silk, silk fibroin, sericin, fibrin, gelatin, hyaluron, cellulose, chitin, dextran, casein, albumin, ovalbumin, heparin sulfate, starch, agar, heparin, alginate, fibronectin, keratin, pectin, elastin, ethylene vinyl acetate, ethylene vinyl alcohol (EVOH), polyethylene oxide, PLA or PLLA (poly(L-lactide) or pol(L-lactic acid)), poly(D,L lactic acid), poly(D,L-lactide), polydimethylsiloxane or dimethicone (PDMS), poly(isopropyl acrylate) (PIPA), polyethylene vinyl acetate (PEVA), PEG styrene, perfluoropolyether (PFPE) and polytetraflurorethylene (PTFE), fluorinated polyethylene (FLPE), methyl palmitate, temperature responsive polymers, polycarbonate, polyethersulfone, polycaprolactone, polymethyl methacrylate, polyisobutylene, nitrocellulose, medical grade silicone, cellulose acetate, cellulose acetate butyrate, polyacrylonitrile, poly(lactide-co-caprolactone) (PLCL), and/or chitosan; poly (methyl methacrylate), poly (vinyl alcohol), poly (urethanes) poly (ethylene) poly (siloxanes) or silicones, poly (vinyl pyrrolidone), poly (ethylene-co-vinyl acetate), poly (methyl methacrylate), poly (vinyl alcohol), poly (N-vinyl pyrrolidone), poly (acrylic acid), poly (2-hydroxy ethyl methacrylate), polyacrylamide, poly (methacrylic glycol), poly (ethylene glycol), polyorthoesters, poly (lactide co-glycolides) (PLGA), polyactide (PLA), polyanhydride, polyglycolides (PGA); polymers formed from radical polymerization such as polystyrene, poly(acrylic acid), poly (methacrylic acid), poly(ethyl methacrylate), poly (methyl methacrylate), poly(vinyl acetate), poly (ethyleneterepthalate), polyethylene, polypropylene, polybutadiene, polyacrylonitrile, poly(vinyl chloride), poly(vinylidene chloride), poly(vinyl alcohol), polychloroprene, polyisoprene, vinyl fluoride, vinylidene fluoride, trifluoroethylene, poly(methyl-α-chloracrylate), poly(ethylvinyl ketone), polymethacroleine, polyaurylmethacryate, poly(2-hydroxyethylmethamilate), poly(fumaronitrile), polychlorotrifluoroethylene, poly(acrylonitrile), polyacroleine, polyacenaphthylene, and branched polyethylene; natural polymers including rubber, cellulose, alginate, wool, amber, keratin, collagen, starch, DNA, and shellac.

Aspect 38 is the aerogel implant of any of Aspects 22-37, wherein after implantation into a body cavity or lumen, the length of the aerogel implant is capable of increasing by at least 50%.

Aspect 39 is the aerogel implant of any of Aspects 22-38, wherein after implantation into a body cavity or lumen, the width or diameter of the aerogel implant is capable of increasing by at least 50%.

Aspect 40 is an aerogel implant comprising one or more crosslinked polymer; wherein the aerogel implant is configured to swell upon implantation into a body cavity or lumen to form a hydrogel; and wherein the hydrogel comprises pores no larger than about 3 μm.

Aspect 41 is the aerogel implant of any of aspects 22-40, wherein when rehydrated, the aerogel implant has a swelling ratio of at least 4 by mass.

Aspect 42 is the aerogel implant of any of aspects 22-41, wherein when rehydrated, the aerogel implant has a swelling ratio of at least 12 by mass, such a swelling ratio of between 10-20.

Aspect 43 is the aerogel implant of any of aspects 22-42, wherein the aerogel implant, upon hydration, forms a hydrogel with a degradation time of at least about 2 months at 70° C.

Aspect 44 is the aerogel implant of any of aspects 22-43, wherein the aerogel implant, upon hydration, forms a hydrogel with a storage modulus of at least 4,000 Pa, such as at least 5,000, or at least 8,000, or at least 10,000, or at least 12,000, or at least 18,000 Pa.

Aspect 45 is the aerogel implant of any of aspects 22-44, wherein the aerogel implant, upon hydration, forms a hydrogel with a burst pressure of at least 1 psi, such as at least 3 psi, at least 5 psi, at least 10 psi, at least 25 psi, at least 50 psi, at least 75 psi, at least 100 psi, at least 150 psi, at least 200 psi, or at least 250 psi, such as between 1-350 psi.

Aspect 46 is the aerogel implant of any of aspects 22-45, wherein the aerogel implant is non-cytotoxic.

Aspect 47 is the aerogel implant of any of aspects 22-45, wherein the aerogel implant has a mass/length ratio of at least 0.25 mg/cm, such as at least 0.5 mg/cm, 0.75 mg/cm, 1 mg/cm, 1.25 mg/cm, 1.5 mg/cm, 1.75 mg/cm, 2 mg/cm, 2.25 mg/cm, 2.5 mg/cm, 2.75 mg/cm, or 3 mg/cm.

Aspect 48 is a method of preparing an aerogel implant comprising: crosslinking one or more type of monomers, macromers, and/or polymers to form a hydrogel; removing water from the hydrogel to form an aerogel; and compressing the aerogel to form an aerogel implant.

Aspect 49 is the method of aspect 48, wherein the removing step is performed using one or more of:

lyophilization; and/or solvent based extraction, such as with ethanol, wherein the extracting is performed with or without one or more of heat, agitation, stirring, and/or vacuum; and/or solvent exchange with one or more volatile solvent(s) (e.g., ethanol, methanol, isopropanol (or other alcohols), acetonitrile, acetone, and/or tetrahydrofuran) followed by removal of the one or more volatile solvent(s) under reduced pressure.

Aspect 50 is the method of aspect 48 or 49, wherein the compressing step is performed using a die stamp or rolling mill.

Aspect 51 is the method of any of aspects 48-50, wherein the compressing of the aerogel is performed in at least 2 directions.

Aspect 52 is the method of any of aspects 48-51, wherein the hydrogel is formed in a mold, such as a tube.

Aspect 53 is the method of any of aspects 48-52, wherein the hydrogel, monomers, macromers, and/or polymers are extruded into tubing during or after the crosslinking.

Aspect 54 is the method of any of aspects 48-53, wherein the aerogel has a diameter of about 1 mm and the aerogel implant has a diameter of about 0.3-1.0 mm.

Aspect 55 is a kit for the delivery of an aerogel implant comprising: a housing containing the aerogel implant; a guide wire or plunger; and a catheter or needle.

Aspect 56 is the kit of aspect 55, wherein the guide wire or plunger comprises a handle.

Aspect 57 is the kit of aspect 55 or 56, wherein the guide wire or plunger is longer than the housing.

Aspect 58 is the kit of any of aspects 55-57, wherein the housing and catheter or needle are configured to connect.

Aspect 59 is the kit of any of aspects 55-58, wherein the housing is substantially tube-shaped and comprises openings at each end.

Aspect 60 is the kit of any of aspects 55-59, wherein the housing comprises a cap for each end.

BRIEF DESCRIPTION OF THE DRAWINGS

The accompanying drawings illustrate certain aspects of embodiments of the present invention and should not be used to limit the invention. Together with the written description, the drawings serve to explain certain principles of the invention.

DETAILED DESCRIPTION OF VARIOUS EMBODIMENTS OF THE INVENTION

Figure 1B:
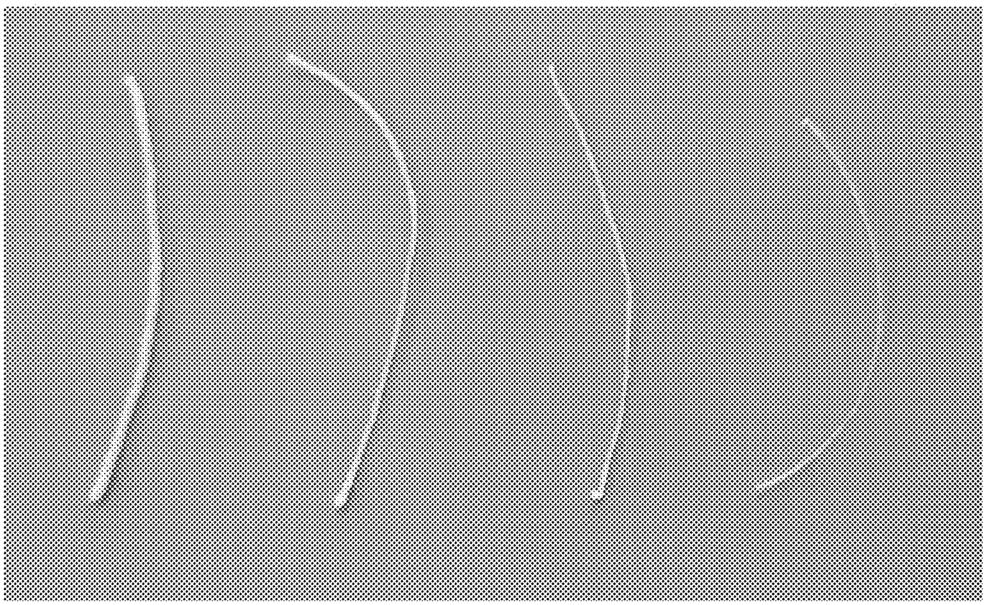
FIG. 1B is a drawing showing aerogel implants according to embodiments of the invention.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Embodiments of the invention include compositions and methods related to aerogel implants configured to swell in vivo following insertion into a body cavity or lumen, such as a vas deferens or fallopian tube, such as to provide an occlusion. In embodiments, in vivo swelling results in a rehydrated hydrogel implant that is dynamically responsive to vessel contraction. The swelling characteristics are surprising and contribute to low failure rates.

Benefits of the aerogel implant according to embodiments of the invention include several safety features, such as i) precise control of the implant length, which can be customized on a patient-by-patient basis, ii) reduced risk of implant migration due to swelling/axial force, and iii) decreased procedural complexity.

Additional benefits include improved swelling and occlusive properties (less chance of failing) and having a fixed length provides for easier reversal.

With a preformed aerogel implant according to embodiments of the invention, a number of terminal sterilization options can be employed and storage of the implants is more manageable especially with respect to storage requirements, such as not requiring cold chain storage, which increases the potential for non-clinic-based procedures.

As used herein, an "aerogel", "aerogel implant", or "lyophilized product" is a hydrogel with air in place of or replacing all or some of the water content of a hydrogel. The "lyophilized product" is an aerogel that is formed by freeze drying a hydrogel.

As used herein, a "hydrogel occlusion" is a hydrogel implant capable of occluding a body cavity or lumen. In embodiments of the invention, an aerogel implant is administered into a body cavity or lumen, forming a hydrogel in situ.

In embodiments, the device or aerogel implant can be formulated for contraception as well as for the delivery of drugs, such as the localized, sustained delivery of drugs over a desired period of time. Examples of intermediate hydrogel formulations that can be used to prepare the aerogel implants and drugs (and other compounds) that can be incorporated therein for delivery can be found in U.S. Patent Publication No. 2022/0175672, which is hereby incorporated herein in its entirety.

In embodiments, the aerogel implants are easily inserted, are highly durable, and are able to last greater than 3 months in vivo, such as up to 3 months or more, including from up to 6 months, up to 1 year, or up to 5 years, or any time in between. In embodiments, the aerogel implants are able to last greater than 5 years in vivo, such as 10 years, 20 years, or more.

In embodiments, the aerogel implants can be prepared by drying hydrogels. In embodiments, hydrogels are prepared and extruded into a mold or tubing with a desired shape and/or diameter. In embodiments, water can be removed by lyophilization while the hydrogels remain in the mold or tubing.

In embodiments, aerogel implants are prepared by removing water from hydrogels through treatment with one or more solvent, such as ethanol. In embodiments, hydrogels are extruded directly into ethanol or another organic solvent. In embodiments, hydrogels are extruded into an aqueous solvent.

In embodiments, following treatment or exposure to the one or more solvent, the hydrogel is exposed to vacuum to remove residual solvent and/or water. Optionally, while under vacuum, the hydrogel is heated to a temperature of up to about 70° C., such as up to about 30° C., 40° C., 50° C., or 60° C.

In embodiments, the hydrogel compositions are prepared by polymerizing one or more type(s) of monomer, macromer, or polymer to form a hydrogel. In embodiments, the hydrogel compositions are prepared from: a first component and a second component capable of combination to form a hydrogel. The resulting hydrogel is then dehydrated, dried, lyophilized and/or otherwise modified to form an aerogel implant.

In embodiments, the aerogel implants formed by drying hydrogels have a moisture content of less than about 25%, such as less than 0.5%, 1%, 2%, 3%, 4%, 5%, 6%, 7%, 8%, 9%, 10%, 12%, 15%, 18%, 20%, or 22%. In embodiments, the aerogel implant is partially rehydrated (or not fully dehydrated during aerogel preparation) prior to in vivo insertion, and as such, the aerogel implant comprises up to about 60 wt % water, such as up to about 1%, 5%, 10%, 15%, 20%, 25%, 30%, 35%, 40%, 45%, 50%, or 55% water (or other liquid).

As used herein, the term "component" (also referred to as "biomaterial component") includes any substance that is capable of forming a hydrogel, aerogel, and/or drug delivery device according to the invention, such as a biomaterial product. For example, a component can include a small molecule, catalyst, peptide, protein, enzyme, nucleotide (or derivatives of), short chains of nucleotides (or derivatives of), long chains of nucleotides (or derivatives of), monosaccharides (or derivatives of), disaccharides (or derivatives of), trisaccharides (or derivatives of), oligo saccharides (or derivatives of), polysaccharides (or derivatives of), monomer, oligomer, macromer, or polymer that can be crosslinked with another component to form a hydrogel, aerogel, and/or drug delivery device according to the invention (e.g., a delivered product or biomaterial product). A component can include a mixture or solution of one or more constituents (e.g., a monomer, macromer, or polymer and a solvent). A component can include such constituents regardless of their state of matter (e.g., solid, liquid or gas). A component can include both active constituents and inert constituents. A constituent may be one or more of a therapeutic agent, an active agent, or drug. For example, in some embodiments, a component can include certain polymers that can form a delivered product, as well as a medicament or other active ingredient. By way of another example, in some embodiments a component can include drugs, including but not limited to, small molecule drugs and biologics. In other embodiments, a component can include certain constituents to impart desired properties to the delivered product, including constituents that facilitate the delivered product being echogenic, radiopaque, radiolucent, or the like.

In embodiments, the components (e.g., monomers, macromers, or polymers) that form the hydrogel, and the aerogel implant formed therefrom, have varied molecular weights, component ratios, concentrations/weight percentages of the components in solvent, and composition of the solvent. Varying any, some, or all of these properties can affect the mechanical, chemical, or biological properties of the device. This includes properties such as, but not limited to, dissolution time, gelation rate/time, porosity, biocompatibility, hardness, elasticity, viscosity, swelling, fluid absorbance, melting temperature, degradation rate, density, reversal time, and echogenicity. Accordingly, one of skill in the art based on this disclosure will know how to "tune" the particular desired features of a hydrogel and/or aerogel to achieve a particular purpose and/or function for a particular application.

In embodiments, the intermediate hydrogel and/or aerogel can be formed by having one or more substances/components/constituents cross-link with one or more of each other, such as macromers.

In embodiments, the aerogel, hydrogel, and/or its macromers can include components including, but not limited to, a polymer backbone, stimuli-responsive functional group(s), and functional groups that enable cross-linking. The functional groups that enable cross-linking can be end groups on the macromer(s). The cross-linking of the macromers may be via bioorthogonal chemistry, such as a Click reaction. In one embodiment, a bioorthogonal reaction is utilized because it is highly efficient, has a quick gelation rate, occurs under mild conditions, and does not require a catalyst.

One example of such reaction is maleimide and thiol. Another type of Click reaction is cycloaddition, which can include a 1,3-dipolar cycloaddition or hetero-Diels-Alder cycloaddition or azide-alkyne cycloaddition, for example. The reaction can be a nucleophilic ring-opening. This includes openings of strained heterocyclic electrophiles including, but not limited to, aziridines, epoxides, cyclic sulfates, aziridinium ions, and episulfonium ions. The reaction can involve carbonyl chemistry of the non-aldol type including, but not limited to, the formation of ureas, thioureas, hydrazones, oxime ethers, amides, and aromatic heterocycles. The reaction can involve carbonyl chemistry of the aldol type. The reaction can also involve forming carbon-carbon multiple bonds, epoxidations, aziridinations, dihydroxylations, sulfenyl halide additions, nitrosyl halide additions, and Michael additions.

Another example of bioorthogonal chemistry is nitrone dipole cycloaddition. The Click chemistry can include a norbornene cycloaddition, an oxanobornadiene cycloaddition, a tetrazine ligation, a [4+1] cycloaddition, a tetrazole chemistry, or a quadricyclane ligation. Other end-groups include, but are not limited to, acrylic, cyrene, amino acids, amine, or acetyl. In one aspect, the end groups may enable a reaction between the polymeric device and the cells lining the tube, duct, tissue, or organ that is being occluded. For example, the devices, compositions, hydrogels and methods of the present invention can include any device, composition, method, hydrogel and/or component/constituent thereof disclosed in any one or more of U.S. Patent Application Publication Nos. 2017/0136143, 2017/0136144, US2018/0028715, US2018/0185096, US2019/0038454, US2019/0053790, US2019/0060513, WO2017/083753, WO2018/139369, WO2019/070632, U.S. Pat. No. 10,155,063, which are each incorporated by reference herein in their entireties.

The macromers or polymers that form the hydrogels (such as the formulations shown in Table 1), which are used in the preparation of the aerogels, according to embodiments of the invention may be one or more of natural or synthetic monomers, polymers, copolymers or block copolymers, biocompatible monomers, polymers, copolymers or block copolymers, polystyrene, neoprene, polyetherether ketone (PEEK), carbon reinforced PEEK, polyphenylene, polyetherketoneketone (PEKK), polyaryletherketone (PAEK), polyphenylsulphone, polysulphone, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, fluoropolymers, polytetrafluoroethylene (PTFE), TFE (tetrafluoroethylene), polyethylene terephthalate (PET or PETE), FEP (fluorinated ethylene propylene), PFA (perfluoroalkoxy alkanes), and/or polymethylpentene (PMP) styrene maleic anhydride, styrene maleic acid (SMA), polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamide) (PNIPAM), poly (vinylmethylether), poly (ethylene oxide), poly (ethyl (hydroxyethyl) cellulose), polyoxazoline and any of its derivatives (POx), polylactide (PLA), polyglycolide (PGA), poly(lactide-co-glycolide) PLGA, poly(ε-caprolactone), polydiaoxanone, polyanhydride, trimethylene carbonate, poly(β-hydroxybutyrate), poly(γ-ethyl glutamate), poly(DTH-iminocarbonate), poly(bisphenol A iminocarbonate), poly(orthoester) (POE), polycyanoacrylate (PCA), polyphosphazene, polyethyleneoxide (PEO), polyethyleneglycol (PEG) or any of its derivatives, linear or multi-armed PEG and any of its derivatives, polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPAM), poly(vinyl alcohol) poly(acrylic acid) (PVOH-PAA), collagen, silk, silk fibroin, sericin, fibrin, gelatin, hyaluron, cellulose, chitin, dextran, casein, albumin, ovalbumin, heparin sulfate, starch, agar, heparin, alginate, fibronectin, keratin, pectin, elastin, ethylene vinyl acetate, ethylene vinyl alcohol (EVOH), polyethylene oxide, PLA or PLLA (poly(L-lactide) or pol (L-lactic acid)), poly(D,L-lactic acid), poly(D,L-lactide), polydimethylsiloxane or dimethicone (PDMS), poly(isopropyl acrylate) (PIPA), polyethylene vinyl acetate (PEVA), PEG styrene, perfluoropolyether (PFPE) and polytetraflurorethylene (PTFE), fluorinated polyethylene (FLPE), methyl palmitate, temperature responsive polymers, polycarbonate, polyethersulfone, polycaprolactone, polymethyl methacrylate, polyisobutylene, nitrocellulose, medical grade silicone, cellulose acetate, cellulose acetate butyrate, polyacrylonitrile, poly(lactide-co-caprolactone) (PLCL), and/or chitosan; poly (methyl methacrylate), poly (vinyl alcohol), poly (urethanes) poly (ethylene) poly (siloxanes) or silicones, poly (vinyl pyrrolidone), poly (ethylene-co-vinyl acetate), poly (methyl methacrylate), poly (vinyl alcohol), poly (N-vinyl pyrrolidone), poly (acrylic acid), poly (2-hydroxy ethyl methacrylate), polyacrylamide, poly (methacrylic glycol), poly (ethylene glycol), polyorthoesters, poly (lactide-co-glycolides) (PLGA), polyactide (PLA), polyanhydride, polyglycolides (PGA); polymers formed from radical polymerization such as polystyrene, poly(acrylic acid), poly(methacrylic acid), poly(ethyl methacrylate), poly(methyl methacrylate), poly(vinyl acetate), poly(ethylene-terepthalate), polyethylene, polypropylene, polybutadiene, polyacrylonitrile, poly(vinyl chloride), poly(vinylidene chloride), poly(vinyl alcohol), polychloroprene, polyisoprene, vinyl fluoride, vinylidene fluoride, trifluoroethylene, poly(methyl-α-chloracrylate), poly(ethylvinyl ketone), polymethacroleine, polyaurylmethacryate, poly(2-hydroxyethylmethamilate), poly(fumaronitrile), polychlorotrifluoroethylene, poly(acrylonitrile), polyacroleine, polyacenaphthylene, and branched polyethylene; natural polymers including rubber, cellulose, alginate, wool, amber, keratin, collagen, starch, DNA, and shellac.

In embodiments, one or more drug/therapeutic/active agent can be added to one or more of the substances that cross-link or polymerize to form the hydrogel. For example, if a hydrogel is formed from two macromers, the drug can be loaded to one of the macromers while in solution, while the other macromer does not contain any drug(s) or contains the same drug/therapeutic/active agent, or another drug/therapeutic/active agent. The drug/therapeutic/active agent(s) may be loaded in the same or varying concentrations in the components/constituents used to form the hydrogel.

In embodiments, the aerogel implant or the in vivo hydrogel comprises a composition capable of forming or dissolving within seconds, minutes, hours, weeks, months, or years, such as up to 1, 10, 20, 30, 50, 60 seconds; up to 1, 2, 3, 4, 5, 6, 7, 8, 9, 10, 15, 20, 25, 30, 40, 45, 50 or minutes; or up to 1, 2, 3, 4, 5, 6, 7, 8, 9, or 10 hours or more; or up to 1, 2, 3, 4, 5, 6, 7, 8, 9, or 10 days or more; or up to 1, 2, 3, 4, 5, 6, 7, 8, 9, or 10 weeks or more; or up to 1, 2, 3, 4, 5, 6, 7, 8, 9, or 10 months or more; or up to 1, 2, 3, 4, 5, 6, 7, 8, 9, or 10 years or more.

Formulations of compositions according to embodiments of the invention are provided in Table 1. In preferred embodiments, the composition comprises one or more polymer comprising polyethylene glycol (PEG), such as a multi-arm PEG (e.g., 4-arm), SMA, or SMAh. The buffer (first column) for example can include any of Acetic Acid-Sodium Acetate (AA), Citric Acid-Sodium Citrate (CA), Citric Acid (0.2)-Phosphate Buffer (0.1) (CP), or Phosphate Buffer (PB), or combinations thereof. The molarity (M) is provided in the second column, which can be adjusted depending on the embodiment. The pH is provided in the third column but can be adjusted for any embodiment to have a pH range of about 4-9. In embodiments (also shown in the first column), the buffer is replaced with a solvent, such as DMSO or acetonitrile (MeCN). The molecular weight (in kDa) is provided in the fourth column but can also be adjusted such that the polymer has a molecular weight within a desired range. The chemistry of the components is provided in the fifth column and can include any of the listed combinations including any one or more functional groups chosen from Thiol (SH), Maleimide (MAL), nitrobenzyl (e.g., o-nitrobenzyl, ONB), Hydrazide (HZ), Isocyanate (IC), Amine (NH), Succinimidyl Glutaraldehyde (SG), Aldehyde (AD), or Epoxide (EP), or combinations thereof. In embodiments, the components include styrene maleic anhydride (SMAh) or styrene maleic acid (SMA), which are prepared by precipitation in aqueous environments (such as neutral to acidic environments). The weight percentage (in solution) is provided in the sixth column and likewise can be adjusted according to particular applications, such as providing a composition comprising a desired polymer with a weight percent of up to 30 wt %, such as from about 1-5 wt %, or from about 2-10 wt %, or from about 3-15 wt %, or from about 10-20 wt %.

TABLE 1

Formulations according to embodiments of the invention

| Buffer or Solvent | M | pH | MW (kDa) | Chem | Wt % |
|---|---|---|---|---|---|
| AA | 0.1 | 4.50 | 20 | SH-MAL | 20 |
| AA | 0.1 | 5.00 | 20 | SH-MAL | 20 |
| AA | 0.2 | 4.50 | 20 | SH-MAL | 20 |
| AA | 0.2 | 4.50 | 20 | SH-MAL | 20 |
| AA | 0.2 | 4.50 | 20 | SH-MAL | 20 |
| AA | 0.2 | 5.00 | 20 | SH-MAL | 20 |
| AA | 0.2 | 5.00 | 20 | SH-MAL | 20 |
| AA | 0.2 | 5.00 | 20 | SH-MAL | 20 |
| AA | 0.2 | 5.50 | 20 | SH-MAL | 20 |
| AA | 0.2 | 5.50 | 20 | SH-MAL | 20 |
| CA | 0.1 | 4.50 | 20 | SH-MAL | 20 |
| CA | 0.1 | 4.50 | 20 | SH-MAL | 20 |
| CA | 0.1 | 4.50 | 20 | SH-MAL | 20 |
| CA | 0.1 | 5.00 | 20 | SH-MAL | 20 |
| CA | 0.1 | 5.00 | 20 | SH-MAL | 20 |
| CA | 0.1 | 5.00 | 20 | SH-MAL | 20 |
| CA | 0.2 | 4.00 | 20 | SH-MAL | 20 |
| CA | 0.2 | 5.25 | 20 | SH-MAL | 20 |
| CA | 0.2 | 5.25 | 20 | SH-MAL | 20 |
| CA | 0.2 | 5.25 | 20 | SH-MAL | 20 |
| CA | 0.2 | 5.25 | 20 | SH-MAL | 20 |
| CA | 0.2 | 5.25 | 20 | SH-MAL | 20 |
| CA | 0.2 | 5.25 | 20 | SH-EMAL (ESTER) | 20 |
| CA | 0.2 | 5.25 | 20 | SH-MAL | 20 |
| CA | 0.2 | 5.25 | 20 | SH-MAL | 20 |
| CA | 0.2 | 5.25 | 20 | SH-MAL | 20 |
| CA | 0.2 | 5.25 | 20 | SH-MAL | 15 |
| CA | 0.2 | 5.25 | 20 | SH-MAL | 10 |
| CA | 0.2 | 5.25 | 20 | SH-MAL | 5 |
| CA | 0.2 | 5.25 | 20 | SH-MAL | 2.5 |
| CA | 0.2 | 5.25 | 20 | SH-MAL | 1 |
| CA | 0.2 | 6.00 | 20 | SH-MAL | 2.5 |
| CA | 0.2 | 6.00 | 20 | SH-MAL | 1 |
| CP | 0.15 | 5.50 | 20 | SH-MAL | 20 |
| CP | 0.15 | 5.50 | 20 | SH-MAL | 20 |
| CP | 0.15 | 5.50 | 20 | SH-MAL | 20 |
| CP | 0.15 | 5.75 | 20 | SH-MAL | 20 |
| CP | 0.15 | 5.75 | 20 | SH-MAL | 20 |
| CP | 0.15 | 5.75 | 20 | SH-MAL | 20 |
| CP | 0.15 | 5.85 | 20 | SH-MAL | 20 |
| CP | 0.15 | 5.85 | 20 | SH-MAL | 20 |
| CP | 0.15 | 5.85 | 20 | SH-MAL | 20 |
| PB | 0.1 | 5.50 | 20 | SH-MAL | 20 |
| PB | 0.1 | 5.50 | 20 | SH-MAL | 20 |
| PB | 0.1 | 5.50 | 20 | SH-MAL | 20 |
| PB | 0.1 | 6.00 | 20 | SH-MAL | 20 |

TABLE 1-continued

Formulations according to embodiments of the invention

| Buffer or Solvent | M | pH | MW (kDa) | Chem | Wt % |
|---|---|---|---|---|---|
| PB | 0.1 | 6.00 | 20 | HZ-AD | 20 |
| PB | 0.1 | 6.50 | 20 | SH-EP | 20 |
| PB | 0.1 | 6.50 | 20 | SH-MAL | 20 |
| PB | 0.1 | 6.50 | 40 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 20 |
| PB | 0.1 | 6.50 | 20 | SH-MAL | 15 |
| PB | 0.1 | 6.50 | 20 | SH-MAL | 10 |
| PB | 0.1 | 6.50 | 20 | SH-MAL | 5 |
| PB | 0.1 | 6.50 | 20 | SH-MAL | 2.5 |
| PB | 0.1 | 6.50(SH) + 7.00 (MAL) | 40 | SH-MAL (ONB) | 15 |
| PB | 0.1 | 7.00 (SG) + 9.00 (NH) | 20 | SG-NH | 20 |
| PB | 0.1 | 7.00 (IC) + 9.00 (NH) | 20 | IC-NH | 20 |
| PB | 0.1 | 7.00 | 20 | SH-MAL | 2.5 |
| PB | 0.1 | 7.00 | 20 | SH-MAL | 1 |
| PB | 0.1 | 8.00 | 20 | SH-MAL | 2.5 |
| PB | 0.1 | 8.00 | 20 | SH-MAL | 1 |
| PB | 0.1 (+0.1/0.2M NaCl) | 6.50 | 20 | SH-MAL | 20 |
| DMSO | — | — | 100 | SMAh | 30 |
| DMSO | — | — | 150 | SMAh | 10 |
| DMSO | — | — | 200 | SMAh | 50 |
| MeCN | — | — | 125 | SMAh | 20 |
| MeCN | — | — | 500 | SMAh | 40 |
| DMSO | — | — | 1000 | SMAh | 30 |
| MeCN | — | — | 750 | SMAh | 45 |
| MeCN | — | — | 100 | SMAh | 30 |
| DMSO | — | — | 350 | SMA | 25 |
| MeCN | — | — | 350 | SMA | 25 |
| DMSO | — | — | 100 | SMA | 10 |
| DMSO | — | — | 1000 | SMA | 50 |
| MeCN | — | — | 500 | SMA | 30 |
| DMSO | — | — | 250 | SMA | 20 |
| MeCN | — | — | 750 | SMA | 40 |

In embodiments in which the aerogel comprises a drug, the aerogel is formulated such that the drug is released from the implant over seconds, minutes, hours, weeks, months, or years, such as up to 1, 10, 20, 30, 50, 60 seconds; up to 1, 2, 3, 4, 5, 6, 7, 8, 9, 10, 15, 20, 25, 30, 40, 45, 50 or minutes; or up to 1, 2, 3, 4, 5, 6, 7, 8, 9, or 10 hours or more; or up to 1, 2, 3, 4, 5, 6, 7, 8, 9, or 10 days or more; or up to 1, 2, 3, 4, 5, 6, 7, 8, 9, or 10 weeks or more; or up to 1, 2, 3, 4, 5, 6, 7, 8, 9, or 10 months or more; or up to 1, 2, 3, 4, 5, 6, 7, 8, 9, or 10 years or more, or any range in between using any of these numbers as endpoints for ranges.

In one embodiment, the molecular weight of the polymers used to form the hydrogels and/or aerogels can be varied from around 1 kDa to 1,000,000 kDa. The molecular weight of the polymer is preferred to be from 10 kDa to 80 kDa. In one example, a high molecular weight can yield small pores in the device and thus, create an effective occlusion. In other embodiments, the polymers can have a weight average molecular weight (Mw) or number-average molecular weight (Mn) ranging from about 1,000 to 1,000,000 Daltons as measured by GPC (gel permeation chromatography) with polystyrene standards, mass spectrometry, or other appropriate methods.

In embodiments, the number average molecular weight (Mn) or the weight average molecular weight (Mw) of polymers of the invention can range from about 1,000 to about 1,000,000 Daltons, such as from about 3,000 to about 60,000 Daltons, or from about 20,000 to about 90,000 Daltons, or from about 150,000 to about 900,000 Daltons, or from about 200,000 to about 750,000 Daltons, or from about 250,000 to about 400,000 Daltons, or from about 300,000 to about 800,000 Daltons, and so on. Further, the degree of polymerization of the polymers in embodiments can range from 1 to 10,000, such as from 50 to 500, or from 500 to 5,000, or from 1,000 to 3,000 Daltons.

The rate of polymerization or depolymerization can be tailored for a particular application and depends on various factors such as compositions, component ratios, concentration/weight percentages, solvent composition, drug composition, drug concentration, pH, temperature, and other factors as previously described.

The molecular weight of substances (e.g., one or more drugs, therapeutics and/or active agents) delivered by the polymer can range from less than 900 Daltons for small molecules to up to 1000 kDa for biologics, for example.

In embodiments, the chain length or degree of polymerization (DP) can have an effect on the properties of the polymers. In the context of this specification, the degree of polymerization is the number of repeating units in the polymer molecule. In embodiments, the polymers include from 2 to about 10,000 repeating units. Preferred are polymers which include from about 5 to 10,000 repeating units, such as from about 10 to 8,000, or from about 15 to 7,000, or from about 20 to 6,000, or from about 25 to 4,000, or from about 30 to 3,000, or from about 50 to 1,000, or from about 75 to 500, or from about 80 to 650, or from about 95 to 1,200, or from about 250 to 2,000, or from about 350 to 2,700, or from about 400 to 2,200, or from about 90 to 300, or from about 100 to 200, or from about 40 to 450, or from about 35 to 750, or from about 60 to 1,500, or from about 70 to 2,500, or from about 110 to 3,500, or from about 150 to 2,700, or from about 2,800 to 5,000, and so on.

If two or more components are used to form the intermediate hydrogel, and as such the aerogel implant, the ratio of the components can be varied. The ratio can be 1:1, 2:1, 1:2, 3:1, 1:3, such as from 1:1 to 1:10, or from 1:2 to 1:20, and so on. For example, a 1:1 ratio allows for the highest degree of cross-linking to occur. The ratio determines the rate of crosslinking and thus, gelation of the hydrogel that is used to form the aerogel implant.

In embodiments, the aerogel implant is implanted into the body part, organ, duct, cavity/space, or lumen using a needle, catheter, or combination thereof. In embodiments, a guide wire (or other means for providing force sufficient to move the aerogel implant through the needle/catheter, such as a plunger, stream of air, fluid etc.) is used during implantation. For occlusion or tissue fillers, the size of the needle or catheter can be chosen based on the estimated size of the body part, organ, duct, cavity/space or lumen from the literature, or determined by imaging the dimensions of the body part, organ, duct, cavity/space or lumen of the subject through ultrasound or other imaging modality. In embodiments, the size of the needle can be between 18 gauge to 34 gauge. In other embodiments, the size of the needle is between 21 gauge and 31 gauge. In other embodiments, the size of the needle is at least 23 gauge, such as between 23 gauge and 29 gauge.

In one embodiment, the weight percent, or concentration of the components in solution, is varied from around 1% to around 50% of the component(s) in solvent. The weight percent of each component can be the same or different, such as from about 1% to 2%, from about 2% to 3%, from about 3% to 4%, from about 4% to 5%, from about 5% to 6%, from about 6%, to 7%, from about 7%, to 8%, from about 8% to 9%, from about 9% to 10%, from about 5-40%, from about 10-35%, from about 15-25%, from about 20-30%, and so on, or any range using these values as endpoints. In another embodiment, the weight percent of the macromer(s) is from about 2.5% to about 35% in the solvent, or from about 6% to about 30%, or from about 7% to about 25%, or from about 8% to about 20%, or from about 10% to about 30%, or from about 10% to about 20%, and so on. The weight percent of each monomer can be the same or different. The weight percent can affect the mechanical and chemical properties of the polymer, such as increasing or decreasing pore size, viscosity, hardness, elasticity, density, and degradation.

The solvent that the component is dissolved in can be aqueous (water-based) or an organic solvent e.g. DMSO, acetonitrile (MeCN), PEG, ethanol, or mixtures thereof. The final composition may contain excipients for purposes such as increased solubility or quicker dissolution rate. The pH of the composition in solution can be varied from 4 to 9, such as from 4 to 5, 5 to 6, 6 to 7, 7 to 8, and 8 to 9. The pH of the solution can affect the gelation time and stability of the macromer in solution.

In one embodiment, the gelation rate and time of formation of the hydrogel varies. Gelation can occur instantaneously, in less than 1 minute, or within 1-10 minutes.

In some embodiments, the aerogel, partially rehydrated hydrogel implant, or rehydrated hydrogel implant is conveyed out of the exit opening of a delivery member into a body part, organ, duct, cavity/space or lumen to at least partially or fully occlude the body part, organ, duct, cavity/space or lumen. In embodiments, the delivery member containing the implant is inserted into the body and a guide wire is used to hold the implant in a desired position while the delivery member is withdrawn, retracted or removed thereby implanting the implant into the body. The guide wire and delivery member can then be removed from the body leaving behind the implant.

In some embodiments, the body part, organ, duct, cavity/space or lumen is chosen from an artery, vein, capillary, vessel, tissue, intra-organ space, lymphatic vessel, a femoral artery, popliteal artery, coronary and/or carotid artery, esophagus, cavity, nasopharyngeal cavity, ear canal, tympanic cavity, sinus, sinuses of the brain, any artery of the arterial system, any vein of the venous system, heart, larynx, trachea, bronchi, stomach, duodenum, ileum, colon, rectum, bladder, kidney, ureter, ejaculatory duct, epididymis, vas deferens, urethra, uterine cavity, vaginal canal, fallopian tube, cervix, duct, bile duct, a hepatic duct, a cystic duct, a pancreatic duct, a parotid duct, organ, a uterus, prostate, organ of the gastrointestinal tract, organ of the circulatory system, organ of the respiratory system, organ of the nervous system, urological organ, subcutaneous space, intramuscular space, or interstitial space.

In one embodiment, the hydrogel implant (e.g., partially rehydrated hydrogel or rehydrated hydrogel) or aerogel implant swells upon contact with one or more fluids inside the body. Swelling allows for the device to secure itself or "lock" within the body part, duct, organ, cavity/space or lumen to form a good occlusion. The device can swell greater than 100%, such as 100-200%, 200-300%, 300-400%, and so on for example up to 2000%. The greater the device swells, the greater the likelihood of the device allowing fluid to travel through, and for hydrostatic pressure to be reduced. Swelling may also allow for the device to properly secure itself within the body part, duct, organ, cavity/space or lumen.

In embodiments, upon implantation of the aerogel implant, a solvent, such as an aqueous solution, is flushed into or onto the body part, organ, duct, cavity/space, or lumen to facilitate rehydrating and/or swelling of the aerogel.

According to another embodiment, the hydrogel, aerogel implant, and/or rehydrated hydrogel implant (includes partially and fully rehydrated hydrogels) includes pores. In embodiments, the pores are homogenous on the surface of the device. The porosity is defined by the properties of the macromers and cross-linking of the macromers. In embodiments, the pore diameter of the formed polymer ranges from 0.001 nm to 3 μm, such as from 0.001 nm to 1 μm. In other embodiments, the pore diameter ranges from 0.01 nm to 100 nm, or from about 1 nm to about 1 μm. In other embodiments, the pore diameter is 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 95, 90, 95, or 100 nm. In other embodiments, the pore diameter is at least the size of an atom (0.5 nm). Specific pore sizes can be targeted to provide an optimum porosity that provides maximum flow of fluid while blocking the flow of sperm cells or ova. In other embodiments, the pores range from 0.1 nm to 2 microns in diameter. In one embodiment, the device is suitable for occlusion of reproductive cells. The pores are less than 3 μm to prevent the flow of sperm. The pores allow for fluid to travel through the implant. The mesh size of the implant/device is small enough to block reproductive cells from traversing through. In embodiments, such as for drug delivery devices/implants, a larger pore size may be desired for quicker release of drug from the implant.

In embodiments, the aerogel implant has a length of up to about 10 cm, such as up to about 1, 2, 3, 4, 5, 6, 7, 8, or 9 cm. In embodiments, the aerogel can be cut to the desired length or the aerogel during the formation of the intermediate hydrogel can be configured to have a desired length. In embodiments, upon implantation, the aerogel swells into a partially or fully re-constituted or rehydrated hydrogel with a length of occlusion produced in a body part, duct, organ, cavity/space or lumen as a result of administering. In embodiments, the length of occlusion ranges from 0.1-10 centimeters in length, including 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 cm in length, and so on, and any range using any of these values as endpoints. In embodiments, the aerogel implant swells following implantation resulting in a hydrogel occlusion with a length of up to about 5 times the length of the aerogel (prior to swelling), such as up to about 1, 1.25, 1.5, 1.75, 2, 2.25, 2.5, 2.75, 3, 3.5, 4, or 4.5 times the length of the aerogel prior to swelling.

In embodiments, implants are made by first forming an intermediate hydrogel, then dehydrating the intermediate hydrogel to obtain an aerogel, then implanting the aerogel and allowing the aerogel to rehydrate in vivo to obtain an aerogel implant (e.g., rehydrated intermediate hydrogel), the resulting aerogel implant exhibits a swelling force greater than the intermediate hydrogel would if the intermediate hydrogel was formed directly in vivo without the step of forming an aerogel. In embodiments, the aerogel implant has a swelling force that is between 1-2 times the swelling force of the intermediate hydrogel, or is between 1-10 times, or is between 2-8 times, or is between 3-5 times, or is between 1.5-3 times the swelling force of the intermediate hydrogel. In embodiments, the swelling force of the aerogel implant is in the range of about 2.5 Newtons to 15 Newtons, or from 5 Newtons to 12 Newtons, or from 3-10 Newtons, such as from 3-9 Newtons, or any range using any of these values as endpoints.

In embodiments, the aerogel implant has a diameter of up to about 1 mm, such as up to about 0.05 mm, 0.075 mm, 0.1 mm, 0.15 mm, 0.2 mm, 0.3 mm, 0.4 mm, 0.5 mm, 0.6 mm, 0.7 mm, 0.8 mm, 0.9 mm, 1.0 mm. In embodiments, the aerogel implant swells in vivo following implantation resulting in a hydrogel occlusion (e.g., partially or fully rehydrated hydrogel) with a diameter of up to about 10 times the diameter of the aerogel implant (prior to swelling), such as up to about 1, 1.25, 1.5, 1.75, 2, 2.25, 2.5, 2.75, 3, 3.5, 4, 4.5, 5, 5.5, 6, 6.5, 7, 7.5, 8, 8.5, 9, 9.5, or 10 times the diameter of the aerogel implant prior to swelling. In embodiments, the length of the aerogel implant can be in the range of 0.5 cm to 15 cm. For example, the aerogel implants can have a diameter in the range of about 0.05-1 mm and a length in the range of 0.5-15 cm, such as a diameter of 0.1-0.8 mm and a length of 5-10 cm, or a diameter of 0.3-0.6 mm and a length of 7-15 cm, or a diameter of 0.4-0.5 mm and a length of 5-12 cm.

In one embodiment, the aerogel/hydrogel/device/implant/delivered product does not degrade inside the body in that it is permanent. In another embodiment, the aerogel/hydrogel/device/implant/delivered product degrades partially or fully or is capable of degrading in the body, for example, by way of an endogenous stimulus (e.g., hydrolysis). The degradation rate is slow enough that the device remains an effective occlusion inside the body for greater than three months. According to another embodiment, the device degrades upon application of an exogenous stimulus, for example, by photodegradation (e.g., ultraviolet or infrared exposure), acoustic, and/or enzymatic degradation. Alternatively, or in addition to any of these embodiments, the aerogel implant (e.g., hydrogel/device/delivered product) is configured to have a lifetime that is as long as or longer than the drug/therapeutic agent/active agent release profile.

In some embodiments, the aerogel implant is formed from a composition including a first component and a second component that are each formulated to be crosslinked with the other to form a hydrogel. The first component and the second component are formulated to have an initial storage modulus (initial G') and an initial loss modulus (initial G") when initially combined such that a ratio of the initial G" to the initial G' is between about 5 and about 100. The first component and the second component are formulated to have a gelation storage modulus (gelation G') and a gelation loss modulus (gelation G") at a gelation time after the first component and the second component are combined such that a ratio of the gelation G" to the gelation G' is less than about 5, such as less than about 1. In embodiments, the gelation time is less than about 120 seconds. The term "gelation" refers to the transition of the hydrogel components from a soluble polymer of finite branches to a substance with infinitely large molecules. Similarly stated, "gelation" refers to the condition where the gel forms and after the components are combined. Thus, the gelation time refers to the time that it takes for the resulting hydrogel to substantially reach equilibrium.

In some embodiments, the gelation time is less than about 60 seconds, for example, less than about 30 seconds, and in some cases may be instantaneous/immediate. In other embodiments, the gelation time is between about 1 second and 60 seconds. The particular components used to form the hydrogel/device/delivered product can be selected such that the gelation time/rate is "tuned" for the particular application. For example, the components/constituents can be selected to provide for faster or slower gelation times as desired. Alternatively or in addition, the components/constituents used to form the aerogel can be extruded at a rate of up to about 50 mL/min, such as up to about 0.1 mL/min, 0.5 mL/min, 1 mL/min, 1.5 mL/min, 2 mL/min, 2.5 mL/min, 3 mL/min, 4 mL/min, 5 mL/min, 8 mL/min, 10 mL/min, 12 mL/min, 15 mL/min, 17 mL/min, 20 mL/min, 25 mL/min, 30 mL/min, 35 mL/min, 40 mL/min, or 45 mL/min, to provide a desired mechanical property, such as a swelling force in the range of 2.5-15 Newtons, or 2-12 Newtons, or 4-10 Newtons, or a swelling force of the implant that is greater than the swelling force that would result from a hydrogel used to make the aerogel implant.

In some embodiments, the ratio of the gelation G" to the gelation G' is less than about 0.2, such as about 0.1. In yet other embodiments, the ratio of the gelation G" to the gelation G' is a ratio of up to 1, such as a ratio of up to 0.9, or up to 0.8, or up to 0.7, or up to 0.6, or up to 0.5, or up to 0.4, or up to 0.3, or up to 0.2, or up to 0.1.

In some embodiments, the first component and the second component are formulated to have an initial storage modulus (initial G') and an initial loss modulus (initial G") when the first component and the second component are initially combined. A ratio of the initial G" to the initial G' is between about 5 and about 100. The first component and the second component are formulated to have a delivered storage modulus (delivered G') and a delivered loss modulus (delivered G") when the first component and the second component are conveyed out of the delivery member (e.g., at the delivery time). A ratio of the delivered G" to the delivered G' is between about ⅓ and about 3. In some embodiments, the ratio of the initial G" to the initial G' is between about 30 and about 5 and the ratio of the delivered G" to the delivered G' is between about ⅓ and about 1. In some embodiments, the first component and the second component are formulated to have a gelation storage modulus (gelation G') and a gelation loss modulus (gelation G") after the gelation time and a ratio of the gelation G" to the gelation G' being less than about 0.2. In some embodiments, the ratio of the gelation G" to the gelation G' is about 0.1.

In some embodiments, the first component is at least one of a polyvinyl alcohol, alginate or modified alginate, chitosan or modified chitosan, polyethyleneimine, carboxymethyl cellulose, and/or polyethylene glycol terminated with a bioorthogonal functional group (e.g., amine, thiol, maleimide, azide, activated ester). The second component is at least one of a water or buffer, water or buffer with divalent cations such as calcium, a solution of reduced hyaluronic acid, a solution of polystyrene sulfonate, a solution of gelatin, and/or polyethylene glycol terminated with a bioorthogonal functional group (e.g., amine, thiol, maleimide, azide, activated ester). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent. In some embodiments the polysaccharides may be modified with different functional groups. In some embodiments the polysaccharides and proteins may range in molecular weight from 10,000-1,000,000 grams/mole. In some embodiments, the polyvinyl alcohol, polystyrene sulfonate, polyethyleneimine, and polyethylene glycol may be linear, Y-shaped, 3-arm, 4-arm, 6-arm, or 8-arm and range in molecular weight from 1,000-1,000,000 grams/mole.

In some embodiments, the dissolving solution for the polymer component(s) may be aqueous buffers, including any one or more of phosphate, citrate, acetate, histidine, lactate, tromethamine, gluconate, aspartate, glutamate, tartrate, succinate, malic acid, fumaric acid, alpha-ketoglutaric, and/or carbonate. Specific solvents/buffers can include: 1) acetic acid and sodium acetate (AA), 2) citric acid and sodium citrate (CP), 3) citric acid and phosphate buffer (CP), and 4) phosphate buffer (PB), or combinations thereof. Non-aqueous solvents include: dimethyl isosorbide, glycofurol 75, PEG 200, diglyme, tetrahydrofurfuryl alcohol, ethanol, acetone, solketal, glycerol formal, dimethyl sulfoxide, propylene glycol, ethyl lactate, N-methyl-2-pyrrolidone, dimethylacetamide, methanol, isopropanol, 1,4-butanediol, ethyl acetate, toluene, acetonitrile, and combinations thereof. In embodiments, the dissolving solution can include mixtures of aqueous and non-aqueous (e.g., organic) solvents such as a mixture of any one or more of phosphate, citrate, acetate, histidine, lactate, tromethamine, gluconate, aspartate, glutamate, tartrate, succinate, malic acid, fumaric acid, alpha-ketoglutaric or carbonate in combination with any non-aqueous solvent, such as one or more of dimethyl isosorbide, glycofurol 75, PEG 200, diglyme, tetrahydrofurfuryl alcohol, ethanol, acetone, solketal, glycerol formal, dimethyl sulfoxide, propylene glycol, ethyl lactate, N-methyl-2-pyrrolidone, dimethylacetamide, methanol, isopropanol, 1,4-butanediol, ethyl acetate, toluene or acetonitrile.

The molarity of the solutions/solvents/buffers can range for example from 0.01 M to 0.15 M to 0.2 M. In some embodiments, the solution can include a 0.2 M citric acid buffer and can be formulated to have a solution pH of between 4.0 and 6.0. In some embodiments, the pH of the solution can be between 4.0 and 5.25, or about 4.0. In other embodiments, the pH of the solution can be about 5.25, 5.5, 5.75, 6, 6.25, or 6.5. In yet other embodiments, the pH of the solution can be between about 4.5 and about 8 such as a pH of about 5-7, or about 4.5-6.

In embodiments, a first component and a second component can each be a water soluble component (e.g., monomer, macromer, polymer, or the like) that is capable of crosslinking (e.g., with the other component) to form an intermediate hydrogel. In some embodiments, the first component and the second component are formulated such that the resulting intermediate hydrogel has a gelation time of less than 5 minutes. In other embodiments, the first component and the second component are formulated such that the resulting intermediate hydrogel has a gelation time of less than 2 minutes. In other embodiments, the first component and the second component are formulated such that the resulting intermediate hydrogel has a gelation time of less than minute. In yet other embodiments, the first component and the second component are formulated such that the resulting intermediate hydrogel has a gelation time of less than 30 seconds.

In some embodiments, the first component is at least one of a polyvinyl alcohol, alginate or modified alginate, chitosan or modified chitosan, polyethyleneimine, carboxymethyl cellulose, and/or polyethylene glycol terminated with a bioorthogonal functional group (e.g., amine, thiol, maleimide, azide, activated ester). The second component is at least one of a water or buffer, water or buffer with divalent cations such as calcium, a solution of reduced hyaluronic acid, a solution of polystyrene sulfonate, a solution of gelatin, and/or polyethylene glycol terminated with a bioorthogonal functional group (e.g., amine, thiol, maleimide, azide, activated ester). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent. In some embodiments the polysaccharides may be modified with different functional groups. In some embodiments the polysaccharides and proteins may range in molecular weight from 10,000-1,000,000 grams/mole. In some embodiments, the polyvinyl alcohol, polystyrene sulfonate, polyethyleneimine, and polyethylene glycol may be linear, Y-shaped, 3-arm, 4-arm, 6-arm, or 8-arm and range in molecular weight from 1,000-1,000,000 grams/mole. The intermediate hydrogel can comprise any combination of the components described herein and can have any of the characteristics as indicated herein. For example, in some embodiments, the formed intermediate hydrogel can be at least 90 percent water. Water can then be removed from the intermediate hydrogel to form the aerogel implant.

In some embodiments, the dissolving solution for the polymer component(s) may be aqueous buffers (pH range 1-14), such as phosphate, citrate, acetate, histidine, lactate, tromethamine, gluconate, aspartate, glutamate, tartrate, succinate, malic acid, fumaric acid, alpha-ketoglutaric, and/or carbonate, or combinations thereof. Non-aqueous solvents include: dimethyl isosorbide, glycofurol 75, PEG 200, diglyme, tetrahydrofurfuryl alcohol, ethanol, acetone, solketal, glycerol formal, dimethyl sulfoxide, propylene glycol, ethyl lactate, N-methyl-2-pyrrolidone, dimethylacetamide, methanol, isopropanol, 1,4-butanediol, ethyl acetate, toluene, acetonitrile, and combinations thereof. In some embodiments, when the polymer component is dissolved, the viscosity of the solution(s) that make up the biomaterial may range from 0.1 to 250,000 cP. The density of the solution may range from 0.1 to 20,000 kg/m$^3$. The temperature during extrusion may range from 2 to 45° C. The pH of the solution(s) may range from 1-14. The ionic strength of the solution(s) may range from 1 nM to 70 M.

In some embodiments, the aerogel is prepared from a biomaterial/hydrogel comprising one or more components. If two components are used to form the biomaterial/hydrogel, then the ratio of the components may be varied such as 1:1, 2:1, 1:2, 3:1, 1:3, 4:1, 1:4, and up to 10:1 or 1:10. The gelation rate of the biomaterial may range from about 0.001 seconds to 60 minutes. The length of the formed biomaterial may range from about 0.1 to 60 cm. The volume of the formed biomaterial may range from about 0.001 to 100 mL.

In some embodiments, the aerogel implant or partially dehydrated or rehydrated hydrogel implant swells within the implantation space to lock or secure its placement. For example, a biomaterial in the form of a hydrogel may swell from about 1.5×-20× its initial volume and/or mass, such as about 2×, 2.5×, 3×, 3.5×, 4×, 4.5×, 5×, 5.5×, 6×, 6.5×, 7×, 7.5×, 8×, 8.5×, 9×, 9.5×, 10×, 10.5×, 11×, 11.5×, 12×, 12.5×, 13×, 13.5×, 14×, 14.5×, 15×, 15.5×, 16×, 16.5×, 17×, 17.5×, 18×, 18.5×, 19×, 19.5× or 20× its initial volume and/or mass. In some embodiments, the implant conforms to the space it is implanted into. In some embodiments, the swelling of the implant does not change volume within the implantation space, or shrinks to conform to a volume of the implantation space.

Example 1

An intermediate hydrogel (not shown in the figures) is prepared by crosslinking a first polymer comprising PEG and terminated with maleimide functional groups and a second polymer comprising PEG and terminated with thiol functional groups. The components can be extruded as a pre-combination of the components or combined and extruded simultaneously. The intermediate hydrogel in this example was extruded into PTFE tubing of a selected inner diameter to result in an intermediate hydrogel and ultimately an aerogel with a selected outer diameter. In embodiments, the intermediate hydrogel can be extruded through tubing to obtain the desired shape and/or size. Other types of molds can be used and/or the intermediate hydrogel can be formed without a mold. The mold can be selected to control the length and/or the diameter of the intermediate hydrogel and as such the resulting aerogel. The shape of the intermediate hydrogel or the aerogel can be any shape such as a cylinder, triangular prism, or rectangular prism. The intermediate hydrogel or the aerogel can have a cross-section that is any shape, such as circular, rectangular, square, round, etc. The intermediate hydrogel is lyophilized to remove at least about 90% of the moisture, forming aerogel implant 2.

The aerogel implant 2 can be implanted into the body as the lyophilized product, or as a rehydrated hydrogel implant, or as a partially rehydrated hydrogel implant. One benefit of dehydrating the intermediate hydrogel is that aerogel implant 2 prepared in this manner can exhibit an unexpectedly surprising swelling force as compared to implants formed without dehydrating the intermediate hydrogel into an aerogel and rehydrating to form the implant. For contraception and/or occlusion within the body, such as in the vas, a swelling force that is sufficient to enable the implant/device to push against the vas or vessel wall, but which is insufficient to cause harm to the tissue, is highly desired. Implants of the present invention are capable of providing a swelling force that provides for contraceptive efficacy of over 90%, such as over about 95%, 96%, 97%, 98%, 99%, or even approaching 100%, such as 99.9%, 99.8%, 99.7%, 99.6%, 99.5%, 99.4%, 99.3%, 99.2%, 99.1%, for example.

Figure 1A:
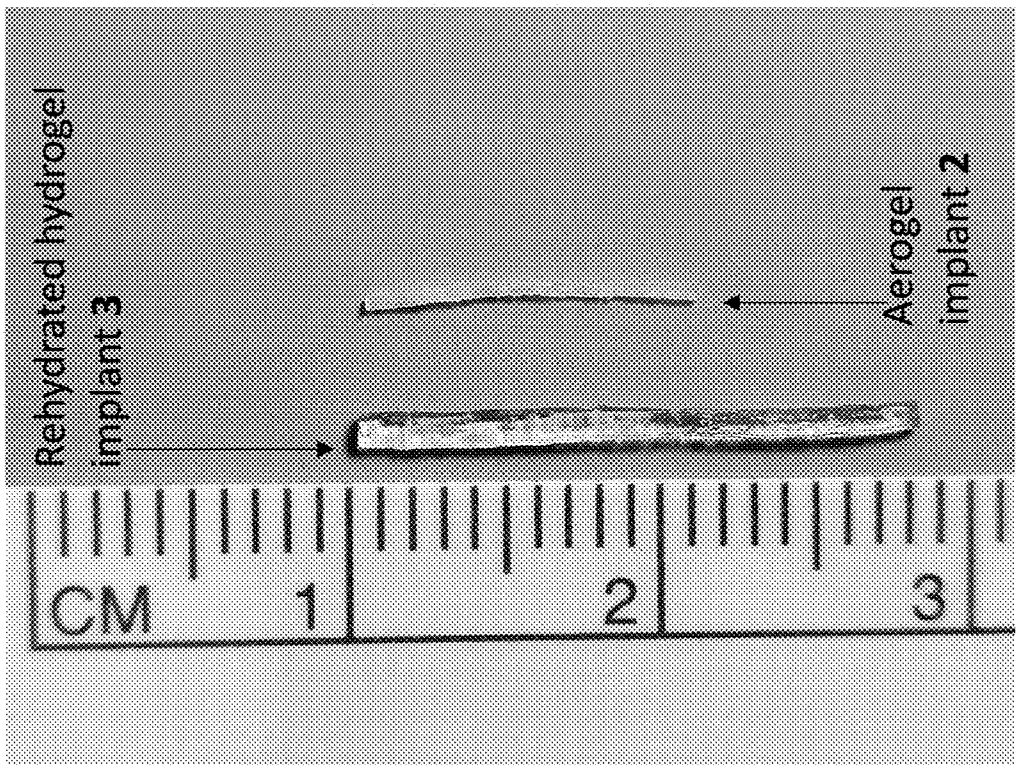
FIG. 1A is a drawing showing an aerogel implant and a rehydrated aerogel implant according to embodiments of the invention.

FIG. 1A shows aerogel implant 2 and rehydrated hydrogel implant 3. The aerogel implant 2 is approximately 1 cm in length with a diameter of approximately 0.7 mm before rehydration. The aerogel implant 2 was exposed to water to simulate the swelling process upon implantation in vivo. The rehydrated hydrogel implant 3 swelled to a length of about 1.8 cm.

TABLE 2

Comparison of swelling of hydrogel 1 and aerogel implant 2.

| Formulation | Polymer Mass (mg) | Swelling Ratio (mass) (Mean ± SD) | n |
|---|---|---|---|
| Hydrogel 1 | 20 | 5.3 ± 0.9 | 35 |
| Aerogel 2 | 20 | 6.3 ± 1.2 | 34 |

Figure 2:
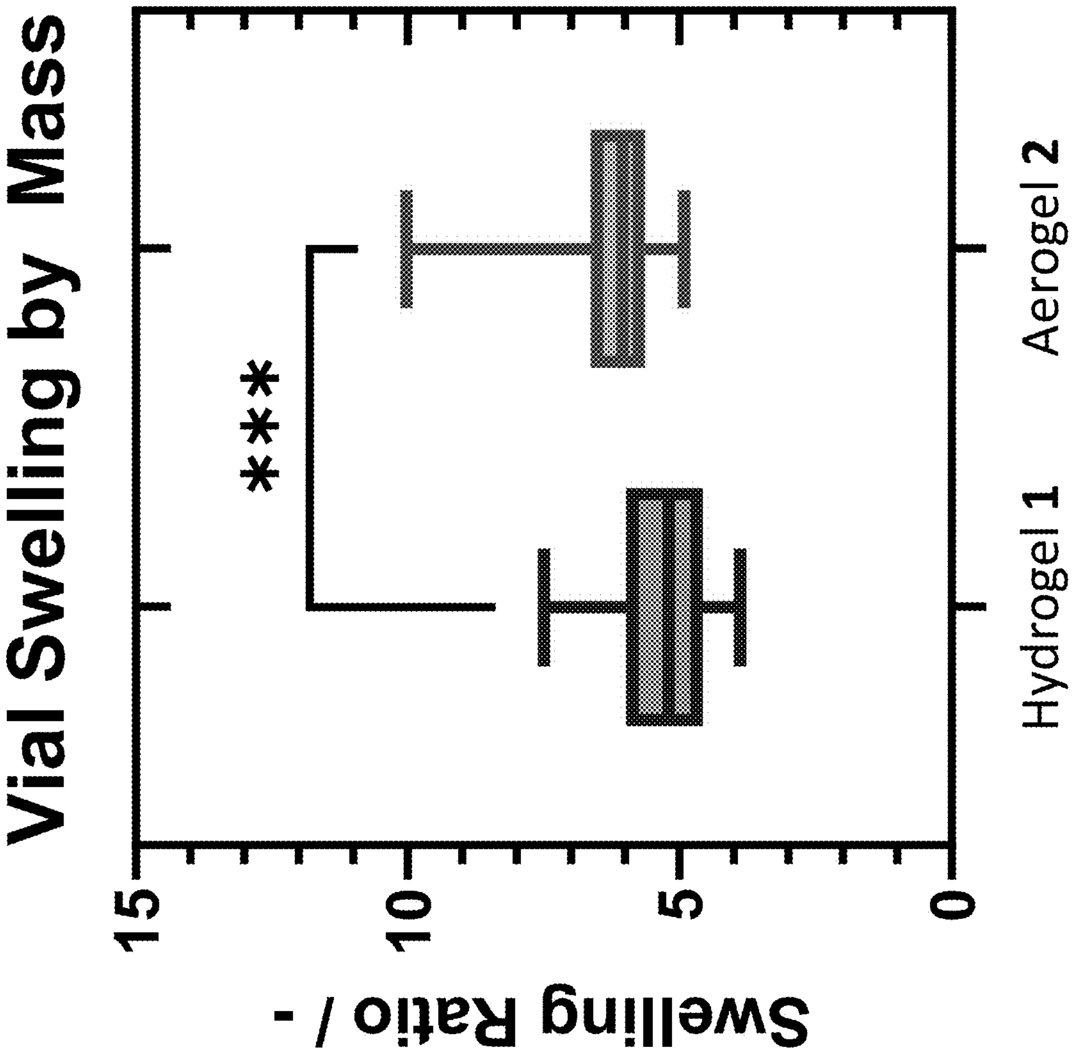
FIG. 2 is a graph showing swelling ratios for hydrogels and aerogel implants according to embodiments of the invention.

As shown in FIG. 2, in embodiments, the aerogel implant 2 exhibits about 20% more swelling by mass than the corresponding intermediate hydrogel 1.

Figure 3:
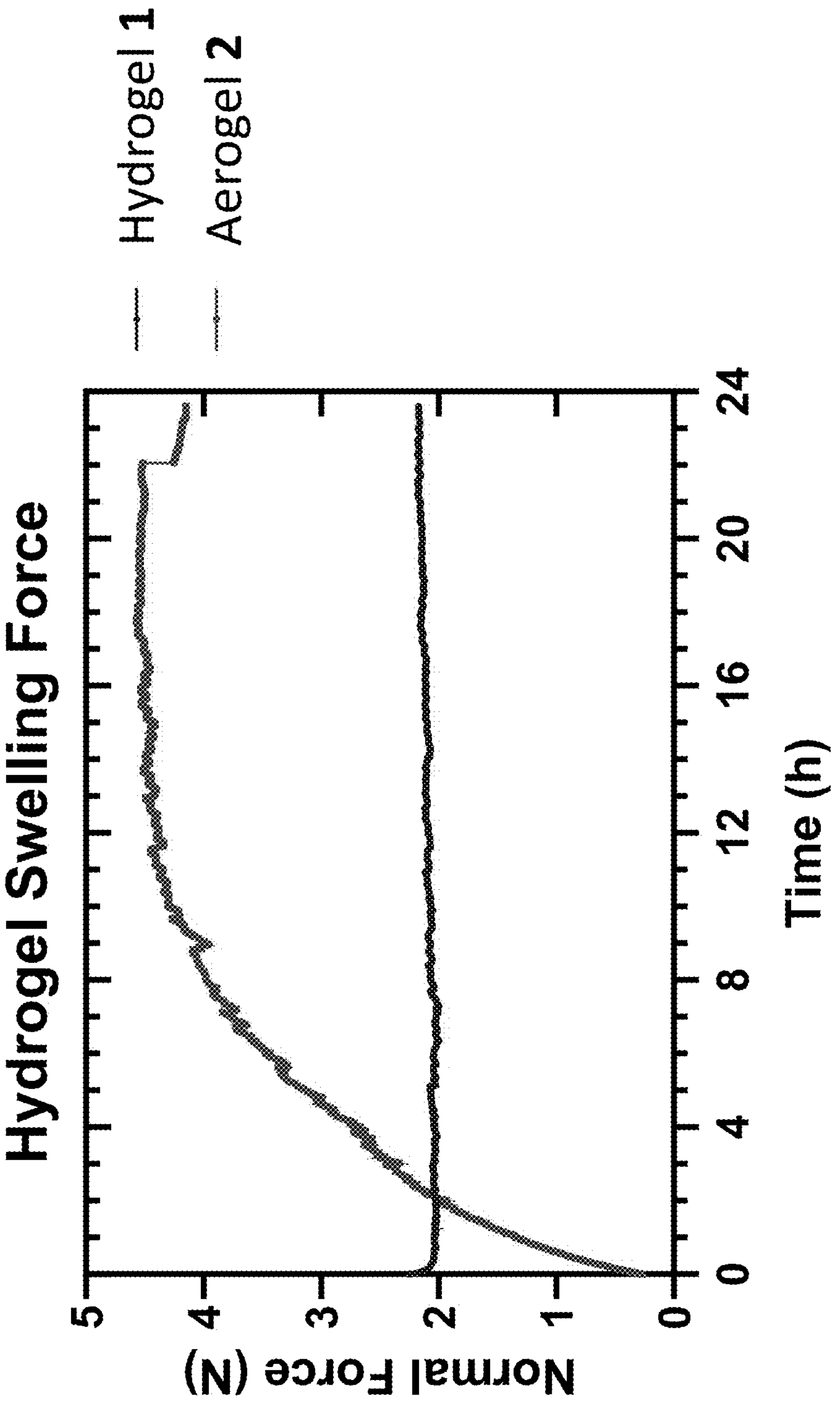
FIG. 3 is a graph showing swelling forces for a hydrogel and an aerogel implant according to embodiments of the invention.

FIG. 3 is a graph showing the hydrogel swelling force for the aerogel implant 2 and hydrogel 1. Post swelling, the aerogel implant 2 (forming rehydrated hydrogel implant 3) generates>200% more axial force than hydrogel 1. This indicates the rehydrated hydrogel implant 3 would resist migration in vivo to a greater extent than hydrogel 1 (after swelling) and/or provide for better occlusion and/or efficacy.

Figure 4:
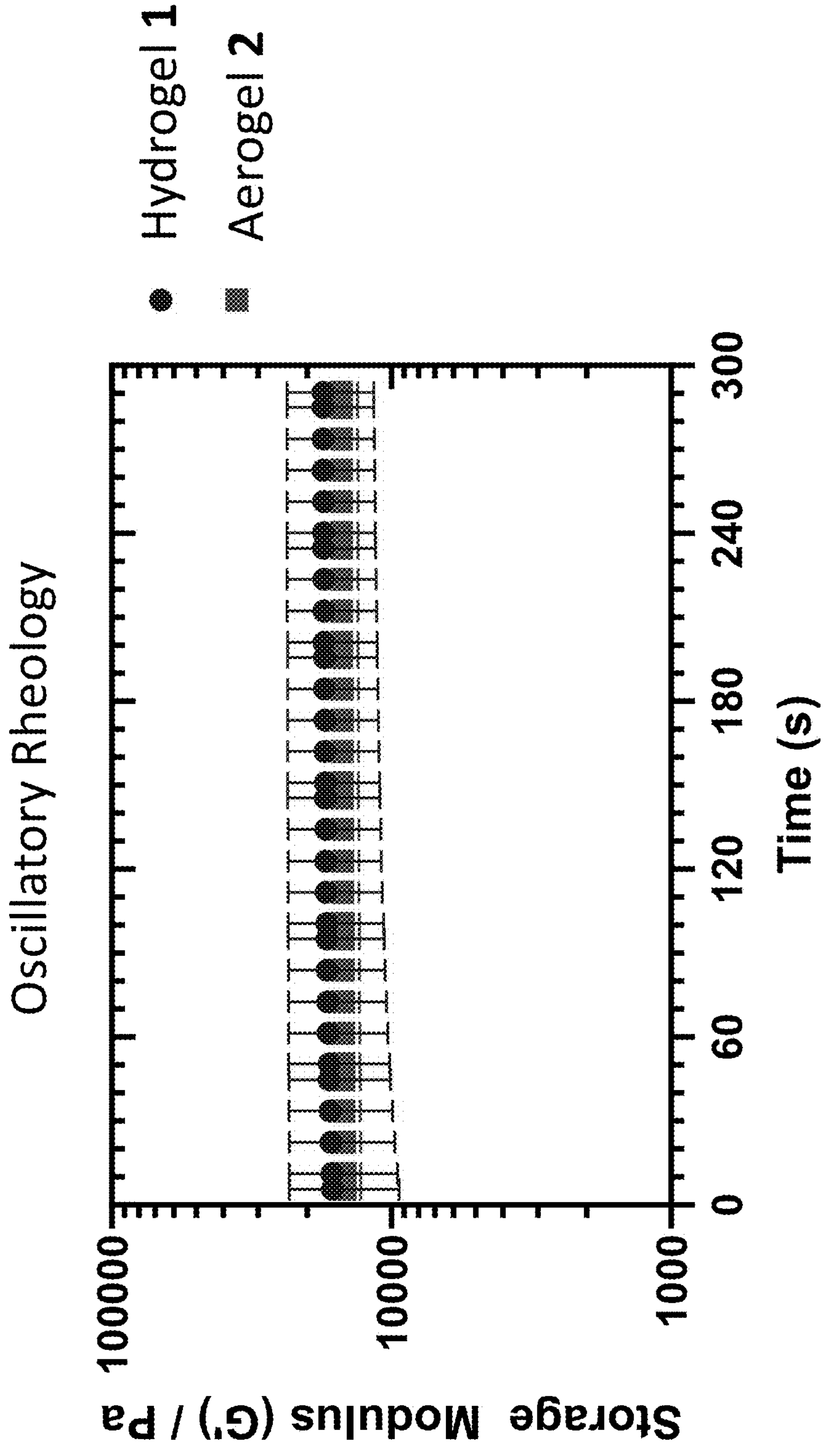
FIG. 4 is a graph showing the storage modulus over time for hydrogels and aerogel implants according to embodiments of the invention.

FIG. 4 is a graph showing oscillatory rheology measurements for the hydrogel 1 and the aerogel implant 2. The storage moduli (G') for the aerogel implant 2 are similar to the hydrogel 1.

Example 2

An intermediate hydrogel is prepared by crosslinking a first polymer comprising a 4-arm PEG and terminated with maleimide functional groups and a second polymer comprising a 4-arm PEG and terminated with thiol functional groups at a concentration of 20 wt % in 200 mM Citric Acid-Sodium Citrate buffer. The product is then extruded into PTFE tubes, each having a selected internal diameter in the range of 0.5 mm-1.35 mm (0.5 mm, 0.8 mm, 1.0 mm and 1.35 mm). Before crosslinking and extrusion, the starting materials can be prepared as separate polymer/buffer solutions then combined for crosslinking or can be prepared as a single solution. In embodiments, the solution(s) can be prepared separately in advance and stored at −20° C. until crosslinking is to be performed. The PTFE tubes are cured at ambient temperature for approximately 1 hr. The cured products are then sectioned into approximately 5 cm sections. The tube sections are frozen at −80° C., then lyophilized to remove water. The resultant aerogel 5 cm sections (FIG. 1B) can then be used as is and/or cut to a customized length and/or implanted and/or packaged and/or stored for later implantation or other use.

Example 3

Figure 5:
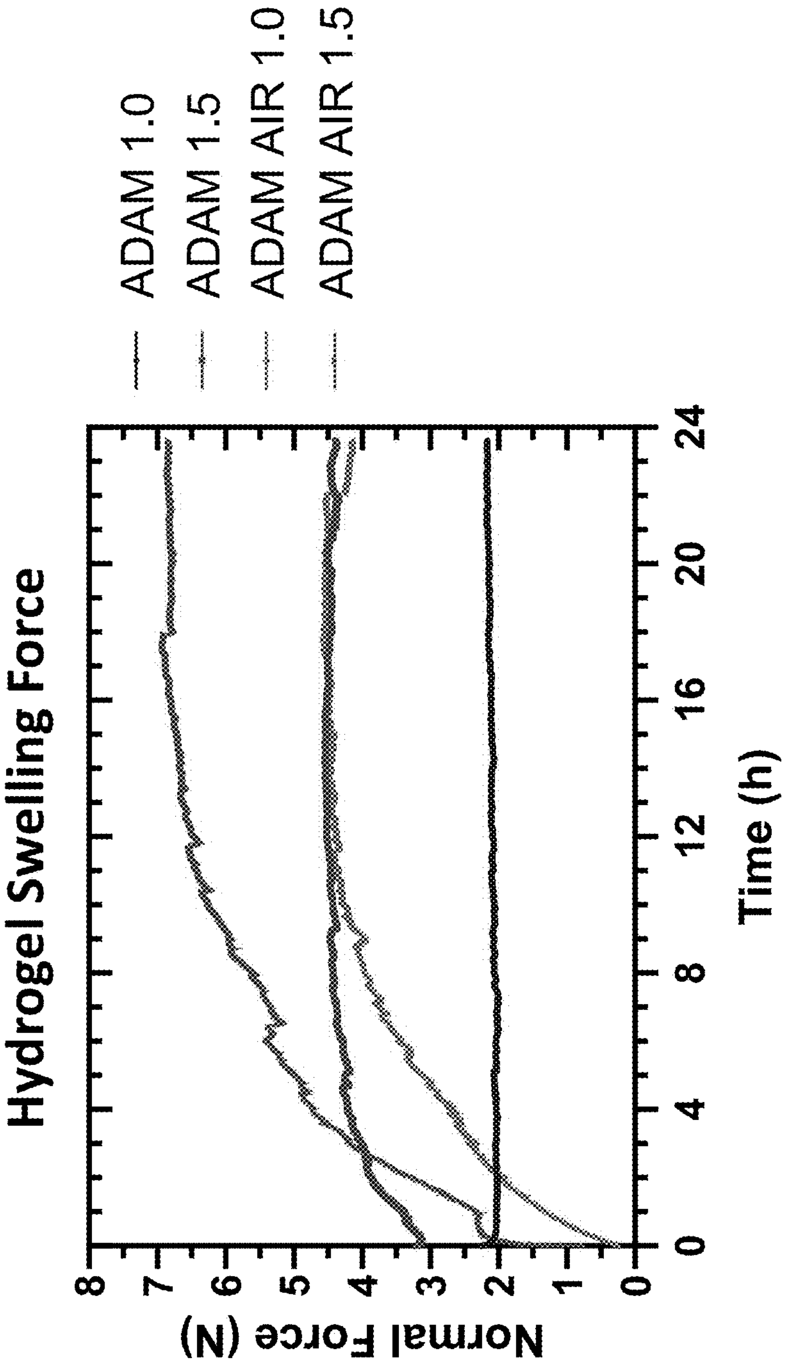
FIG. 5 is a graph showing the hydrogel swelling force for hydrogels and aerogel implants according to embodiments of the invention.

FIG. 5 is a graph showing the hydrogel swelling force for aerogels and hydrogels according to embodiments of the invention. The aerogel implants generate ~50-100% greater swelling than the corresponding hydrogels.

Figure 6:
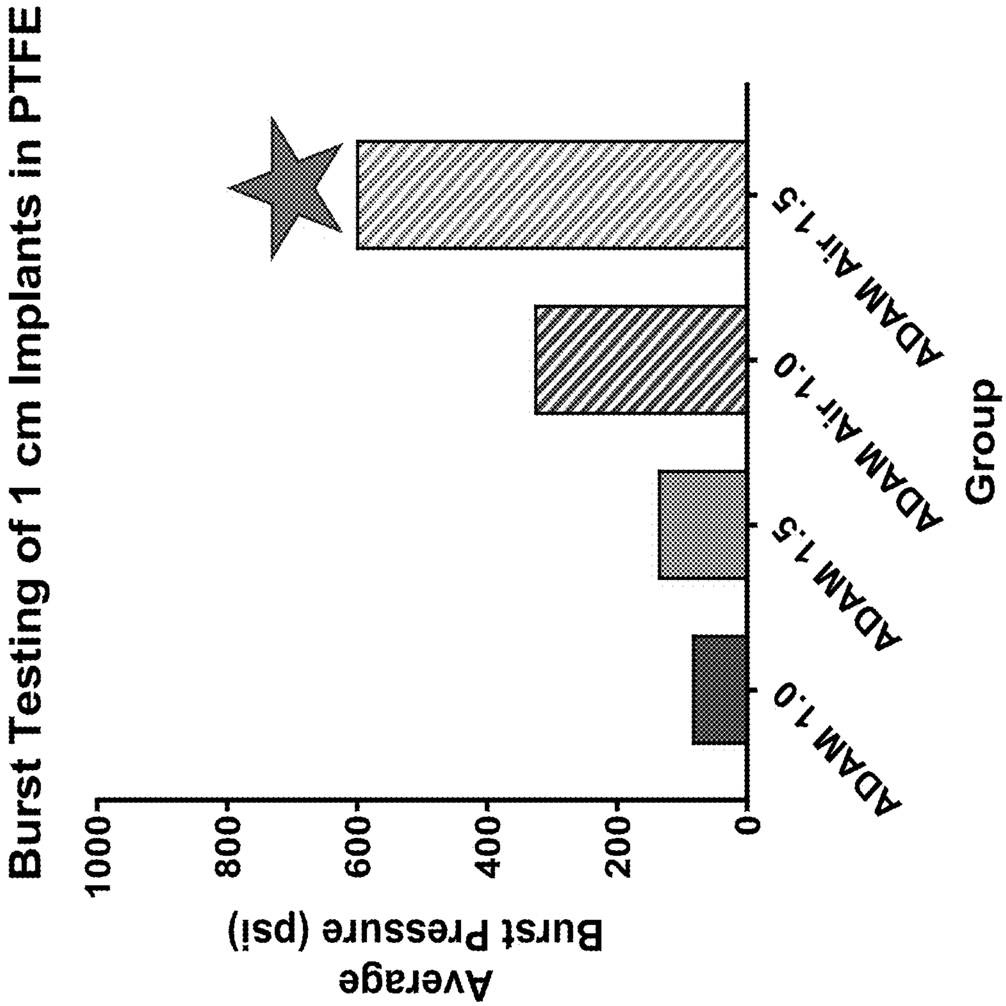
FIG. 6 is a graph showing average burst pressure for hydrogels and aerogel implants according to embodiments of the invention.

FIG. 6 is a graph showing the average burst pressure for aerogels and hydrogels according to embodiments of the invention. The aerogels show a 284% and 606% increase in burst pressure from the hydrogel. In embodiments the rehydrated aerogels have a burst pressure of at least 100 psi, such as at least 150 psi, at least 200 psi, or at least 250 psi, such as between 100-350 psi, such as when rehydrated in a tube with a 0.5 mm to 1.2 mm inner diameter.

Example 4: Implant Formation

Figure 7A:
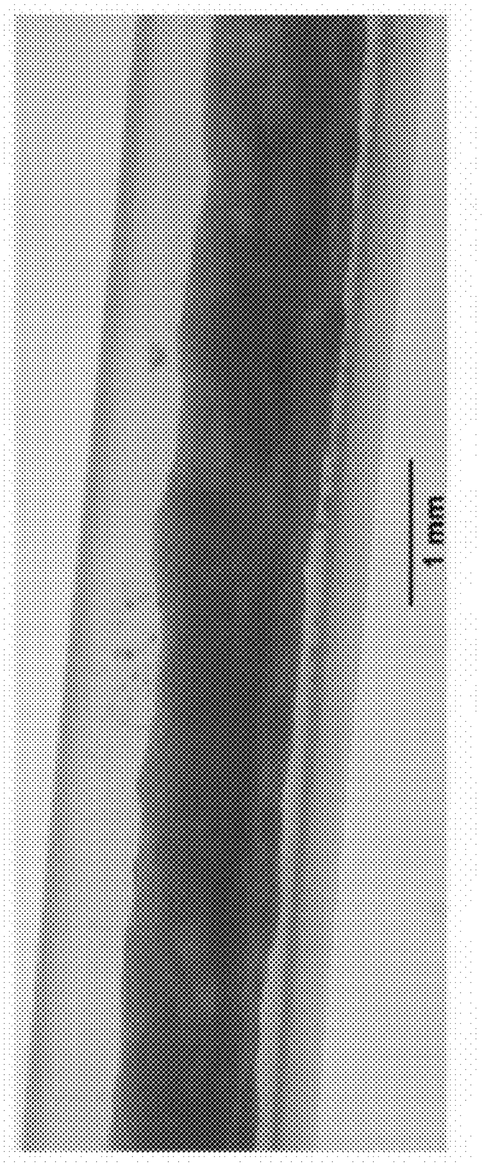
FIG. 7A is a drawing showing a lyophilized aerogel implant inside a length of PTFE tubing according to embodiments of the invention.

A two-compartment syringe is used to inject PEG-SH and PEG-MAL to form a hydrogel in PTFE tubing with an internal diameter of about 1.0 mm. In embodiments, the components can be extruded as a pre-combination of the components or combined and extruded simultaneously. A hydrogel is formed from the cross-linked components inside the tubing, which is then sectioned into desired lengths, frozen, and lyophilized (FIG. 7A).

Figure 7B:
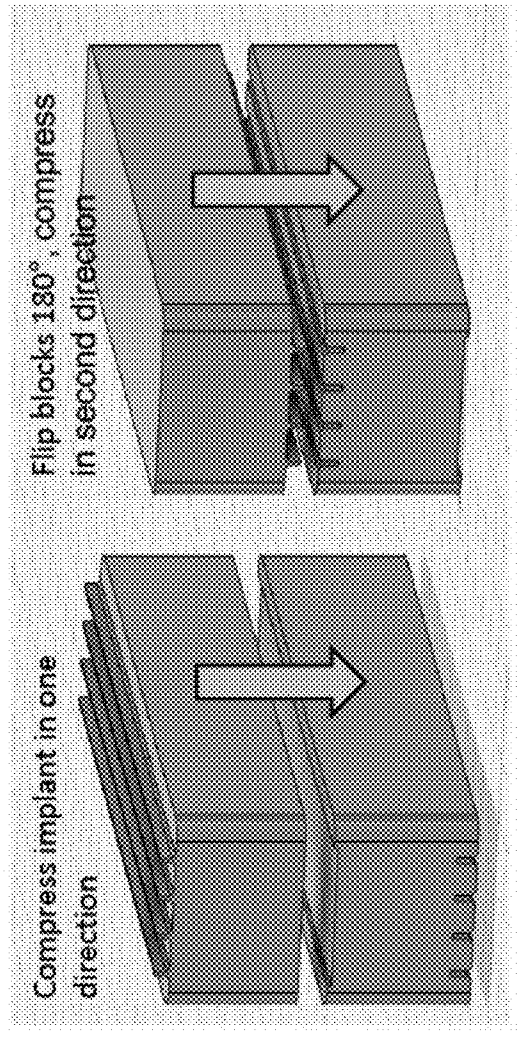
FIG. 7B is a drawing showing a method of compressing aerogel implants according to embodiments of the invention.
Figure 7C:
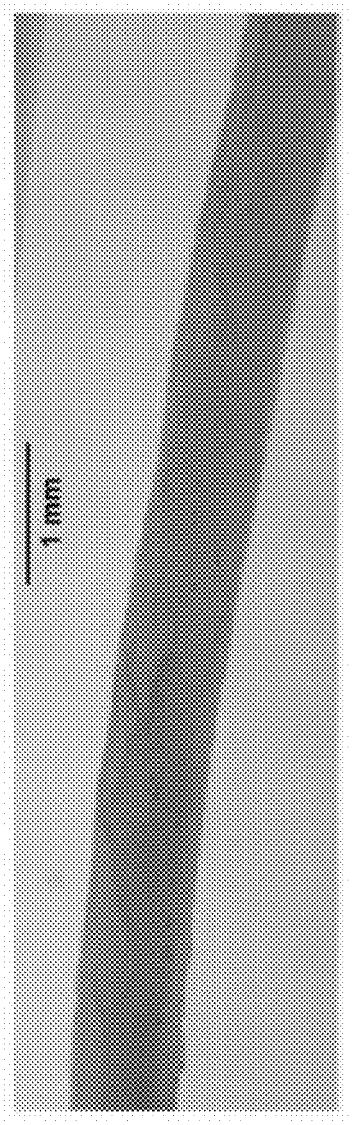
FIG. 7C is a drawing showing a compressed aerogel implant according to embodiments of the invention.

Following lyophilization, the lyophilized hydrogel is compressed to an outer diameter of about 0.6 mm using a die stamp mold or rolling mill. As shown in FIG. 7B, the lyophilized hydrogel is compressed in a first direction to flatten it, then compressed in a second direction to form the aerogel implant (FIG. 7C). In embodiments, the implant is trimmed to a length of approximately 10 cm.

Figure 7D:
FIG. 7D is a drawing showing a re-hydrated aerogel implant according to embodiments of the invention.

FIG. 7D shows a rehydrated aerogel implant.

TABLE 3

Injectable Hydrogel and Implantable Aerogel Comparison Data

| Test Type | Injectable Hydrogel Composition 1 | Injectable Hydrogel Composition 2 (with swelling excipient) | Aerogel Implant |
|---|---|---|---|
| 4-Hour Swelling Ratio (by Mass) | 1.96 (N = 16) | 2.46 (N = 6) | 13.10 (N = 6)* |
| Final Swelling Ratio (by Mass) | 4.36 (N = 30) | 4.471 (N = 30) | 13.14 (N = 5)* |
| 70° C. Degradation | 36 Days (N = 30) | 43 Days (N = 30) | 63 Days (N = 10) |
| Swelling Force (Rheology) | 2.1 N (N = 3) | 4.46 (N = 1) | 9.1 N (N = 3) |
| Equilibrated Storage Modulus (Rheology) | 4562 Pa (N = 29) | 12686 Pa (N = 3) | 18134 Pa (N = 5) |
| Burst Testing | 107.8 psi (N = 9)** | 82.9 psi (N = 9)** | 249.4 psi (N = 12) |
| Cytotoxicity | All components non-cytotoxic | All components non-cytotoxic | All components non-cytotoxic |

*Swelling Ratio values reported for aerogel implant compressed ~300% then swollen in pH 7.2 100 mM PBS

**Injectable hydrogel compositions 1 and 2 do not have a statistically significant difference in burst pressure

Example 5: Implant Disinfection/Dehydration

In an embodiment of the invention, the aerogel implants are disinfected and/or desiccated using one or more solvent, such as ethanol.

Figure 8A:
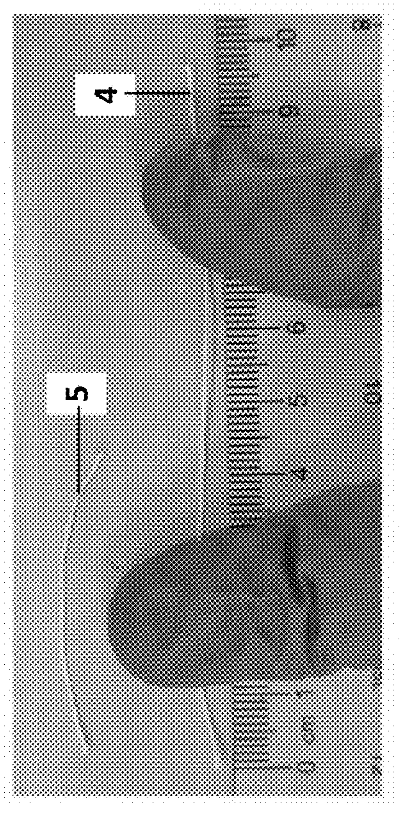
FIG. 8A is a drawing comparing a disinfected aerogel implant and a control aerogel implant according to embodiments of the invention.
Figure 8B:
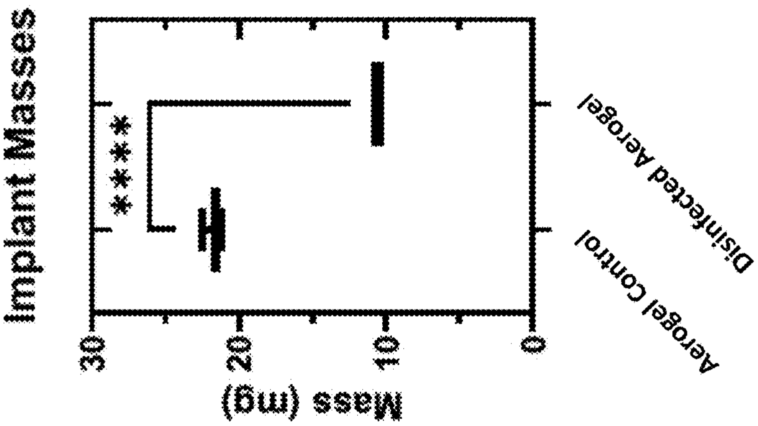
FIG. 8B is a graph showing the difference in masses between a disinfected aerogel implant and a control aerogel implant according to embodiments of the invention.

A 10 cm implant 4 (such as an implant formed via the procedure described in Example 4), is compared to a 10 cm implant disinfected by soaking in 50 mL of ethanol for 24 h. The disinfected implant is then vacuum dried for 72 h to give disinfected implant 5 (FIG. 8A). The masses for control samples (N=8, 10 cm implant not exposed to ethanol) and the disinfected implants (N=8) are shown in FIG. 8B. The disinfected implants (average mass=10.54 mg) had an average reduction in mass of 51.4% as compared to the control samples (average mass 21.69 mg).

Figure 8C:
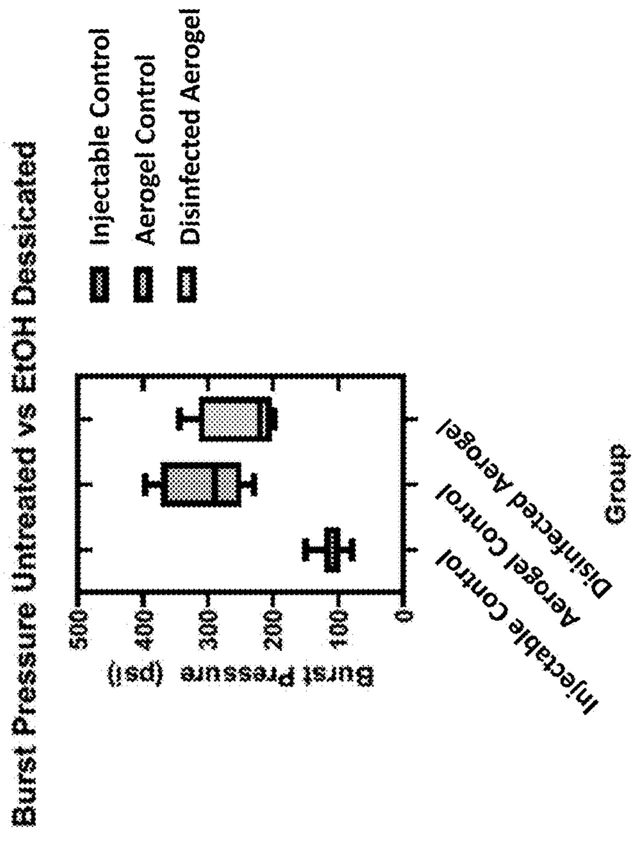
FIG. 8C is a graph showing burst pressure for an injectable hydrogel, a control aerogel implant, and a disinfected aerogel implant according to embodiments to the invention.

Burst pressures were determined by re-hydrating the aerogel implants. FIG. 8C shows no statistically significant difference in burst pressure between injectable hydrogel controls (n=10), undisinfected control aerogel implants (n=11), and disinfected aerogel implants (n=4).

Example 6: Implant Disinfection/Dehydration

Figure 9B:
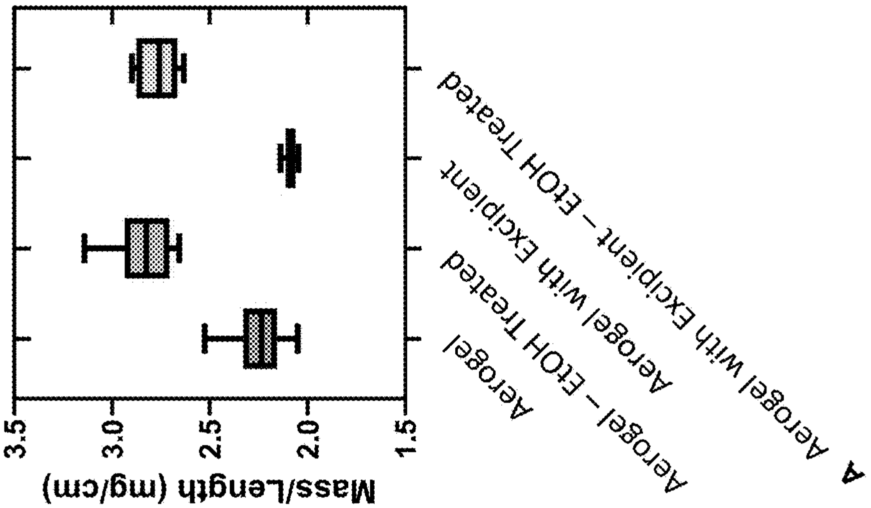
FIG. 9B is a graph showing the mass to length ratio for an aerogel, an ethanol-treated aerogel, an aerogel comprising an excipient, and an ethanol-treated aerogel comprising an excipient according to embodiments of the invention.
Figure 9A:
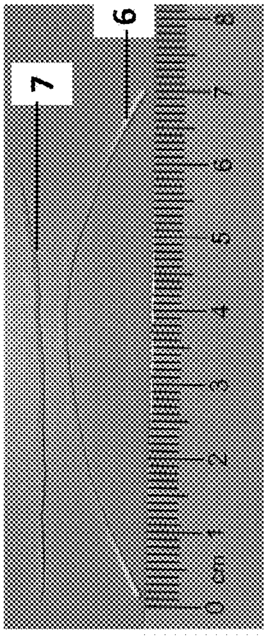
FIG. 9A is a drawing comparing a disinfected aerogel implant and a control aerogel implant according to embodiments of the invention.
Figure 9C:
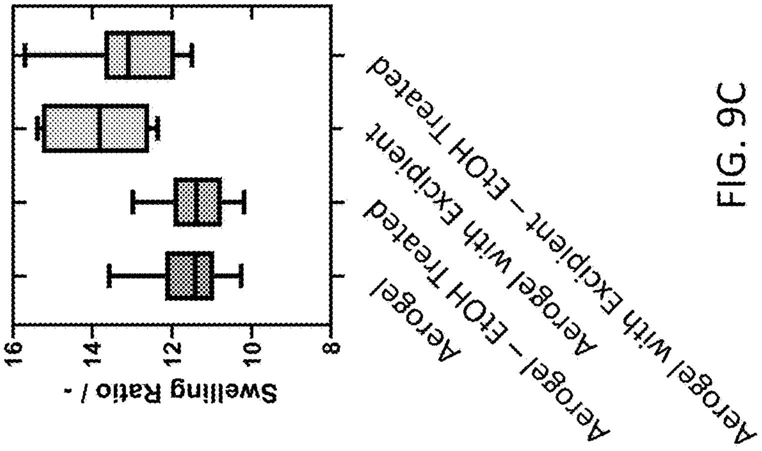
FIG. 9C is a graph showing the swelling ratios for an aerogel, an ethanol-treated aerogel, an aerogel comprising an excipient, and an ethanol-treated aerogel comprising an excipient according to embodiments of the invention.

In FIG. 9A, an 8 cm implant 6 is shown with an ethanol-treated implant 7. FIG. 9B shows the mass to length ratio is higher for the ethanol-treated aerogels than for untreated aerogels. FIG. 9C shows the ethanol treatment does not affect swelling ratio (swelling ratios are normalized to polymer content). FIGS. 9B-C show mass/length and swelling ratio data for aerogels with and without excipients.

Example 7: Implant Delivery into a Subject

Figure 10C:
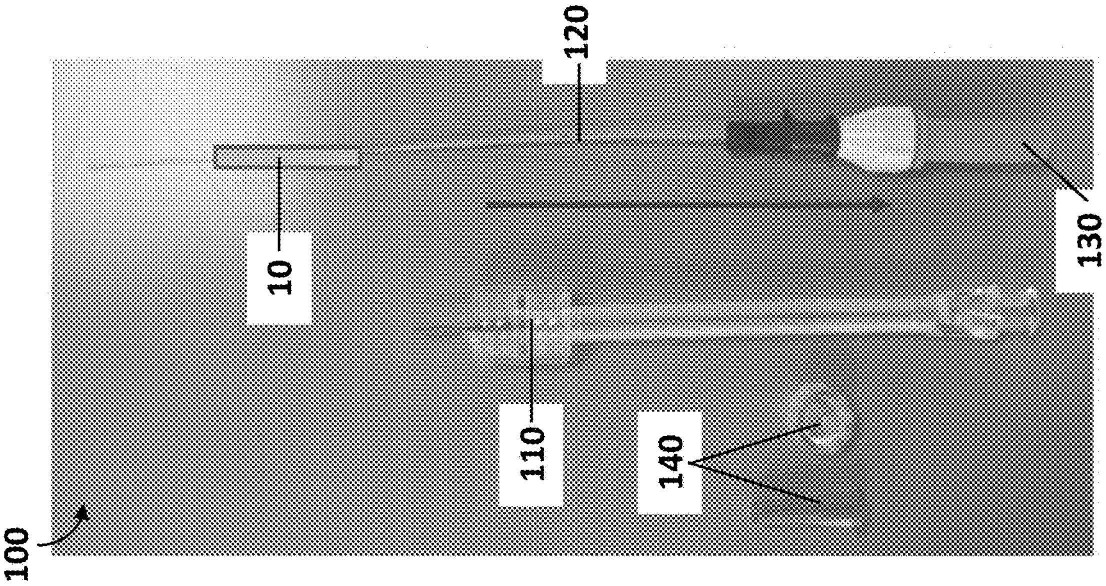
FIGS. 10A-C are drawings showing a kit for implantation of an aerogel implant according to embodiments of the invention.
Figure 10B:
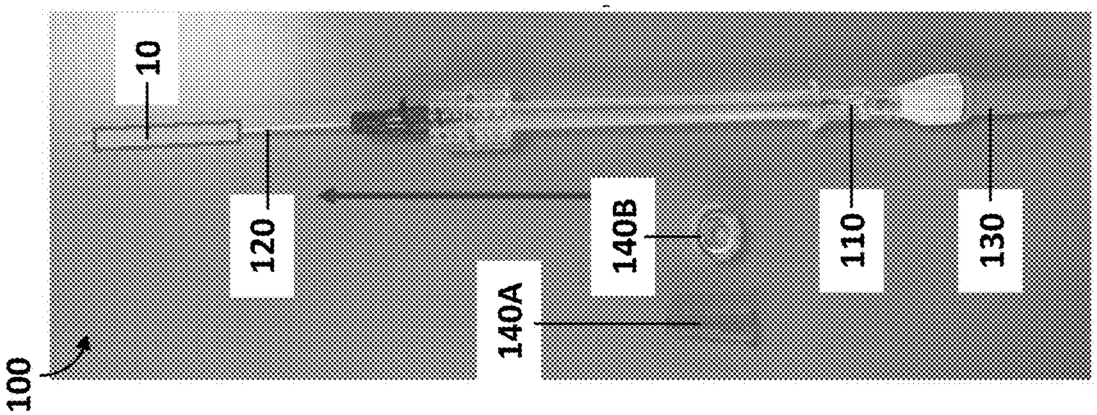
Figure 10A:
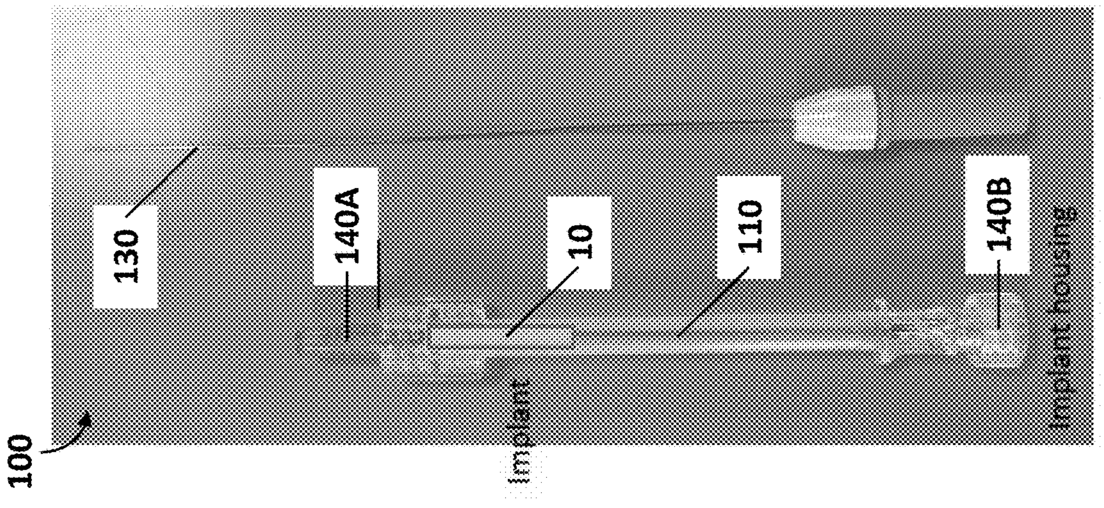

In an embodiment of the invention, an aerogel implant 10 is administered using a delivery kit 100 (FIGS. 10A-C). The delivery kit 100 comprises the aerogel implant 10 disposed inside a delivery device housing 110, a catheter 120, a guide wire 130, and optionally one or more removable housing caps (e.g., 140A-B).

As shown in FIG. 10A, the aerogel implant 10 is contained within the housing 110, optionally a first cap 140A and a second cap 140B are provided. Included with the delivery kit 100 is a guide wire 130.

At time of delivery, cap 140A is removed and replaced with a catheter 120 or a needle (not shown) as shown in FIG. 10B.

The catheter 120 or needle is inserted into the body such as a body cavity or lumen, for example a vas deferens or fallopian tube. Cap 140B is removed and guide wire 130 is inserted into the housing 110. The guide wire 130 is used to push the aerogel implant 10 out of the housing 110 and into the catheter 120.

After the aerogel implant 10 is pushed into the catheter 120, the guide wire 130 is removed from the catheter 120, and the catheter 120 is detached from the housing 110. The guide wire 130 is inserted into the catheter 120 and used to hold the aerogel implant 10 in position as the catheter 120 is removed from the body, cavity or body lumen by sliding it out of the body, cavity or body lumen toward a handle of the guide wire 130 (FIG. 10C). The aerogel implant 10 remains in the body, cavity or body lumen for a desired period of time. For example, when inserted into a vas deferens, the aerogel implant 10 can remain implanted in the vas deferens for a period of about 5 years to provide azoospermia or severe oligospermia to the subject.

The term "about" used herein in the context of quantitative measurements means±10%. For example, with a ±10% range, a number average molecular weight (Mn) or the weight average molecular weight (Mw) of "about 1,000 Daltons" can mean a molecular weight in the range of 900-1,100 Daltons.

The present invention has been described with reference to particular embodiments having various features. In light of the disclosure provided above and the claims provided below, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range, to the tenth of the unit disclosed, is also specifically disclosed. Any smaller range within the ranges disclosed or that can be derived from other endpoints disclosed are also specifically disclosed themselves. The upper and lower limits of disclosed ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. An aerogel implant comprising:

one or more polymer comprising a plurality of crosslinked poly(ethylene glycol)-based macromers, wherein, prior to crosslinking, one or more of the poly(ethylene glycol)-based macromers has a molecular weight in the range of 10 kDa to 80 kDa; and a moisture content of less than 20%;

wherein the aerogel implant is configured to swell upon implantation into a body cavity.

2. The aerogel implant of claim 1, wherein one or more of the one or more poly(ethylene glycol)-based macromers, prior to crosslinking, comprises maleimide groups.

3. The aerogel implant of claim 2, wherein one or more of the one or more poly(ethylene glycol)-based macromers, prior to crosslinking, comprises thiol functional groups.

4. The aerogel implant of claim 1, wherein the one or more polymer is a disinfected polymer.

5. The aerogel implant of claim 4, wherein the disinfected polymer is an ethanol disinfected polymer.

6. The aerogel implant of claim 1, wherein the one or more polymer is a covalently crosslinked polymer.

7. The aerogel implant of claim 6, wherein one or more of the poly(ethylene glycol)-based macromers are multi-arm poly(ethylene glycol)-based macromers.

8. The aerogel implant of claim 1, wherein upon implantation into the body cavity, the aerogel implant is configured to exert a force on the body cavity of less than about 1 N immediately after implantation and greater than about 4 N about 12 hours after implantation.

9. The aerogel implant of claim 1, wherein, the aerogel implant comprises less than about 4% water.

10. The aerogel implant of claim 1, wherein the aerogel implant is non-cytotoxic.

11. The aerogel implant of claim 1, wherein upon implantation into the body caVity, the aerogel implant swells to forrn a hydrogel;

wherein the hydrogel comprises pores; and wherein no pores of the hydrogel have a size exceeding 3 μm in diameter.

12. The aerogel implant of claim 1, wherein the aerogel implant comprises one or more of:

natural or synthetic monomers, polymers, copolymers or block copolymers, biocompatible monomers, polymers, copolymers or block copolymers, polystyrene, neoprene, polyetherether ketone (PEEK), carbon reinforced PEEK, polyphenylene, polyetherketoneketone (PEKK), polyaryletherketone (PAEK), polyphenylsulphone, polysulphone, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, fluoropolymers, polytetrafluoroethylene (PTFE), TFE (tetrafluoroethylene), polyethylene terephthalate (PET or PETE), FEP (fluorinated ethylene propylene), PFA (perfluoroalkoxy alkanes), and/or polymethylpentene (PMP) styrene maleic anhydride, styrene maleic acid (SMA), polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamide) (PNIPAM), poly (vinylmethylether), poly (ethylene oxide), poly (ethyl (hydroxyethyl) cellulose), polyoxazoline and any of its derivatives (POX), polylactide (PLA), polyglycolide (PGA), poly(lactide-co-glycolide) PLGA, poly(ϵ-caprolactone), polydiaoxanone, polyanhydride, trimethylene carbonate, poly(β-hydroxybutyrate), poly(γ-ethyl glutamate), poly (DTH-iminocarbonate), poly(bisphenol A iminocarbonate), poly(orthoester) (POE), polycyanoacrylate (PCA), polyphosphazene, polyethyleneoxide (PEO), polyethyleneglycol (PEG) or any of its derivatives, linear or multi-armed PEG and any of its derivatives, polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPAM), poly(vinyl alcohol) poly(acrylic acid) (PVOH-PAA), collagen, silk, silk fibroin, sericin, fibrin, gelatin, hyaluron, cellulose, chitin, dextran, casein, albumin, ovalbumin, heparin sulfate, starch, agar, heparin, alginate, fibronectin, keratin, pectin, elastin, ethylene vinyl acetate, ethylene vinyl alcohol (EVOH), polyethylene oxide, PLA or PLLA (poly(L-lactide) or pol(L-lactic acid)), poly(D,L-lactic acid), poly(D,L-lactide), polydimethylsiloxane or dimethicone (PDMS), poly(isopropyl acrylate) (PIPA), polyethylene vinyl acetate (PEVA), PEG styrene, perfluoropolyether (PFPE) and polytetraflurorethylene (PTFE), fluorinated polyethylene (FLPE), methyl palmitate, temperature responsive polymers, polycarbonate, polyethersulfone, polycaprolactone, polymethyl methacrylate, polyisobutylene, nitrocellulose, medical grade silicone, cellulose acetate, cellulose acetate butyrate, polyacrylonitrile, poly(lactide-co-caprolactone) (PLCL), and/or chitosan; poly (methyl methacrylate), poly (vinyl alcohol), poly (urethanes) poly (ethylene) poly (siloxanes) or silicones, poly (Vinyl pyrrolidone), poly (ethylene-co-Vinyl acetate), poly (methyl methacrylate), poly (vinyl alcohol), poly (N-vinyl pyrrolidone), poly (acrylic acid), poly (2-hydroxy ethyl methacrylate), polyacrylamide, poly (methacrylic glycol), poly (ethylene glycol), polyorthoesters, poly (lactide-co-glycolides) (PLGA), polyactide (PLA), polyanhydride, polyglycolides (PGA); polymers formed from radical polymerization such as polystyrene, poly(acrylic acid), poly (methacrylic acid), poly(ethyl methacrylate), poly (methyl methacrylate), poly(vinyl acetate), poly (ethyleneterepthalate), polyethylene, polypropylene, polybutadiene, polyacrylonitrile, poly(vinyl chloride), poly(vinylidene chloride), poly(vinyl alcohol), polychloroprene, polyisoprene, vinyl fluoride, vinylidene fluoride, trifluoroethylene, poly(methyl-α-chloracrylate), poly(ethylvinyl ketone), polymethacroleine, polyaurylmethacryate, poly(2-hydroxyethylmethamilate), poly(fumaronitrile), polychlorotrifluoroethylene, poly(acrylonitrile), polyacroleine, polyacenaphthylene, and branched polyethylene; natural polymers including rubber, cellulose, alginate, wool, amber, keratin, collagen, starch, DNA, and shellac.

13. The aerogel implant of claim 1, wherein the aerogel implant further comprises one or more contrast agents, therapeutic agent(s), hormones, anti-HIV drugs, antibiotics, and/or anti-virals.

14. The aerogel implant of claim 11, wherein upon implantation into the body cavity, a length of the aerogel implant increases by at least 50% and/or a width or a diameter of the aerogel increases by at least 50%.

15. The aerogel implant of claim 11, wherein upon implantation into the body cavity, the aerogel implant swells to exert a force on the body cavity of less than about 1 N immediately after implantation and greater than about 4 N about 12 hours after implantation.

16. The aerogel implant of claim 11, wherein the aerogel implant does not contain cellulose.

17. The aerogel implant of claim 1, wherein one or more of the one or more poly(ethylene glycol)-based macromers, prior to crosslinking, comprises thiol functional groups.

18. The aerogel implant of claim 1, wherein the aerogel implant is configured to rehydrate into a hydrogel with a burst pressure of at least 100 psi.

19. The aerogel implant of claim 1, wherein one or more of the poly(ethylene glycol)-based macromers are multi-arm poly(ethylene glycol)-based macromers.

20. The aerogel implant of claim 1, wherein the aerogel implant is capable of inducing azoospermia or severe oligospermia in vivo.

* * * * *